US007351803B2

(12) United States Patent
Johnson et al.

(10) Patent No.: US 7,351,803 B2
(45) Date of Patent: Apr. 1, 2008

(54) CD16A BINDING PROTEINS AND USE FOR THE TREATMENT OF IMMUNE DISORDERS

(75) Inventors: Leslie S. Johnson, Darnestown, MD (US); Ling Huang, Gaithersburg, MD (US); Hua Li, North Potomac, MD (US); Nadine Tuaillon, Sykesville, MD (US)

(73) Assignee: Macrogenics, Inc., Rockville, MD (US)

( * ) Notice: Subject to any disclaimer, the term of this patent is extended or adjusted under 35 U.S.C. 154(b) by 353 days.

(21) Appl. No.: 10/449,566

(22) Filed: May 29, 2003

(65) Prior Publication Data

US 2004/0010124 A1 Jan. 15, 2004

Related U.S. Application Data

(60) Provisional application No. 60/439,320, filed on Jan. 10, 2003, provisional application No. 60/384,689, filed on May 30, 2002.

(51) Int. Cl.
*C07K 16/00* (2006.01)
*C12P 21/08* (2006.01)
*C07K 17/00* (2006.01)

(52) U.S. Cl. .............................. 530/387.1; 530/387.3; 530/388.1; 530/388.22

(58) Field of Classification Search ................ None
See application file for complete search history.

(56) References Cited

U.S. PATENT DOCUMENTS

| | | | |
|---|---|---|---|
| 4,816,567 | A | 3/1989 | Cabilly et al. |
| 4,946,778 | A | 8/1990 | Ladner et al. |
| 5,116,964 | A | 5/1992 | Capon et al. |
| 5,219,728 | A | 6/1993 | Khayat et al. |
| 5,399,493 | A | 3/1995 | Emerson et al. |
| 5,428,130 | A | 6/1995 | Capon et al. |
| 5,437,994 | A | 8/1995 | Emerson et al. |
| 5,455,030 | A | 10/1995 | Ladner et al. |
| 5,545,806 | A | 8/1996 | Lonberg et al. |
| 5,569,825 | A | 10/1996 | Lonberg et al. |
| 5,624,821 | A | 4/1997 | Winter et al. |
| 5,641,863 | A | 6/1997 | Schreiber et al. |
| 5,834,597 | A * | 11/1998 | Tso et al. ............ 530/387.3 |
| 5,837,821 | A | 11/1998 | Wu |
| 5,976,831 | A | 11/1999 | Peltz et al. |
| 5,985,599 | A | 11/1999 | McKenzie et al. |
| 6,025,158 | A | 2/2000 | Gonzalez et al. |
| 6,103,889 | A | 8/2000 | Whitlow et al. |
| 6,194,551 | B1 | 2/2001 | Idusogie et al. |
| 6,207,804 | B1 | 3/2001 | Huston et al. |
| 6,277,375 | B1 | 8/2001 | Ward |
| 6,528,624 | B1 | 3/2003 | Idusogie et al. |

FOREIGN PATENT DOCUMENTS

| EP | 0 753 065 | 1/1997 |
|---|---|---|
| EP | 0 343 950 B1 | 10/2000 |
| WO | WO 00/42072 | 7/2000 |
| WO | WO 02/061090 | 8/2002 |

OTHER PUBLICATIONS

Vaswani et al. Annals of Allergy, Asthma, & Immunology. 1998, 81:105-116, 119 (pp. 117-118 do not exit).*
Brummell et al. Biochemistry. 1993. 32;4:1180-1187.*
Rudikoff et al., PNAS 1982 vol. 79, pp. 1979-1983.*
Amit et al. Science 1986. 233:747-753.*
Alegre, M-L et al. (Jun. 1, 1992). "Effect of a Single Amino Acid Mutation on the Activating and Immunosuppressive Properties of a 'Humanized' OKT3 Monoclonal Antibody," *J. Immunol.* 148(11):3461-3468.
Altschul, S. F. et al. (1990). "Basic Local Alignment Search Tool," *J. Mol. Biol.* 215:403-410.
Anonymous (Dec. 20, 2000). "PerCP Mouse Anti-Human Monoclonal Antibody," PharMingen Technical Data Sheet, CD3/CD16/CD45, 2 pages.
Anonymous (Jun. 6, 2001). "R-Phycoerythrin (R-PE)-Conjugated Mouse Anti-Human Monoclonal Antibody," BD PharMingen Technical Data Sheet., CD16, one page.
Barbas, III, C. F. et al. (Sep. 1991). "Assembly of Combinatorial Antibody Libraries on Phage Surfaces: The Gene III Site," *PNAS* 88:7978-7982.
Bedzyk, W. D. et al. (Jan. 25, 1989). "Comparison of Variable Region Primary Structures Within Anti-Fluorescein Idiotype Family," *J. Biol. Chem.* 264(3):1565-1569.
Bird, R. E. et al. (Oct. 21, 1988). "Single-Chain Antigen-Binding Proteins," *Science* 242:423-426.
Boder, E. T. et al. (Sep. 26, 2000). "Directed Evolution of Antibody Fragments with Monovalent Femtomolar Antigen-Binding Affinity," *PNAS.* 97(20):10701-10705.
Boder, E. T. et al. (Jun. 1997). "Yeast Surface Display for Screening Combinatorial Polypeptide Libraries," *Nature Biotechnology* 15:553-557.
Bolland, S. et al. (1999). "Inhibitory Pathways Triggered by ITIM-Containing Receptors," *Adv. In Immunol.* 72:149-177.
Bussel, J. et al. (1988). "Infusion of a Monoclonal Anti-FcR III in Patients with Refractory ITP," *Neo-Adjuvant Chemotherapy* 169:883-887.
Canfield, S. M. et al. (1991). "The Binding Affinity of Human IgG for Its High Affinity Fc Receptor is Determined by Multiple Amino Acids in the $C_H2$ Domain and Is Modulated by Hinge Region," *J. Exp. Med.* 173:1483-1491.
Carter, P. et al. (1992). "High Level *Escherichia coli* Expression and Production of a Bivalent Humanized Antibody Fragment," *Bio/Technology* 10:163-167.

(Continued)

*Primary Examiner*—Maher M. Haddad
*Assistant Examiner*—Chun Crowder
(74) *Attorney, Agent, or Firm*—King & Spalding LLP; Margaret B. Brivanlou

(57) ABSTRACT

CD16A binding proteins useful for the reduction of a deleterious immune response are described. In one aspect, humanized anti-CD16A antibodies, optionally lacking effector function, are used for treatment of immune disorders such as idiopathic thrombocytopenic purpura and autoimmune hemolytic anemia.

18 Claims, 12 Drawing Sheets

OTHER PUBLICATIONS

Casali, P. et al. (1986). "Human Monoclonals from Antigen-Specific Selection of B Lymphocytes and Transformation by EBV," *Science* 234:476-552.

Cheung, R. C. et al. (1990). "Epitope-Specific Antibody Response to the Surface Antigen of Duck Hepatitis B Virus in Infected Ducks," *Virology* 176:546-552.

Chothia, C. et al. (Dec. 1989). "Conformation of Immunoglobulin Hypervariable Regions," *Nature* 342:877-883.

Clarkson, S. B. et al. (Aug. 1986). "Blockade of Clearance of Immune Complexes by an Anti-Fcγ Receptor Monoclonal Antibody," *J. Exp. Med.* 164:474-489.

Clarkson, S. B. et al. (1986). "Treatment of Refractory Immune Thrombocytopenic Purpura with an Anti-Fcγ-Receptor Antibody," *N. Engl. J. Med.* 314(19):1236-1239.

Clynes, R. A. et al. (Apr. 2000). "Inhibitory Fc Receptors Modulate In Vivo Cytoxicity Against Tumor Targets," *Nat. Med.* 6(4):443-446.

Co, M. S. et al. (Apr. 1991). "Humanized Antibodies for Antiviral Therapy," *PNAS* 88:2869-2873.

Daugherty, P. S. et al. (1998). "Antibody Affinity Maturation Using Bacterial Surface Display," *Protein Enginee.* 11(9):825-832.

Ding, Y.-H. et al. (Apr. 1998). "Two Human T Cell Receptors Bind in a Similar Diagonal Mode to the HLA-A2/Tax Peptide Complex Using Different TCR Amino Acids," *Immunity* 8:403-411.

Duncan, A. R. et al. (1988). "Localization of the Binding Site for the Human High-Affinity Fc Receptor on IgG," *Nature* 332:563-564.

Edge, J . C. et al. (1997). "Cell Type-Specific Glycoforms of FcγRIIIa (CD16): Differential Ligand Binding," *J. Immunol.* 159(8):3849-3857.

Fleit, H. B. et al. (May 1982). "Human Neutrophil Fc$_\gamma$ Receptor Distribution and Structure," *PNAS* 79:3275-3279.

Foote, J. et al. (1992). "Antibody Framework Residues Affecting the Conformation of the Hypervariable Loops," *J. Mol. Biol.* 224:487-499.

Friend, P.J. et al. (1999). "Phase I Study of an Engineered Aglycosylated Humanized CD3 Antibody in Renal Transplant Rejection," *Transplantation* 68(11):1632-1637.

Hoogenboom, H. R. and Winter, G. (1991). "By-Passing Immunisation Human Antibodies from Synthetic Repertoires of Germline VH Gene Segments Rearranged in Vitro," *J. Mol. Biol.* 227:381-388.

Hudson, P. J. et al. (Jan. 2003). "Engineered Antibodies," *Nature Medicine* 9(1):129-139.

Huse, W. D. et al. (Dec. 1989). "Generation of a Large Combinatorial Library of the Immunoglobulin Repertoire in Phage Lambda," *Science* 246:1275-1281.

Jefferis, R. et al. (1995). "Recognition Sites on Human IgG for Fcγ Receptors: the Role of Glycosylation," *Immunology Letters* 44:111-117.

Jefferis, R. et al. (1997). "Glycosylation of Antibody Molecules: Structural and Functional Significance," *Chem. Immunol.* 65:111-128.

Jones, P. T. et al. (1986). "Replacing the Complementarity Determining Regions in a Human Antibody with Those from Mouse," *Nature* 321:522-525.

Kirkland, T. N. et al. (1986). "Analysis of the Fine Specificity and Cross-Reactivity of Monoclonal Anti-Lipid A Antibodies," *J. Immunol* 137(11):3614-3619.

Koumemis, I. L. et al. (2000). "Modulating Pharmcokinetics of An Anti-Interleukin-8 F(ab')$_2$ by Amine-Specific PEGylation with Preserved Bioactivity," *Int. J. Pharm.* 198:83-95.

Krebs, B. et al. (2001). "High-Throughput Generation and Engineering of Recombinant Human Antibodie," *J. Imm. Methods* 254:67-84.

Lanzavecchia, A. et al. (1987). "The Use of Hybrid Hybridoma Target Human Cytotoxic T Lymphocytes," *Eur. J. Immunol.* 17:105-111.

Larrick, J. W. et al. (1991). "Recombinant Antibodies," *Hum Antibodies Hybribomas* 2:172-189.

Leong, S. R. et al. (2001). "Adapting Pharmacokinetic Properties of a Humanized Anti-Interleukin-8 Antibody for Therapeutic Applications Using Site-Specific Pegylation," *Cytokine* 16(3):106-119.

Li, M. et al. (Mar. 1996). "Reconstitution of Human FcγRIII Cell Type Specificity in Transgenic Mice," *J. Exp. Med.* 183:1259-1263.

Lucas, B. K. et al. (1996). "High-Level Production of Recombinant Proteins in CHO Cells Using A Dicistronic DHFR Intron Expression Vector," *Nucleic Acids Res.* 24(9):1774-1779.

Malmqvist, M. et al. (1997). "Biomolecular Interaction Analysis: Affinity Biosensor Technologies for Functional Analysis of Proteins," *Curr. Opinion Chem. Biol.* 1:378-383.

McCrae, K. R. et al. (2001). "Platelets: An Update on Diagnosis and Management of Thrombocytopenic Disorders," *Hematogology* pp. 282-305.

Mizutani, H. et al. (Aug. 1, 1993). "Development and Characterization of Monoclonal Antiplatelet Autoantibodies from Autoimmune Thrombocytopenic Purpura-Prone (NZW x BXSB)F$_1$ Mice," *Blood* 82(3):837-844.

Moldenhauer, G. et al. (1990). "Identity of HML-1 Antigen on Intestinal Intraepithelial T Cells and of B-ly7 Antigen on Hairy Cell Leukaemia," *Scand. J. Immunol.* 32:77-82.

Morel, G. A. et al. (1988). "Monoclonal Antibodies to Bovine Serum Albumin: Affinity and Specificity Determination," *Molec. Immunol.* 25(1):7-15.

Needleman, S. B. et al. (1970). "A General Method Applicable to the Search for Similarities in the Amino Acid Sequence of Two Proteins," *J. Mol. Biol.* 48:443-453.

O'Connell, D. et al. (2002). "Phage *versus* Phagemid Libraries for Generation of Human Monoclonal Antibodies," *J. Mol. Biol.* 321:49-56.

Orlandi, R. et al. (May 1989). "Cloning Immunoglobulin Variable Domains for Expression by the Polymerase Chain Reaction," *PNAS* 86:3833-3837.

Oyaizu, N. et al. (1988). "NZW x BXSB)F$_1$ Mouse: A New Animal Model of Idiopathic Thrombocytopenic Purpura," *J. Exp. Med.* 167:2017-2022.

Padlan, E. A. (1991). "A Possible Procedure for Reducing the Immunogenicity of Antibody Variable Domains While Preserving Their Ligand-Binding Properties," *Mol. Immunol* 28(4/5):489-498.

Pearson, W. R. et al. (1988). "Improved Tools for Biological Sequence Comparison," *PNAS* 85:2444-2448.

Queen, C. et al. (1989). "A Humanized Antibody that Binds to the Interleukin 2 Receptor," *PNAS USA* 86:10029-10033.

Radaev, S. et al. (May 11, 2001). "Recognition of IgG by Fcγ Receptor," *J. of Biological Chemistry* 276(19):16478-16483.

Ravetch, J. V. et al. (Aug. 1989). "Alternative Membrane Forms of FcγRIII(CD16) on Human Natural Killer Cells and Neutrophils," *J. Exp. Med.* 170:481-497.

Ravetch, J. V. et al. (2001). "I$_G$G Fc Receptors," *Annual Rev. Immunol.* 19:275-290.

Ravtech, J. V. et al. (1991). "Fc Receptors," *Annual Rev. Immunol.* 9:457-492.

Riechmann, L. et al. (1988). "Reshaping Human Antibodies for Therapy," *Nature* 332:323-327.

Samuelsson, A. et al. (Jan. 19, 2001). "Anti-Inflammatory Activity of IVIG Mediated Through the Inhibitory Fc Receptor," *Science* 291:484-486.

Scallon, B. J. et al. (1989). "A Human Immunoglobulin G Receptor Exists in Both Polypeptide-Anchored and Phosphtidylinositol-Glycan Anchored Forms," *PNAS* 86:5079-5093.

Schier, R. et al. (1996). "Isolation of Picomolar Affinity Anti-c-erbB-2 Single-Chain Fv by Molecular Evolution of the Complementary Determining Regions in the Center of the Antibody Binding Site," *J. Mol. Biol* 263:551-567.

Schmidt, R. E. et al. (1989). "N2 Cluster Report: CD 16," In *Leukocyte Typing IV White Cell Differentiation Antigens*, Knapp, W. et al., eds., Oxford University Press, pp. 574-597.

Shields, R. L. et al. (2001). "High Resolution Mapping of the Binding Site on Human IgG1 for FcγRI, FcγRIII, and FcRN and Design of IgG1 Variants with Improved Binding to the FcγR*," J. of Biological Chemistry 276(9):6591-6604.

Smith, T. F. et al. (1981). "Comparison of Biosequence," *Adv. Appl. Math.* 2:482-489.

Soubrane, C. et al. (Jan. 1, 1993). "Biologic Response Anti-CD16 Monoclonal Antibodies Therapy in a Human Immunodeficiency Virus-Related Immune Thrombocytopenic Purpura Patient," *Blood* 81(1):15-19.

Stähli, C. et al. (1983). "Distinction of Epitopes by Monoclonal Antibodies," *Methods in Enzymology*, 92:242-253.

Tao, M.-H. (Oct. 15, 1989). "Studies of Aglycosylated Chimeric Mouse-Human IgG: Role of Carbohydrate in the Structure and Effector Functions Mediated by the Human IgG Constant Region," *J. of Immunology* 143(8):2595-2601.

Woof, J. et al. (1986). "Localisation of the Monocyte-Binding Region on Human Immunoglobulin G," *Mol. Imm.* 23(3):319-330.

Xu, D. et al. (2000). "In Vitro Characterization of Five Humanized OKT3 Effector Function Variant Antibodies," *Cell Immunology* 200:16-26.

Zu Putlitz, J. et al. (Jul. 1990) "Antibody Prosecution in Baculovirus Infected Insect Cells," *Bio/Technology* 8:651-654.

International Search Report mailed on Oct. 20, 2003, for PCT application No. PCT/US03/17111 filed May 29, 2003, 6 pages.

Tamm, A. et al. (1996). "The Binding Epitopes of Human CD 16 (FcγRIII) Monoclonal Antibodies," *Journal of Immunology* 157:1576-1581.

Zhu, X. et al. (1998). "Intracellular Expression of FcγRIII (CD16) and Its Mobilization by Chemoattractants in Human Eosinophils[1]," *Journal of Immunology* 161:2574-2579.

Cartron et al., "Therapeutic activity of humanized anti-CD20 monoclonal antibody and polymorphism in IgG Fc receptor FCγRIIIa gene." *Blood* Feb. 1, 2002; 99(3):754-8.

Clynes et al., "Uncoupling of immune complex formation and kidney damage in autoimmune glomerulonephritis." *Science* Feb. 13, 1998; 279(5353):1052-1054.

Edberg JC, Kimberly, RP., "Cell type-specific glycoforms of Fc gamma RIIIa (CD16): differential ligand binding." *J. Immunol.* Oct. 15, 1997; 159(8):3849-3857.

Farag, S.F. et al., "FcγRIIIa and FcγRIIIa Polymorphisms Do Not Predict Response to Rituximab in B-Cell Chronic Lymphocytic Leukemia." *Blood* Feb. 15, 2004; 103(4):1472-4; pre-published online Oct. 16, 2003.

Fijen et al., "The role of Fcγreceptor polymorphisms and C3 in the immune defence against Neisseria meningitidis in complement-deficient individuals." *Clin Exp Immunol.* May 2000; 120(2):338-45.

Frank et al., "Defective reticuloendothelial system Fc-receptor function in systemic lupus erythematosus." *N Engl J Med.* Mar. 8, 1979; 300(10):518-523.

Fujiwara et al., "Determination of granulocyte-specific antigens on neutrophil FcA receptor IIIb by PCR-preferential homoduplex formation assay, and gene frequencies in the Japanese population." *Vox Sang.* 1999; 77(4):218-22.

Hibbs et al. "Membrane-proximal Ig-like domain of Fc gamma RIII (CD16) contains residues critical for ligand binding." J Immunol. May 1, 1994;152(9):4466-4474.

Hosea et al., "Opsonic requirements for intravascular clearance after splenectomy." N Engl J Med. Jan. 29, 1981; 304(5):245-250.

Imbach et al., "High-dose intravenous gammaglobulin for idiopathic thrombocytopenic purpura in childhood." *Lancet.* Jun. 6, 1981; 1(8232):1228-1231.

Jones et al., "Two distinct classes of IgG Fc receptors on a human monocyte line (U937) defined by differences in binding of murine IgG subclasses at low ionic strength." *J Immunol.* Nov. 1985; 135(5):3348-53.

Khayat et al., "Soluble circulating Fc gamma receptors in human serum. A new ELISA assay for specific and quantitative detection." *J Immunol Methods.* Jun. 26, 1987; 100(1-2):235-241.

Kim et al., "Analysis of FcγRIII and IgG polymorphism reveals functional and evolutionary implications of protein-protein interaction." *J Mol Evol.* Jul. 2001; 53(1):1-9.

Kurlander et al., "The blockade of Fc receptor-mediated clearance of immune complexes in vivo by a monoclonal antibody (2.4G2) directed against Fc receptors on murine leukocytes." *J Immunol.* Aug. 1984; 133(2):855-862.

McDougal et al., "Binding of immunoglobulin G aggregates and immune complexes in human sera to Staphylococci containing protein A." *J Clin Invest.* Apr. 1979; 63(4):627-636.

Nagarajan et al., "Ligand binding and phagocytosis by CD16 (Fc gamma receptor III) isoforms. Phagocytic signaling by associated zeta and gamma subunits in Chinese hamster ovary cells." *J Biol Chem.* Oct. 27, 1995; 270(43):25762-70.

Olsson et al., "Serum from patients with chronic idiopathic thrombocytopenic purpura frequently affect the platelet function." *Thromb Res.* Aug. 15, 2002; 107(3-4):135-139.

Parker CW., "Spectrofluorometric Methods." Chapter 14 of *Handbook of Experimental Immunology*. Weir ed. Blackwell Scientific Publications: pp. 14.1-14.25.

Tebo et al., "Fcγ receptor-mediated phagocytosis of *Plasmodium falciparum*-infected erythrocytes in vitro," *Clin Exp Immunol.* Nov. 2002; 130(2):300-6.

Todorovska et al., "Design and application of diabodies, triabodies and tetrabodies for cancer targeting." *J Immunol Methods.* Feb. 1, 2001; 248(1-2):47-66. Review.

Treon, S.P. et al., "Polymorphisms in Fcγ RIIIa(CD16) Receptor Expression Are Associated with Clinical Response to Rituximab in Waldenstrom's Macroglobulinemia." *Biologic Therapy of Lymphomas: Laboratory Investigations.* 537a.

Van Sorge et al., "FcγR polymorphisms: Implications for function, disease susceptibility and immunotherapy." Tissue Antigens. 2003; 61:189-202.

Warmerdam et al., "Molecular basis for a polymorphism of human Fc gamma receptor II (CD32)." *J Exp Med.* Jul. 1, 1990; 172(1):19-25.

West et al., "Natural cytotoxic reactivity of human lymphocytes against a myeloid cell line: characterization of effector cells." *J Immunol.* Jan. 1977;118(1):355-361.

Bolt et al., 1993, "The generation of a humanized, non-mitogenic CD3 monoclonal antibody which retains in vitro immunosuppressive properties," Eur. J. Immunol. 23(2):403-11.

Bussel et al., 2000, "Fc receptor blockade and immune thrombocytopenic purpura," Semin. Hematol. 37(3):261-6.

Cassatella et al., 1989, "Fc gamma R(CD16) interaction with ligand induces Ca2+ mobilization and phosphoinositide turnover in human natural killer cells. Role of Ca2+ in Fc gamma R(CD16)-induced transcription and expression of lymphokine genes," J. Exp. Med. 169(2):549-67.

Kimberly et al., 1989, "In vivo handling of soluble complement fixing Ab/dsDNA immune complexes in chimpanzees," J. Clin. Invest. 84(3):962-70.

* cited by examiner

CD16A BINDING PROTEINS AND USE FOR THE TREATMENT OF IMMUNE DISORDERS

CROSS-REFERENCE TO RELATED APPLICATIONS

This application claims benefit of provisional patent application No. 60/384,689, filed May 30, 2002, and provisional patent application No. 60/439,320, filed Jan. 10, 2003, the entire contents of which are incorporated herein by reference for all purposes.

FIELD OF THE INVENTION

The invention relates to CD16A binding proteins and methods for treatment of immune disorders. The invention finds application in the fields of biomedicine and immunology.

BACKGROUND

Fcγ receptors (FcγR) are cell surface receptors that bind the Fc region of immunoglobulin G (IgG) molecules. Among other functions, these receptors couple the formation of antibody-antigen complexes to effector cell responses. For example, cross-linking of activating Fcγ receptors by immune complexes can result in the phagocytosis of pathogens, killing of foreign and transformed cells by direct cytotoxicity, the clearance of toxic substances, and the initiation of an inflammatory response. Notably, the Fcγ receptors play a key role in autoimmunity. Autoantibody binding to activating Fc receptors triggers the pathogenic sequelae of autoimmune diseases such as idiopathic thrombocytopenic purpura, arthritis, systemic lupus erythrematosus, autoimmune hemolytic anemia, and others.

In humans and rodents there are three classes of Fcγ receptors, designated FcγRI, FcγRII, and FcγRIII (see, Ravetch and Bolland, 2001 *Annual Rev. Immunol* 19:275-90; and Ravetch and Kinet, 1991, *Annual Rev. Immunol.* 9:457-92). FcγRI sites are generally occupied by monomeric IgG, while RII and RIII receptors are generally unoccupied and available to interact with immune complexes. FcγRI, also called CD64, binds monomeric IgG with high affinity, and is present on monocytes and macrophages. FcγRII, also called CD32, binds to multimeric IgG (immune complexes or aggregated IgG) with moderate affinity, and is present on a variety of cell types, including B cells, platelets, neutrophils, macrophages and monocytes. FcγRIII, also called CD16, binds to multimeric IgG with moderate affinity and is the predominant activating FcγR on myeloid cells. FcγRIII is found in two forms. FcγRIIIA (CD16A), a transmembrane signaling form (50-65 kDa), is expressed by NK cells, monocytes, macrophages, and certain T cells. FcγRIIIB (CD16B), a glycosyl-phosphatidyl-inositol anchored form (48 kDa) form, is expressed by human neutrophils. See, e.g., Scallon et al., 1989, *Proc. Natl. Acad. Sci. U.S.A.* 86:5079-83 and Ravetch et al., 1989, *J. Exp. Med.* 170:481-97. Protein and nucleic acid sequences for CD16A are reported in Genbank as accession numbers P08637 (protein) and X52645 (nucleic acid) and in SWISS-PROT as accession number CAA36870. Protein and nucleic acid sequences for CD16B are reported in Genbank as accession numbers O75015 (protein) and X16863 (nucleic acid) and in SWISS-PROT as CAA34753.

SUMMARY OF THE INVENTION

In one aspect, the invention provides a CD16A binding protein that may be used for treatment of an individual with an autoimmune disease. CD16A binding proteins of the invention are other than mouse antibodies, and include chimeric, human and humanized anti-CD16A monoclonal antibodies, fragments thereof, single chain antibodies, and other binding proteins comprising a $V_H$ domain and/or a $V_L$ domain.

In one aspect the CD16A binding protein comprises a Fc region derived from a human IgG heavy chain (e.g., a Fc region derived from human $IgG_1$) where the Fc region lacks effector function and/or is modified to reduce binding to a Fc effector ligand. In one embodiment, the CD16A binding protein is not glycosylated, for example, due to a substitution at residue 297 of the Fc region.

In one aspect, the CD16A binding protein is a humanized 3G8 antibody with a $V_H$ domain comprising three complementarity determining regions (CDRs) derived from the $V_H$ domain of mouse monoclonal antibody 3G8. In one embodiment, the $V_H$ domain has the sequence of the $V_H$ domain of Hu3G8$V_H$-1. In one embodiment, the CDRs of the binding protein have the sequence of the mouse CDRs. In some versions, the $V_H$ domain CDRs differ from those of 3G8 at least by one or more of the following substitutions: Val at position 34 in CDR1, Leu at position 50 in CDR2, Phe at position 52 in CDR2, Asn at position 54 in CDR2, Ser at position 60 in CDR2, Ser at position 62 in CDR2, Tyr at position 99 in CDR3, and Asp at position 101 of CDR3. In one embodiment, the $V_H$ domain has the sequence of the $V_H$ domain of Hu3G8$V_H$-22. In one embodiment $V_H$ domain comprises an FR3 domain having the sequence of SEQ ID NO:51. The $V_H$ domain may be linked to an antibody heavy chain constant domain, for example the human Cγ1 constant domain.

In some versions the CD16A binding protein has a $V_H$ domain having a sequence set forth in Table 3. In some versions the CD16A binding protein has a $V_H$ domain that differs from the sequence of Hu3G8VH-1 by one or more of the substitutions shown in Table 1.

In one aspect, the CD16A binding protein is a humanized 3G8 antibody with a $V_L$ domain comprising three complementarity determining regions (CDRs) derived from the $V_L$ domain of mouse monoclonal antibody 3G8. In one embodiment, the CDRs of the binding protein have the sequence of the mouse CDRs. In some versions, the $V_L$ domain CDRs differ from those of 3G8 at least by one or more of the following substitutions: Arg at position 24 in CDR1; Ser at position 25 in CDR1; Tyr at position 32 in CDR1; Leu at position 33 in CDR1; Ala at position 34 in CDR1; Asp, Trp or Ser at position 50 in CDR2; Ala at position 51 in CDR2; Ser at position 53 in CDR2; Ala or Gln at position 55 in CDR2; Thr at position 56 in CDR2; Tyr at position 92 in CDR3; Ser at position 93 in CDR3; and Thr at position 94 in CDR3. In one embodiment, the $V_L$ domain has the sequence of the $V_L$ domain of Hu3G8VL-1, Hu3G8VL-22 or Hu3G8VL-43. The $V_L$ domain may be linked to an antibody light chain constant domain, for example the human Cκ constant region.

In some versions the CD16A binding protein has a $V_L$ domain having a sequence set forth in Table 4. In some versions the CD16A binding protein has a $V_L$ domain that differs from the sequence of Hu3G8VL-1 by one or more of the substitutions shown in Table 2.

In one aspect, the CD16A binding protein comprises both a $V_H$ domain and a $V_L$ domain, as described above (which may be prepared by coexpression of polynucleotides encoding heavy and light chains). Optionally the humanized heavy chain variable region comprises a sequence set forth in Table 3 and/or the humanized light chain variable region comprises a sequence set forth in Table 4. For example, in exemplary embodiments, the binding protein has a heavy chain variable region having the sequence of SEQ ID NO:113 and a light chain variable region having the sequence of SEQ ID NO:96, 100 or 118. In another exemplary embodiment, the binding protein has a heavy chain variable region having the sequence of SEQ ID NO:109 and light chain variable regions having the sequence of SEQ ID NO:96. In another exemplary embodiment, the binding protein has a heavy chain variable region having the sequence of SEQ ID NO:104 and a light chain variable region having the sequence of SEQ ID NO:96.

In an embodiment, the CD16A binding protein is tetrameric antibody comprising two light chains and two heavy chains, said light chains comprising a $V_L$ domain and a light chain constant domain and said heavy chains comprising a $V_H$ domain and a heavy chain constant domain. In an embodiment, the light chain constant domain is human Cκ and/or the heavy chain constant region is Cγ1.

In one embodiment of the invention, the CD16A binding protein comprises an antigen binding site that binds CD16A or sCD16A with a binding constant of less than 5 nM.

In one embodiment, the CD16A binding protein comprises an aglycosyl Fc region that has reduced binding to at least one Fc effector ligand compared to a reference CD16A binding protein that comprises an unmodified Fc region (e.g., a human $IgG_1$ Fc domain glycosylated at position 297). The Fc effector ligand can be FcγRIII or the C1q component of complement.

In one embodiment, the invention provides a CD16A binding protein that is humanized antibody that binds to CD16A and inhibits the binding of Fc to CD16.

In an aspect, the invention provides a pharmaceutical composition comprising of CD16A binding protein described herein and a pharmaceutically acceptable excipient.

In an aspect, the invention provides an isolated polynucleotide, optionally an expression vector, encoding a $V_H$ domain of a CD16A binding protein described herein. In an aspect, the invention provides an isolated nucleic acid, optionally an expression vector, encoding a $V_L$ domain of a CD16A binding protein described herein. In an aspect, the invention provides a cell, optionally a mammalian cell, comprising a polynucleotide described herein. In an aspect, the invention a cell line, optionally a mammalian cell line, expressing a CD16A binding protein described herein.

The invention further provides a method of reducing an deleterious immune response (or undesired immune response) in a mammal comprising administering to a mammal a CD16A binding protein described herein. In an embodiment, reducing the deleterious immune response comprises protecting against antibody-mediated platelet depletion.

In one aspect, the invention provides a method of treating an deleterious immune response in a mammal without inducing neutropenia in the mammal (e.g., severe neutropenia or moderate neutropenia), where the method comprises administering to the mammal a CD16A binding protein having an Fc region derived from human IgG, and where the amino acid at position 297 of the Fc region is aglycosyl.

In embodiments of the above-described methods, the deleterious immune response is an inflammatory response, for example, an inflammatory response caused by an autoimmune disease. In an embodiment, the inflammatory response is caused by idiopathic thrombocytopenic purpura (ITP), rheumatoid arthritis (RA), systemic lupus erythrematosus (SLE), autoimmune hemolytic anemia (AHA), scleroderma, autoantibody triggered urticaria, pemphigus, vasculitic syndromes, systemic vasculitis, Goodpasture's syndrome, multiple sclerosis (MS), psoriatic arthritis, ankylosing spondylitis, Sjögren's syndrome, Reiter's syndrome, Kawasaki's disease, polymyositis and dermatomyositis. Other examples of diseases or conditions that can be treated according to the invention also include any diseases susceptible to treatment with intravenous immunoglobulin (IVIG) therapy (e.g., allergic asthma). The invention provides CD16A binding proteins that both protect against autoimmune diseases and do not result in significant neutrophil diminution in a mammal. In an embodiment, the CD16A binding proteins are anti-CD16A antibodies. These CD16A binding proteins are particularly advantageous for use as human therapeutics. In one aspect, the invention provides a method of treating an autoimmune disease in a mammal without neutrophil diminution or neutropenia in the mammal, by administering a CD16A binding protein having an Fc region derived from human IgG and an aglycosyl amino acid at position 297 of each of the $C_H2$ domains of the Fc region.

In yet another aspect, the invention provides a method of inhibiting the binding of IgG antibodies to FcγRIII on a cell by contacting the cell with a CD16A binding protein under conditions in which the CD16A binding protein binds the FcγRIII on the cell.

In one aspect, the invention provides a method of making a CD16A binding protein with improved therapeutic efficacy in treating an deleterious immune response, comprising the following steps: i) obtaining a first CD16A binding protein, where the first CD16A binding protein comprises an Fc region derived from IgG; and ii) modifying the Fc region of the first CD16A binding protein to produce a second CD16A binding protein that is aglycosylated at position 297 of the Fc region, where the second CD16A binding protein is more effective in treating the deleterious immune response when administered to a mammal than the first CD16A binding protein.

In one aspect, the invention provides a method of making a CD16A binding protein with improved therapeutic efficacy in treating an deleterious immune response, comprising the following steps: i) obtaining a first CD16A binding protein, wherein the first CD16A binding protein comprises an Fc region derived from IgG; and ii) modifying the Fc region of the first CD16A binding protein to produce a second CD16A binding protein that has reduced binding to an Fc effector ligand compared to the unmodified Fc region of the first CD16A binding protein, where the second CD16A binding protein is more effective in treating the deleterious immune response when administered to a mammal than the first CD16A binding protein. In one embodiment, the Fc effector ligand is FcγRIII or the C1q component of complement.

In one aspect the method involves administering a CD16A binding protein to reduce a deleterious immune response in a subject without eliciting one or more significant deleterious effects that result from 3G8 administration, or eliciting significantly lower levels of such effects than does administration of murine 3G8.

In one embodiment of the invention, the improved therapeutic efficacy in treating a deleterious immune response comprises improved effectiveness at protecting against antibody-mediated platelet depletion. The deleterious immune response is optionally due to idiopathic thrombocytopenic purpura (ITP) or the administration of murine monoclonal antibody 6A6 to a muFcγRIII–/–, huFcγRIIIA transgenic mouse.

The invention provides the use of a CD16A binding protein comprising an Fc region derived from a human IgG heavy chain, wherein the Fc region lacks effector function, for treatment of an immune disorder or for preparation of a medicament for treatment of an immune disorder.

BRIEF DESCRIPTION OF THE FIGURES

FIG. 15(A) shows data points for each dose at indicated times. FIG. 15(B) shows dose response at the 5 hour time point.

FIG. 16(A) shows administration of Hu3G8-5.1-N297Q. FIG. 16(B) shows administration of Hu3G8-22.1-N297Q and Hu3G8-22.43-N297Q.

DETAILED DESCRIPTION

1. Definitions

Figure 1:
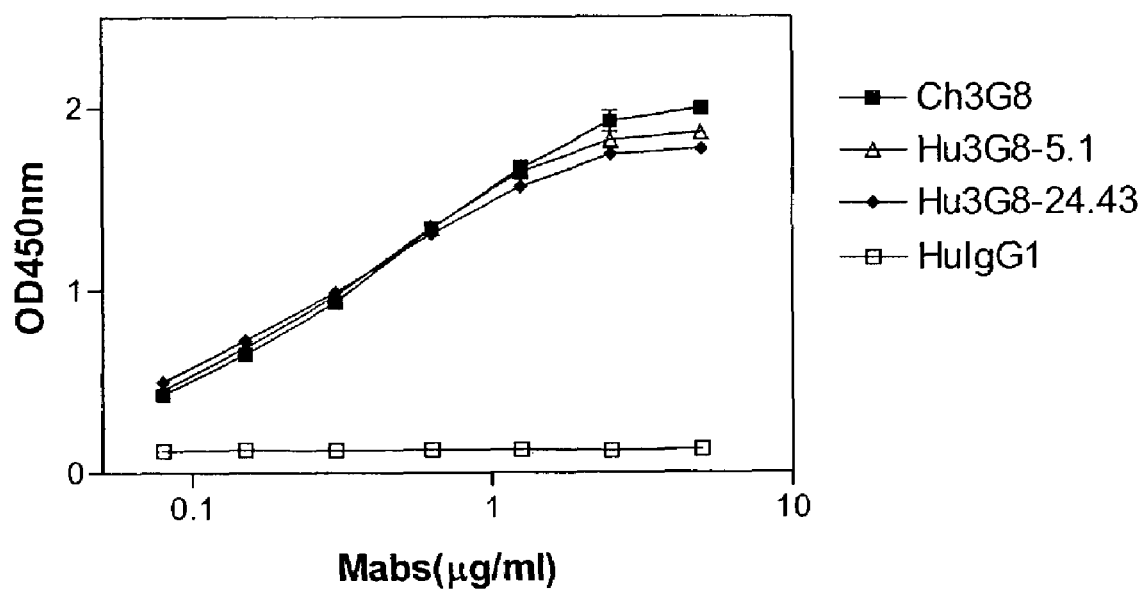
FIG. 1 shows results from an ELISA for binding of sCD16A by CD16A binding proteins. Hu3G8-24.43 is an antibody with the heavy chain Hu3G8VH-24, and the light chain Hu3G8VL-43. Hu3G8-5.1 is an antibody with the heavy chain Hu3G8VH-5, and the light chain Hu3G8VL-1. Ch3G8 is the chimeric 3G8 antibody. HuIgG1 is an irrelevant immunoglobulin.

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. The practice of the present invention will employ, unless otherwise indicated, conventional techniques of molecular biology (including recombinant techniques), microbiology, cell biology, biochemistry, nucleic acid chemistry, and immunology, which are within the skill of the art. Such techniques are explained fully in the literature, such as, *Current Protocols in Immunology* (J. E. Coligan et al., eds., 1999, including supplements through 2001); *Current Protocols in Molecular Biology* (F. M. Ausubel et al., eds., 1987, including supplements through 2001); *Molecular Cloning: A Laboratory Manual*, third edition (Sambrook and Russet, 2001); *PCR: The Polymerase Chain Reaction*, (Mullis et al., eds., 1994); *The Immunoassay Handbook* (D. Wild, ed., Stockton Press NY, 1994); *Bioconjugate Techniques* (Greg T. Hermanson, ed., Academic Press, 1996); *Methods of Immunological Analysis* (R. Masseyeff, W. H. Albert, and N. A. Staines, eds., Weinheim: VCH Verlags gesellschaft mbH, 1993); Harlow and Lane, *Using Antibodies: A Laboratory Manual*, Cold Spring Harbor Laboratory Press, Cold Spring Harbor, N.Y., 1999; and Beaucage et al. eds., *Current Protocols in Nucleic Acid Chemistry* John Wiley & Sons, Inc., New York, 2000).

The terms "heavy chain," "light chain," "variable region," "framework region," "constant domain," and the like, have their ordinary meaning in the immunology art and refer to domains in naturally occurring immunoglobulins and the corresponding domains of synthetic (e.g., recombinant) binding proteins (e.g., humanized antibodies). The basic structural unit of naturally occurring immunoglobulins (e.g., IgG) is a tetramer having two light chains and two heavy chains. Usually naturally occurring immunoglobulin is expressed as a glycoprotein of about 150,000 daltons, although, as described below, IgG can also be produced in a nonglycosylated form. The amino-terminal ("N") portion of each chain includes a variable region of about 100 to 110 or more amino acids primarily responsible for antigen recognition. The carboxy-terminal ("C") portion of each chain defines a constant region, with light chains having a single constant domain and heavy chains usually having three constant domains and a hinge region. Thus, the structure of the light chains of an IgG molecule is N-$V_L$-$C_L$-C and the structure of IgG heavy chains is N-$V_H$-$C_{H1}$-H-$C_{H2}$-$C_{H3}$-C (where H is the hinge region). The variable regions of an IgG molecule consist of the complementarity determining regions (CDRs), which contain the residues in contact with antigen and non-CDR segments, referred to as framework segments, which maintain the structure and determine the positioning of the CDR loops. Thus, the $V_L$ and $V_H$ domains have the structure N-FR1, CDR1, FR2, CDR2, FR3, CDR3, FR4-C.

As used herein, the terms "CD16A binding protein," "CD16A antibody," and "anti-CD16A antibody," are used interchangeably and refer to a variety of immunoglobulin-like or immunoglobulin-derived proteins. "CD16A binding proteins" bind CD16A via an interaction with $V_L$ and/or $V_H$ domains (as distinct from Fc-mediated binding). Examples of CD16A binding proteins include chimeric, humanized and human antibodies (e.g., comprising 2 heavy and 2 light chains), fragments thereof (e.g., Fab, Fab', F(ab')$_2$, and Fv fragments), bifunctional or multifunctional antibodies (see, e.g., Lanzavecchia et al., 1987, *Eur. J. Immunol.* 17:105), single chain antibodies (see, e.g., Bird et al., 1988, *Science* 242:423-26), fusion proteins (e.g., phage display fusion proteins), "minibodies" (see, e.g., U.S. Pat. No. 5,837,821) and other antigen binding proteins comprising a $V_L$ and/or $V_H$ domain or fragment thereof. In one aspect, the CD16A binding protein is a "tetrameric antibody," i.e., having generally the structure of a naturally occurring IgG and comprising both variable and constant domains, (i.e., two light chains comprising a $V_L$ domain and a light chain constant domain, such as human Cκ and two heavy chains comprising a $V_H$ domain and a heavy chain hinge and constant domains, such as human Cγ1). Except as expressly noted, the mouse antibody 3G8 is specifically excluded from the definition of CD16A binding protein.

When referring to binding proteins or antibodies (as broadly defined herein) the assignment of amino acids to each domain is in accordance with the definitions of Kabat, SEQUENCES OF PROTEINS OF IMMUNOLOGICAL INTEREST (National Institutes of Health, Bethesda, Md., 1987 and 1991). Amino acids from the variable regions of the mature heavy and light chains of immunoglobulins are designated by the position of an amino acid in the chain. Kabat described numerous amino acid sequences for antibodies, identified an amino acid consensus sequence for each subgroup, and assigned a residue number to each amino acid. Kabat's numbering scheme is extendible to antibodies not included in his compendium by aligning the antibody in question with one of the consensus sequences in Kabat by reference to conserved amino acids. This method for assigning residue numbers has become standard in the field and readily identifies amino acids at equivalent positions in different antibodies, including chimeric or humanized variants. For example, an amino acid at position 50 of a human antibody light chain occupies the equivalent position to an amino acid at position 50 of a mouse antibody light chain. Thus, as used herein in the context of chimeric or humanized antibodies, a reference such as "at position 297 of the Fc region" refers to the amino acid position in an immunoglobulin chain, region of an immunoglobulin chain, or region of a polypeptide derived from an immunoglobulin chain, that corresponds to position 297 of the corresponding human immunoglobulin.

The "Fc region" of immunoglobulins refers to the C-terminal region of an immunoglobulin heavy chain. Although the boundaries of the Fc region may vary somewhat, usually the Fc region is from about position 226-230 extending to the carboxy terminus of the polypeptide (and encompassing the $C_H2$ and $C_H3$ domains). Sequences of human Fc regions are found in Kabat, supra. In addition, a variety of allotypic variants are known to exist.

An "Fc effector ligand" is a ligand that binds to the Fc region of an IgG antibody, thereby activating effector mechanisms resulting in the clearance and destruction of pathogens. Fc effector ligands include three cellular Fc receptors types—FcRγI, FcRγII, and FcRγIII. The multiple isoforms of each of the three Fc receptor types are also included. Accordingly, the term "Fc effector ligand" includes both FcRγIIIA (CD16A) and FcRγIIIB (CD16B). The term "Fc effector ligand" also includes the neonatal Fc receptor (Fcγn) and the C1q component of complement. Binding of IgG to the Fc receptors triggers a variety of biological processes including antibody-dependent cell-mediated cytotoxicity (ADCC), release of inflammatory mediators, control of antibody production, clearance of immune complexes and destruction of antibody-coated particles. Binding of the C1q component of complement to IgG activates the complement system. Activation of complement plays important roles in opsonization, lysis of cell pathogens, and inflammatory responses.

As used herein, an Fc region that "lacks effector function" does not bind the Fc receptor and/or does not bind the C1q component of complement and trigger the biological responses characteristic of such binding.

The term "glycosylation site" refers to an amino acid residue that is recognized by a mammalian cell as a location for the attachment of sugar residues. Amino acid residues to which carbohydrates, such as oligosaccharides, are attached are usually asparagine (N-linkage), serine (O-linkage), and threonine (O-linkage) residues. The specific sites of attachment usually have a characteristic sequence of amino acids, referred to as a "glycosylation site sequence." The glycosylation site sequence for N-linked glycosylation is: -Asn-X-Ser- or -Asn-X-Thr-, where X can be any of the conventional amino acids, other than proline. The Fc region of human IgG has two glycosylation sites, one in each of the $C_H2$ domains. The glycosylation that occurs at the glycosylation site in the $C_H2$ domain of human IgG is N-linked glycosylation at the asparagine at position 297 (Asn 297).

The term "chimeric," when referring to antibodies, has the ordinary meaning in the art and refers to an antibody in which a portion of a heavy and/or light chain is identical to or homologous with an antibody from one species (e.g., mouse) while the remaining portion is identical to or homologous with an antibody of another species (e.g., human).

As used herein, the term "humanized" has its usual meaning in the art. In general terms, humanization of a non-human antibody involves substituting the CDR sequences from non-human immunoglobulin $V_L$ and $V_H$ regions into human framework regions. Further, as used herein, "humanized" antibodies may comprise additional substitutions and mutations in the CDR and/or framework regions introduced to increase affinity or for other purposes. For example, substitution of nonhuman framework residues in the human sequence can increase affinity. See, e.g., Jones et al., 1986, *Nature* 321:522-25; Queen et al., 1989, *Proc. Natl. Acad. Sci. U.S.A.* 86:10029-33; Foote and Winter, 1992, *J. Mol. Biol.* 224:487-99; Chothia et al., 1989, *Nature* 342:877-83; Riechmann et al., 1988, *Nature* 332:323-27; Co et al., 1991, *Proc. Natl. Acad. Sci. U.S.A.* 88:2869-73; Padlan, 1991, *Mol. Immunol* 28:489-98. The resulting variable domains have non-human CDR sequences and framework sequences derived from human antibody framework sequence(s) or a human consensus sequence (e.g., as disclosed in Kabat, supra). A variety of different human framework regions may be used singly or in combination as a basis for the humanized monoclonal antibodies of the present invention. The framework sequences of a humanized antibody are "substantially human," by which is meant that at least about 70% of the human antibody sequence, usually at least about 80% human, and most often at least about 90% of the framework sequence is from human antibody sequence. In some embodiments, the substantially human framework comprises a serine at position 113 of the $V_H$ FR4 domain (e.g., SEQ ID NO: 64). As used herein, a "humanized antibody" includes, in addition to tetrameric antibodies, single chain antibodies, antibody fragments and the like that comprise CDRs derived from a non-human antibody and framework sequences derived from human framework regions.

As used herein, "mammals" include humans, non-human primates, rodents, such as, mice and rats, and other mammals.

As used herein, "neutropenia" has its ordinary meaning, and refers to a state in which the number of neutrophils circulating in the blood is abnormally low. The normal level of neutrophils in human blood varies slightly by age and race. The average adult level is about 1500 cells/mm$^3$ of blood. Neutrophil counts less than 500 cells/mm$^3$ result in great risk of severe infection. Generally, in humans, severe neutropenia is defined by a blood neutrophil count less than about 500 cells/mm$^3$, and moderate neutropenia is characterized by a blood neutrophil count from about 500-1000 cells/mm$^3$.

As used herein, "treatment" refers to clinical intervention in an attempt to alter the disease course of the individual or cell being treated, and can be performed either for prophylaxis or during the course of clinical pathology. Therapeutic effects of treatment include without limitation, preventing occurrence or recurrence of disease, alleviation of symptoms, diminishment of any direct or indirect pathological consequences of the disease, decreasing the rate of disease progression, amelioration or palliation of the disease state, and remission or improved prognosis.

An "effective amount" is an amount sufficient to effect a beneficial or desired clinical result upon treatment. An effective amount can be administered to a patient in one or more doses. A "therapeutically effective amount" is an amount that is sufficient to palliate, ameliorate, stabilize, reverse or slow the progression of the disease, or otherwise reduce the pathological consequences of the disease, or reduce the symptoms of the disease. The amelioration or reduction need not be, and usually is not, permanent, but may be for a period of time ranging from at least one hour, at least one day, or at least on week or more. The effective amount is generally determined by the physician on a case-by-case basis and is within the skill of one in the art. Several factors are typically taken into account when determining an appropriate dosage to achieve an effective amount. These factors include age, sex and weight of the patient, the condition being treated, the severity of the condition and the form and effective concentration of the binding protein administered. An "inflammation reducing amount" is an amount that reduces inflammation in a subject. A reduction in inflammation can be assessed by art known criteria, including decreased C-reactive protein levels, decreased consumption of complement, reduced immune complex deposition at sites of inflammation (e.g., joints in subjects with RA, kidney in subjects with lupus, myelin sheath, etc.), reduced cytokine release, migration of macrophages and neutrophils, and the like.

"Substantial sequence identity," as used herein, refers to two or more sequences or subsequences (e.g., domains) that have at least about 80% amino acid residue identity, preferably at least about 90%, or at least about 95% identity when compared and aligned for maximum correspondence. Sequence identity between two similar sequences (e.g., antibody variable regions) can be measured by (1) aligning the sequences to maximize the total number of identities across the entire length of the sequences, or across the entire length of the shorter of the two sequences, if of different lengths (and where the length of the aligned sequences or shorter of the aligned sequences is "L" residues); (2) counting the number of positions (not including the number "E" residues designated as excluded from the comparison) at which there is an amino acid identity, where the number of identities is designated "N"; (3) and dividing the N by the "L" minus "E." For example, in a comparison of two sequences each of length 80 residues, in which 6 specific residues are excluded from the comparison and for which there are 65 identities in the remaining 74 positions, the sequence identity would be N/(L–E) or 65/(80–6) or 87.8%. (Residues might be specified as "excluded" from the calculation when, for illustration but not limitation, they are in a non-antibody domain of fusion protein.) Alternatively, optimal alignment and sequence identity can be calculated by computerized implementations of algorithms described in Smith & Waterman, 1981, *Adv. Appl. Math.* 2:482 [local homology algorithm], Needleman & Wunsch, 1970, *J. Mol. Biol.* 48:443 [homology alignment algorithm], Pearson & Lipman, 1988, *Proc. Natl. Acad. Sci. USA* 85:2444 [search for similarity method], or Altschul et al., 1990, *J. Mol. Biol.* 215:403-10 [BLAST algorithm]. See Ausubel et al., supra and GAP, BESTFIT, FASTA, and TFASTA in the Wisconsin Genetics Software Package, Genetics Computer Group, 575 Science Dr., Madison, Wis.). When using any of the aforementioned algorithms, the default parameters (for Window length, gap penalty, etc.) are used. An amino acid or nucleic acid sequence is "substantially similar to" a second sequence when the degree of sequence identity is at least about 70% identical, preferably at least about 80%, or at least about 90%, or even at least about 95%, identical. Sequences that are substantially identical are also substantially similar.

As used herein, a polypeptide, polypeptide domain or region, or amino acid sequence is "derived from" another when the two sequences are identical or substantially similar and have a similar biological function. For example, in a humanized mouse monoclonal antibody the complementary determining regions (CDRs) are "derived from" the corresponding CDRs of the mouse monoclonal antibody, and the variable domain framework regions can be "derived from" framework sequences of the corresponding human antibody. It will be apparent that one domain, etc., can be derived from a parental domain, etc., even though the two differ in sequence due to, for example, the introduction of mutations that affect, or alternatively do not change, binding affinity or other properties of the protein in which the domain, etc., is contained, such as those described herein. It will also be understood that normally a domain, etc., "derived from" a parental domain, etc., is made, produced or designed using materials (e.g. genetic material) or information (e.g., nucleotide or amino acid sequence) from the parental molecule.

Standard abbreviations are used for amino acids: alanine, Ala (A); serine, Ser (S); threonine, Thr (T); aspartic acid, Asp (D); glutamic acid, Glu (E); asparagine, Asn (N); glutamine, Gln (Q); arginine, Arg (R); lysine, Lys (K); isoleucine, Ile (I); leucine, Leu (L); methionine, Met (M); valine, Val (V); phenylalanine, Phe (F); tyrosine, Tyr (Y);

tryptophan, Trp (W); glycine, Gly (G); histidine, His (H); proline, Pro (P); and cysteine, Cys (C).

2. Introduction

The FcγRIIIA receptor, CD16A, plays a role in coupling cytotoxic and immune complex antibodies to effector responses. It is believed that the interaction of the FcγRIIIA receptor and immunoglobulin aggregates (e.g. immune complexes) present in autoimmune diseases and other pathogenic conditions results in a deleterious inflammatory response in subjects. Without intending to be bound by a specific mechanism, it is believed that reducing the interaction of the FcγRIIIA receptor (generally referred to herein as "CD16A" or "the CD16A receptor") and immunoglobulin aggregates will alleviate this inflammatory response. Also without intending to be bound by a specific mechanism, it is believed that one method for reducing the interaction of CD16A and immunoglobulin aggregates is by use of anti-CD16A antibodies, or other CD16A binding proteins, to block the interaction.

Monoclonal antibody 3G8 ("mAb 3G8") is a mouse monoclonal antibody that binds the Fc-binding domain of human CD16A and B with a $K_a$ of $1 \times 10^9$ $M^{-1}$ (Fleit et al., 1982, Proc. Natl. Acad. Sci. U.S.A 79:3275-79). 3G8 blocks the binding of human $IgG_1$ immune complexes to isolated human NK cells, monocytes and neutrophils, as well as to CD16A-transfected 293 cells. Experiments in which mAb 3G8 has been administered to human patients for treatment of idiopathic thrombocytopenic purpura (ITP) have been conducted (Clarkson et al., 1986, N. Engl. J Med. 314:1236-39; Soubrane, et al., 1993, Blood 81:15-19). Administration of the 3G8 antibody was reported to result in increased platelet levels and was accompanied by one or more significant side effects, including a HAMA response, cytokine release syndrome, and/or pronounced neutropenia.

The present invention provides novel CD16A binding proteins, including humanized and/or aglycosylated monoclonal antibodies, and methods for reducing a deleterious immune response in a subject by administering the proteins. Administration of these binding proteins is shown to be protective in well established models for two distinct autoimmune diseases: autoimmune hemolytic anemia (AHA) and idiopathic thrombocytopenic purpura. These results are indicative of efficacy of this treatment for other autoimmune diseases as well. Moreover, the inventors have discovered that, unexpectedly, administration of anti-CD16A antibodies with altered effector function (e.g., aglycosylated antibodies) protects against the deleterious immune reponses characteristic of autoimmune disorders without inducing acute severe neutropenia. Thus, the invention provides new reagents and methods for antibody-mediated effected treatment of autoimmune conditions without pronounced side-effects observed using alternative treatments.

3. CD16A Binding Proteins

A variety of CD16A binding proteins may be used in the methods of the invention. Suitable CD16A binding proteins include human or humanized monoclonal antibodies as well as CD16A binding antibody fragments (e.g., scFv or single chain antibodies, Fab fragments, minibodies) and another antibody-like proteins that bind to CD16A via an interaction with a light chain variable region domain, a heavy chain variable region domain, or both.

In some embodiments, the CD16A binding protein for use according to the invention comprises a $V_L$ and/or $V_H$ domain that has one or more CDRs with sequences derived from a non-human anti-CD16A antibody, such as a mouse anti-CD16A antibody, and one or more framework regions derived from framework sequences of one or more human immunoglobulins. A number of non-human anti-CD16A monoclonal antibodies, from which CDR and other sequences may be obtained, are known (see, e.g., Tamm and Schmidt, 1996, J. Imm. 157:1576-81; Fleit et al., 1989, p. 159; LEUKOCYTE TYPING II: HUMAN MYELOID AND HEMATOPOIETIC CELLS, Reinherz et al., eds. New York: Springer-Verlag; 1986; LEUCOCYTE TYPING III: WHITE CELL DIFFERENTIATION ANTIGENS, McMichael A J, ed., Oxford: Oxford University Press, 1986); LEUKOCYTE TYPING IV: WHITE CELL DIFFERENTIATION ANTIGENS, Kapp et al., eds. Oxford Univ. Press, Oxford; LEUKOCYTE TYPING V: WHITE CELL DIFFERENTIATION ANTIGENS, Schlossman et al., eds. Oxford Univ. Press, Oxford; LEUKOCYTE TYPING VI: WHITE CELL DIFFERENTIATION ANTIGENS, Kishimoto, ed. Taylor & Francis. In addition, as shown in the Examples, new CD16A binding proteins that recognize human CD16A expressed on cells can be obtained using well known methods for production and selection of monoclonal antibodies or related binding proteins (e.g., hybridoma technology, phage display, and the like). See, for example, O'Connel et al., 2002, J. Mol. Biol. 321:49-56; Hoogenboom and Chames, 2000, Imm. Today 21:371078; Krebs et al., 2001, J. Imm. Methods 254:67-84; and other references cited herein. Monoclonal antibodies from a non-human species can be chimerized or humanized using techniques of antibody humanization known in the art.

Alternatively, fully human antibodies against CD16A can be produced using transgenic animals having elements of a human immune system (see, e.g., U.S. Pat. Nos. 5,569,825 and 5,545,806), using human peripheral blood cells (Casali et al., 1986, Science 234:476), by screening a DNA library from human B cells according to the general protocol outlined by Huse et al., 1989, Science 246:1275, and by other methods.

It is contemplated that, for some purposes, it may be advantageous to use CD16A binding proteins that bind the CD16A receptor at the same epitope bound by 3G8, or at least sufficiently close to this epitope to block binding by 3G8. Methods for epitope mapping and competitive binding experiments to identify binding proteins with the desired binding properties are well known to those skilled in the art of experimental immunology. See, for example, Harlow and Lane, cited supra; Stahl et al., 1983, Methods in Enzymology 9:242-53; Kirkland et al., 1986, J. Immunol. 137:3614-19; Morel et al., 1988, Molec. Immunol. 25:7-15; Cheung et al., 1990, Virology 176:546-52; and Moldenhauer et al., 1990, Scand. J. Immunol. 32:77-82. Also see Examples and §3G (i), infra. For instance, it is possible to determine if two antibodies bind to the same site by using one of the antibodies to capture the antigen on an ELISA plate and then measuring the ability of the second antibody to bind to the captured antigen. Epitope comparison can also be achieved by labeling a first antibody, directly or indirectly, with an enzyme, radionuclide or fluorophore, and measuring the ability of an unlabeled second antibody to inhibit the binding of the first antibody to the antigen on cells, in solution, or on a solid phase.

It is also possible to measure the ability of antibodies to block the binding of the CD16A receptor to immune complexes formed on ELISA plates. Such immune complexes are formed by first coating the plate with an antigen such as fluorescein, then applying a specific anti-fluorescein antibody to the plate. This immune complex then serves as the ligand for soluble Fc receptors such as sFcRIIIa. Alternatively a soluble immune complex may be formed and labeled, directly or indirectly, with an enzyme radionuclide or fluorophore. The ability of antibodies to inhibit the binding of these labeled immune complexes to Fc receptors on cells, in solution or on a solid phase can then be measured.

CD16A binding proteins of the invention may or may not comprise a human immunoglobulin Fc region. Fc regions are not present, for example, in scFv binding proteins. Fc regions are present, for example, in human or humanized tetrameric monoclonal IgG antibodies. As described in detail below, in some embodiments of the present invention, the CD16A binding protein includes an Fc region that has an altered effector function, e.g., reduced affinity for an effector ligand such as an Fc receptor or C1 component of complement compared to the unaltered Fc region (e.g., Fc of naturally occurring $IgG_1$, proteins). In one embodiment the Fc region is not glycosylated at the Fc region amino acid corresponding to position 297. Such antibodies lack Fc effector function.

Thus, in some embodiments of the invention, the CD16A binding protein does not exhibit Fc-mediated binding to an effector ligand such as an Fc receptor or the C1 component of complement due to the absence of the Fc domain in the binding protein while, in other cases, the lack of binding or effector function is due to an alteration in the constant region of the antibody.

CD16A Binding Proteins Comprising CDR Sequences Similar to mAb 3G8 CDR Sequences CD16A binding proteins that can be used in the practice of the invention include proteins comprising a CDR sequence derived from (i.e., having a sequence the same as or similar to) the CDRs of the mouse monoclonal antibody 3G8. Complementary cDNAs encoding the heavy chain and light chain variable regions of the mouse 3G8 monoclonal antibody, including the CDR encoding sequences, were cloned and sequenced as described in the Examples. The nucleic acid and protein sequences of 3G8 are provided below and are designated SEQ ID NO:1 and 2 ($V_H$) and SEQ ID NO:3 and 4 ($V_L$). Using the mouse variable region and CDR sequences, a large number of chimeric and humanized monoclonal antibodies, comprising complementary determining regions derived from 3G8 CDRs were produced and their properties analyzed. To identify humanized antibodies that bind CD16A with high affinity and have other desirable properties, antibody heavy chains comprising a $V_H$ region with CDRs derived from 3G8 were produced and combined (by coexpression) with antibody light chains comprising a $V_L$ region with CDRs derived from 3G8 to produce a tetrameric antibody for analysis. Properties of the resulting tetrameric antibodies were determined as described below. As described below, CD16A binding proteins comprising 3G8 CDRs, such as the humanized antibody proteins described hereinbelow, may be used according to the invention to reduce an deleterious immune response.

A. $V_H$ Region

In one aspect, the CD16A binding protein of the invention may comprise a heavy chain variable domain in which at least one CDR (and usually three CDRS) have the sequence of a CDR (and more typically all three CDRS) of the mouse monoclonal antibody 3G8 heavy chain and for which the remaining portions of the binding protein are substantially human (derived from and substantially similar to, the heavy chain variable region of a human antibody or antibodies).

In an aspect, the invention provides a humanized 3G8 antibody or antibody fragment containing CDRs derived from the 3G8 antibody in a substantially human framework, but in which at least one of the CDRs of the heavy chain variable domain differs in sequence from the corresponding mouse antibody 3G8 heavy chain CDR. For example, in one embodiment, the CDR(S) differs from the 3G8 CDR sequence at least by having one or more CDR substitutions shown in Table 1 (e.g., valine at position 34 in CDR1, leucine at position 50 in CDR2, phenylalanine at position 52 in CDR2, tyrosine at position 52 in CDR2, aspartic acid at position 52 in CDR2, asparagine at position 54 in CDR2, serine at position 60 in CDR2, serine at position 62 in CDR2, tyrosine at position 99 in CDR3, and/or aspartic acid at position 101 of CDR3). Suitable CD16 binding proteins may comprise 0, 1, 2, 3, or 4, or more of these substitutions (and often have from 1 to 4 of these substitutions) and optionally can have additional substitutions as well.

In one embodiment, a CD16A binding protein may comprise a heavy chain variable domain sequence that is the same as, or similar to, the $V_H$ domain of the Hu3G8VH-1 construct, the sequence of which is provided in Table 3. For example, the invention provides a CD16A binding protein comprising a $V_H$ domain with a sequence that (1) differs from the $V_H$ domain of Hu3G8VH-1 by zero, one, or more than one of the CDR substitutions set forth in Table 1; (2) differs from the $V_H$ domain of Hu3G8VH-1 by zero, one or more than one of the framework substitutions set forth in Table 1; and (3) is at least about 80% identical, often at least about 90%, and sometimes at least about 95% identical, or even at least about 98% identical to the Hu3G8VH-1 $V_H$ sequence at the remaining positions.

Exemplary $V_H$ domains of CD16 binding proteins of the invention have the sequence of Hu3G8VH-5 and Hu3G8VH-22, as shown in Tables 3 and 6.

The $V_H$ domain may have a sequence that differs from that of Hu3G8VH-1 (Table 3) by at least one, at least two, at least three, at least four, at least five, or at least six of the substitutions shown in Table 1. These substitutions are believed to result in increased affinity for CD16A and/or reduce the immunogenicity of a CD16A binding protein when administered to humans. In certain embodiments, the degree of sequence identity with the Hu3G8VH-1 $V_H$ domain at the remaining positions is at least about 80%, at least about 90%, at least about 95% or at least about 98%.

TABLE 1

$V_H$ Domain Substitutions

| No. | Kabat Position | Region | Substitutions |
| --- | --- | --- | --- |
| 1 | 2 | FR1 | Ile |
| 2 | 5 | FR1 | Lys |
| 3 | 10 | FR1 | Thr |
| 4 | 30 | FR1 | Arg |
| 5 | 34 | CDR1 | Val |
| 6 | 50 | CDR2 | Leu |
| 7 | 52 | CDR2 | Phe or Tyr or Asp |
| 8 | 54 | CDR2 | Asn |
| 9 | 60 | CDR2 | Ser |
| 10 | 62 | CDR2 | Ser |
| 11 | 70 | FR3 | Thr |
| 12 | 94 | FR3 | Gln or Lys or Ala or His |
| 13 | 99 | CDR3 | Tyr |
| 14 | 101 | CDR3 | Asp |

For illustration and not limitation, the sequences of a number of CD16A building protein $V_H$ domains are shown in Table 3. As described in the Examples, infra, heavy chains comprising these sequences fused to a human Cγ1 constant region were coexpressed with the hu3G8VL-1 light chain (described below) to form tetrameric antibodies, and binding of the antibodies to CD16A was measured to assess the effect of amino acid substitutions compared to the hu3G8VH-1 $V_H$ domain. Constructs in which the $V_H$ domain has a sequence of hu3G8VH-1, 2, 3, 4, 5, 8, 12, 14, 16, 17, 18, 19, 20, 22, 23, 24, 25, 26, 27, 28, 29, 30, 31, 32, 33, 34, 35, 36, 37, 42, 43, 44 and 45 showed high affinity binding, with hu3G8VH-6 and -40 $V_H$ domains showing intermediate binding. CD16A binding proteins comprising the $V_H$ domains of hu3G8VH-5 and hu3G8VH-22 are considered to have particularly favorable binding properties.

B. $V_L$ Region

Similar studies were conducted to identify light chain variable domain sequences with favorable binding properties. In one aspect, the invention provides a CD16A binding protein containing a light chain variable domain in which at least one CDR (and usually three CDRs) has the sequence of a CDR (and more typically all three CDRs) of the mouse monoclonal antibody 3G8 light chain and for which the remaining portions of the binding protein are substantially human (derived from and substantially similar to, the heavy chain variable region of a human antibody or antibodies).

In one aspect, the invention provides a humanized 3G8 antibody or antibody fragment containing CDRs derived from the 3G8 antibody in a substantially human framework, but in which at least one of the CDRs of the light chain variable domain differs in sequence from the mouse monoclonal antibody 3G8 light chain CDR. In one embodiment, the CDR(s) differs from the 3G8 sequence at least by having one or more amino acid substitutions in a CDR, such as, one or more substitutions shown in Table 2 (e.g., arginine at position 24 in CDR1; serine at position 25 in CDR1; tyrosine at position 32 in CDR1; leucine at position 33 in CDR1; aspartic acid, tryptophan or serine at position 50 in CDR2; serine at position 53 in CDR2; alanine or glutamine at position 55 in CDR2; threonine at position 56 in CDR2; serine at position 93 in CDR3; and/or threonine at position 94 in CDR3). In various embodiments, the variable domain can have 0, 1, 2, 3, 4, 5, or more of these substitutions (and often have from 1 to 4 of these substitutions) and optionally, can have additional substitutions as well.

In one embodiment, a suitable CD16A binding protein may comprise a light chain variable domain sequence that is the same as, or similar to, the $V_L$ domain of the Hu3G8VL-1 construct, the sequence of which is provided in Table 4. For example, the invention provides a CD16A binding protein comprising a $V_L$ domain with a sequence that (1) differs from the $V_L$ domain of Hu3G8VL-1 by zero, one, or more of the CDR substitutions set forth in Table 2; (2) differs from the $V_L$ domain of Hu3G8VL-1 by zero, one or more of the framework substitutions set forth in Table 2; and (3) is at least about 80% identical, often at least about 90%, and sometimes at least about 95% identical, or even at least about 98% identical to the Hu3G8VL-1 $V_L$ sequence at the remaining positions.

Exemplary $V_L$ domains of CD16 binding proteins of the invention have the sequence of Hu3G8VL-1 or Hu3G8VL-43, as shown in Tables 4 and 6.

The $V_L$ domain may have a sequence that differs from that of Hu3G8VL-1 (Table 4) by zero, one, at least two, at least 3, at least 4, at least 5, at least 6, at least 7, at least 8, or at least 9 of the substitutions shown in Table 2. These substitutions are believed to result in increased affinity for CD16A and/or reduce the immunogenicity of a CD16A binding protein when administered to humans. In certain embodiments, the degree of sequence identity at the remaining positions is at least about 80%, at least about 90% at least about 95% or at least about 98%.

TABLE 2

$V_L$ Domain Substitutions

| No. | Kabat Position | Region | Substitutions |
|---|---|---|---|
| 1 | 24 | CDR1 | Arg |
| 2 | 25 | CDR1 | Ser |
| 3 | 32 | CDR1 | Tyr |
| 4 | 33 | CDR1 | Leu |
| 5 | 50 | CDR2 | Asp or Trp or Ser |
| 6 | 51 | CDR2 | Ala |
| 7 | 53 | CDR2 | Ser |
| 8 | 55 | CDR2 | Ala or Gln |
| 9 | 56 | CDR2 | Thr |
| 10 | 93 | CDR3 | Ser |
| 11 | 94 | CDR3 | Thr |

For illustration and not limitation, the sequences of a number of CD16A binding proteins $V_L$ domains are shown in Table 4. As described in the Examples, infra, light chains comprising these sequences fused to a human CK constant domain were coexpressed with the Hu3G8VH-1 heavy chain (described above) to form tetrameric antibodies, and the binding of the antibodies to CD16A was measured to assess the effect of amino acid substitutions compared to the Hu3G8VL-1 $V_L$ domain. Constructs in which the $V_L$ domain has a sequence of hu3G8VL-1, 2, 3, 4, 5, 10, 16, 18, 19, 21, 22, 24, 27, 28, 32, 33, 34, 35, 36, 37, and 42 showed high affinity binding and hu3G8VL-15, 17, 20, 23, 25, 26, 29, 30, 31, 38, 39, 40 and 41 showed intermediate binding. CD16A binding proteins comprising the $V_L$ domains of hu3G8VL-1, hu3G8VL-22, and hu3G8VL-43 are considered to have particularly favorable binding properties.

C. Combinations of $V_L$ and/or $V_H$ Domains

As is known in the art and described elsewhere herein, immunoglobulin light and heavy chains can be recombinantly expressed under conditions in which they associate to produce a tetrameric antibody, or can be so combined in vitro. Similarly, combinations of $V_L$ and/or $V_H$ domains can be expressed in the form of single chain antibodies, and still other CD16A binding proteins that comprise a $V_L$ and/or $V_H$ domain can be expressed by known methods. It will thus be appreciated that a 3G8-derived $V_L$-domain described herein can be combined with a 3G8-derived $V_H$-domain described herein to produce a CD16A binding protein, and all such combinations are contemplated.

For illustration and not for limitation, examples of useful CD16A binding proteins are those comprising at least one $V_H$ domain and at least one $V_L$ domain, where the $V_H$ domain is from hu3G8VH-1, hu3G8VH-22 or hu3G8VH-5 and the $V_L$ domain is from hu3G8VL-1, hu3G8VL-22 or hu3G8VL-43. In particular, humanized antibodies that comprise hu3G8VH-22 and either hu3G8VL-1, hu3G8VL-22 or hu3G8VL-43, or hu3G8VH-5 and hu3G8VL-1 have favorable properties.

It will be appreciated by those of skill that the sequences of $V_L$ and $V_H$ domains described here can be further modified by art-known methods such as affinity maturation (see Schier et al., 1996, *J. Mol. Biol.* 263:551-67; Daugherty et al., 1998, *Protein Eng.* 11:825-32; Boder et al., 1997, *Nat. Biotechnol.* 15:553-57; Boder et al., 2000, *Proc. Natl. Acad. Sci. U.S.A* 97:10701-705; Hudson and Souriau, 2003, *Nature Medicine* 9:129-39). For example, the CD16A binding proteins can be modified using affinity maturation techniques to identify proteins with increased affinity for CD16A and/or decreased affinity for CD16B.

D. Constant Domains and Fc Region

As noted above, the CD16A binding protein of the invention may contain light chain and/or heavy chain constant regions (including the hinge region connecting the $C_{H1}$ and $C_{H2}$ domains in IgG molecules). It is contemplated that a constant domain from any type (e.g., IgM, IgG, IgD, IgA and IgE) of immunoglobulin may be used. The constant domain for the light chain can be lambda or kappa. The constant domain for the heavy chain can be any isotype (e.g., $IgG_1$, $IgG_2$, $IgG_3$ and $IgG_4$). Chimeric constant domains, portions of constant domains, and variants of naturally occurring human antibody constant domains (containing deletions, insertions or substitutions of amino acid residues) may be used. For instance, a change in the amino acid sequence of a constant domain can be modified to provide additional or different properties, such as altered immunogenicity or half-life of the resultant polypeptide. The changes range from insertion, deletion or substitution of a small number (e.g., less than ten, e.g., one, two, three or more) amino acid residues to substantial modifications of the constant region domain. Changes contemplated include those that affect the interaction with membrane receptors, complement fixation, persistence in circulation, and other effector functions. For example, the hinge or other regions can be modified as described in U.S. Pat. No. 6,277,375. In particular, it will often be advantageous to delete or alter amino acids of the Fc region. For example, the Fc region can be modified to reduce or eliminate binding to Fc effector ligands such as FcγRIII and the C1q component of complement, such that the antibodies lack (or have substantially reduced) effector function. Antibodies having such modified Fc regions induce little or no antibody dependent cellular cytotoxicity (ADCC) and/or complement mediated lysis when administered to a mammal, compared to unmodified antibodies. Assays to identify antibodies lacking effector function are known in the art. See, e.g., U.S. Pat. Nos. 6,194,551; 6,528,624; and 5,624,821, European Pat. No. EP 0 753 065 B1, and PCT publication WO 00/42072.

The CD16A binding protein of the invention may include a human $IgG_1$ Fc domain comprising one or more amino acid substitutions or deletions (relative to the parental naturally occurring $IgG_1$) that result in a reduced interaction between the Fc domain of the binding protein and FcγRIIA and/or FcγRIIIA (e.g., to minimize potential activation of macrophages and/or minimize neutrophil diminution) and/or increased binding of the Fc region to FcγRIIB (e.g., to increase FcγRIIB-mediated inhibition of effector cell activation; see Bolland and Ravetch, 1999, *Adv. in Immunol.* 72:149). Specific mutations effecting the desired changes in binding can be identified by selection using display of mutant Fc libraries expressed on the surface of microorganisms, viruses or mammalian cells, and screening such libraries for mutant Fc variants having the desired property or properties. In addition, the literature reports that particular residues or regions of the Fc are involved in Fcγ interactions such that deletion or mutation of these residues would be expected to result in reduced FcR binding. The binding site on human antibodies for FcγR was reported to be the residues 233-239 (Canfield et al., 1991, *J Exp Med* 173: 1483-91; Woof et al., 1986, *Mol. Imm.* 23:319-30; Duncan et al., 1988, *Nature* 332:563). The crystal structure of FcγRIII complexed with human IgG1 Fc revealed potential contacts between the receptor and its ligand and also revealed that a single FcγRIII monomer binds to both subunits of the Fc homodimer in an asymmetric fashion. Alanine-scanning mutagenesis of the Fc region confirmed the importance of most of the predicted contact residues (Shields et al., 2001, *J Biol. Chem.* 276:6591-6604).

Exemplary Fc region mutations include, for example, L235E, L234A, L235A, and D265A, which have been shown to have low affinity for all FcR, into Cγ-1 (Clynes et al., 2000, *Nat. Med.* 6:443-46; Alegre et al., 1992, *J Immunol* 148:3461-68; Xu et al., 2000, *Cell Immunol* 200:16-26). Additional Fc region modifications purported to affect FcR binding are described in WO 00/42072 (e.g., "class 4" Fc region variants) and WO 02/061090.

Fc binding to FcγRIIA and FcγIIIA or other proteins can be measured by any of a number of methods, including ELISA to measure binding to isolated recombinant FcγR and RIA or FACS to measure binding to cells. Immune complexes and heat aggregated or chemically crosslinked Fc or IgG can be used to test affinity for FcRs in such assays. In one embodiment, immune complexes are produced by expressing an Fc in the context of an Fab with affinity for an antigen (such as fluorescein) and mixing the antibody and antigen to form an immune complex.

E. Fc Regions with Reduced Binding to Fc Effector Ligands Due to Aglycosylation or Changes in Glycosylation As discussed above, in CD16A binding proteins of the invention that comprise Fc domains (e.g., anti-CD16A monoclonal antibodies) the Fc domain can be modified to achieve desired properties. In a particular aspect, the invention provides a CD16A binding protein, such as a human or humanized anti-CD16A monoclonal antibody, comprising an Fc region that is not glycosylated. As demonstrated in Example 10, infra, the inventors have discovered that, unexpectedly, administration of anti-CD16A antibodies with altered effector function (aglycosylated antibodies) protects against autoimmune disorders without inducing acute severe neutropenia. On the basis of this discovery, therapeutic anti-CD16A antibodies can be designed to protect against autoimmune diseases without inducing dangerous side effects.

In one embodiment, the invention provides a CD16A binding protein comprising an Fc region derived from human $IgG_1$, where the amino acids corresponding to position 297 of the $C_H2$ domains of the Fc region are aglycosyl. The terms "aglycosyl" or "aglycosylated," when referring to an Fc region in its entirety, or a specific amino acid residue in the Fc region, mean that no carbohydrate residues are attached to the specified region or residue.

Human IgG antibodies that are aglycosylated show decreased binding to Fc effector ligands such as Fc receptors and C1q (see, e.g., Jefferis et al., 1995, *Immunology Letters* 44:111-17; Tao, 1989, *J. of Immunology*, 143:2595-2601; Friend et al., 1999, *Transplantation* 68:1632-37; Radaev and Sun, 2001, *J. of Biological Chemistry* 276:16478-83; Shields et al., 2001, *J. of Biological Chemistry* 276:6591-6604, and U.S. Pat. No. 5,624,821). Without intending to be bound by a particular mechanism, it is believed that the aglycosylation of the amino acid at position 297 of the Fc domains of CD16A binding proteins described herein results in reduced binding to CD16A and the C1q component of complement. Such aglycosylated antibodies lack effector function.

In human IgG$_1$ constant regions, the residue at position 297 is asparagine. In one embodiment of the present invention, the residue at, or corresponding to, position 297 of the Fc region of the CD16A binding protein is other than asparagine. Substitution of another amino acid residue in the place of asparagine eliminates the N-glycosylation site at position 297. Substitution of any amino acid residues which will not result in glycosylation upon expression of the CD16A binding protein in a mammalian cell is appropriate for this embodiment. For instance, in some embodiments of the invention, the amino acid residue at position 297 is glutamine or alanine. In some embodiments, the amino acid residue at position 297 is cysteine, which is optionally linked to PEG.

In other embodiments of the invention, the residue at position 297 may or may not be asparagine, but is not glycosylated. This can be accomplished in a variety of ways. For example, amino acid residues other than the asparagine at position 297 are known to be important for N-linked glycosylation at position 297 (see Jefferis and Lund, 1997, *Chem. Immunol.* 65:111-28), and the substitution of residues at positions other than position 297 of the $C_H2$ domain can result in a CD16A binding protein aglycosylated at residue 297. For illustration and not limitation, a residue at position 299 in the $C_H2$ domain that is other than threonine or serine will result in an antibody that is aglycosylated at position 297. Similarly, substitution of the amino acid at position 298 with proline will produce an antibody with an aglycosylated amino acid at position 297. In other embodiments of the invention, Fc domains of IgG$_2$ or IgG$_4$ are used rather than IgG$_1$ domains.

Modification of the amino acid residues of CD16A binding proteins is well within the ability of the ordinarily skilled practitioner, and can be achieved by mutation of a polynucleotide encoding the binding protein or portion thereof. The CD16A binding protein comprising an IgG-derived Fc region need not necessarily be mutated at the amino acid level to be aglycosylated. Binding proteins aglycosylated at position 297 of the IgG-derived Fc region can be produced by expressing the CD16A binding protein in certain cells (e.g., *E. coli*; see PCT publication WO 02061090A2), cell lines or under certain cell culture growth conditions where glycosylation at Asn 297 does not take place. Alternatively, carbohydrate groups may be removed from a CD16A binding protein following expression of the protein, e.g., enzymatically. Methods for removing or modifying carbohydrate groups on proteins are known and include use of endoglycosidases and peptide:N-glycosidases.

It will be apparent that a variety of methods can be used to modify the Fc region of a CD16A binding protein to change its properties. Accordingly, unless otherwise specified, as used herein the term "modifying" in the context of modifying the Fc region of a CD16A binding protein includes modifying the protein itself directly, modifying the polynucleotide that encodes the protein and/or modifying or selecting a suitable expression system for production of the protein.

In addition to CD16A binding proteins that are aglycosylated at the position corresponding to arginine 297, variants with reduced binding to Fc effector ligands due to only partial removal, or modification, of the carbohydrate at that position may be used in the present invention. For example, the Fc region can be modified to include a non-naturally occurring carbohydrate that does not bestow binding protein with effector function. As used herein, a "modified Fc region" is an Fc region that has been derived from a parent Fc region, but which differs in glycosylation pattern from the parent Fc region.

F. Production of CD16A Binding Proteins

CD16A binding proteins of the invention can be produced using a variety of methods well known in the art, including de novo protein synthesis and recombinant expression of nucleic acids encoding the binding proteins. The desired nucleic acid sequences can be produced by recombinant methods (e.g., PCR mutagenesis of an earlier prepared variant of the desired polynucleotide) or by solid-phase DNA synthesis. Usually recombinant expression methods are used. In one aspect, the invention provides a polynucleotide that comprises a sequence encoding a CD16A binding protein disclosed herein or a CD16A binding fragment thereof, for example a sequence encoding a $V_L$ or $V_H$ described herein, or antibody heavy chain or light chain described herein. Because of the degeneracy of the genetic code, a variety of nucleic acid sequences encode each immunoglobulin amino acid sequence, and the present invention includes all nucleic acids encoding the binding proteins described herein.

Recombinant expression of antibodies is well known in the art and can be carried out, for example, by inserting nucleic acids encoding light and heavy chain variable regions, optionally linked to constant regions, into expression vectors. Expression vectors typically include control sequences such as a promoter, an enhancer, and a transcription termination sequence to which DNA segments encoding polypeptides (e.g., immunoglobulin chains) are operably linked to ensure the expression of immunoglobulin polypeptides. Expression vectors are typically replicable in the host organisms either as episomes or as an integral part of the host chromosomal DNA. The light and heavy chains can be cloned in the same or different expression vectors.

Immunoglobulin light and heavy chains are expressed using standard methods. A multiple polypeptide chain antibody or antibody fragment species can be made in a single host cell expression system wherein the host cell produces each chain of the antibody or antibody fragment and assembles the polypeptide chains into a multimeric structure to form the antibody or antibody fragment in vivo. See e.g., Lucas et al., 1996, *Nucleic Acids Res.,* 24:1774-79. When heavy and light chains are cloned on separate expression vectors, the vectors are co-transfected to obtain expression and assembly of intact immunoglobulins. Alternatively, recombinant production of antibody heavy and light chains in separate expression hosts followed by assembly of antibody from separate heavy and light chains in vitro is known. See, e.g., U.S. Pat. No. 4,816,567 and Carter et al., 1992, *Bio/Technology* 10:163-67.

The CD16A binding proteins are conveniently expressed in prokaryotic or eukaryotic cells. Useful hosts for antibody expression include bacteria (see, e.g., PCT publication WO 02/061090), yeast (e.g., *Saccharomyces*), insect cell culture (Putlitz et al., 1990, *Bio/Technology* 8:651-54), plants and plant cell cultures (Larrick and Fry, 1991, *Hum. Antibodies Hybridomas* 2:172-89), and mammalian cells. Methods for expression are well known in the art. For example, in *E. coli*, vectors using the lac promoter to drive expression of heavy and light chains fused to various prokaryotic secretion signal sequences such as pelB have resulted in successful secretion of scFv and Fab fragments into the periplasmic space or into the culture medium (Barbas et al., 1991, *Proc. Natl. Acad.*

Sci. U.S.A. 88:7978-82). A vector derived from pET25b in which the lac promoter has been inserted in place of the T7 promoter may be used.

Mammalian cells are especially useful for producing CD16A binding proteins, including tetrameric antibodies or fragments thereof. A number of suitable host cell lines capable of secreting intact heterologous proteins are known, and include CHO cell lines, COS cell lines, HeLa cells, L cells and myeloma cell lines. Expression vectors for mammalian cells can include expression control sequences, such as an origin of replication, a promoter, an enhancer, ribosome binding sites, RNA splice sites, polyadenylation sites, and transcriptional terminator sequences. Examples of expression control sequences are promoters derived from endogenous genes, cytomegalovirus, SV40, adenovirus, bovine papillomavirus, and the like. In one embodiment, binding proteins are expressed using the CMV immediate early enhancer/promoter in the vector pCDNA3.1 or a similar vector. To facilitate secretion, the genes can be fused to a gene cassette containing the signal sequence of a mouse VH gene described by Orlandi et al., 1989, *Proc. Natl. Acad. Sci. U.S.A* 86:3833-37, which has been widely used for high-level secretion of immunoglobulins.

The vectors containing the DNA segments encoding the polypeptides of interest can be transferred into the host cell using routine methods, depending on the type of cellular host. For example, calcium chloride transfection is commonly utilized for prokaryotic cells, whereas calcium phosphate treatment, electroporation, lipofection, biolistics or viral-based transfection may be used for other cellular hosts. Other methods used to transform mammalian cells include the use of polybrene, protoplast fusion, liposomes, electroporation, and microinjection (see generally, Sambrook et al., supra). For transient expression, cells, e.g., HEK293, can be co-transfected with separate heavy and light chain expression vectors using a cationic lipid (e.g., LIPO-FECTAMINE™ 2000, Invitrogen). This method can achieve expression levels of 10-20 mg/l of IgG in conditioned medium after 3 days. The cells can then be re-fed and similar quantities harvested after 3 more days. It will be appreciated that, for some uses, the cells expressing CD16A binding proteins can be maintained in medium containing FBS screened for very low levels of bovine IgG, or, alternatively, in serum-free medium.

In addition to expression of tetrameric antibodies, single chain antibodies, antibody fragments, and other CD16A binding proteins can be prepared. For example, immunoglobulin fragments can be prepared by proteolytic digestion of tetrameric antibodies, or more often, by recombinant expression of truncated antibody constructs. Usually, single chain V region ("scFv") constructs are made by linking $V_L$ and/or $V_H$ domain using a short linking peptide (see, e.g., Bird et al., 1988, *Science* 242:423-26; U.S. Pat. Nos. 4,946, 778; 5,455,030; 6,103,889; and 6,207,804).

Once expressed, the binding proteins can be purified using procedures well known in the art, including ammonium sulfate precipitation, affinity chromatography, gel electrophoresis and the like (see, generally, Harris and Angal, 1990, PROTEIN PURIFICATION APPLICATIONS, A PRACTICAL APPROACH Oxford University Press, Oxford, UK; and Coligan et al., supra). In one embodiment, purification is accomplished by capturing the antibody using a high flow rate protein A resin such as Poros A (Perseptive Biosystems, Inc), and elution at low pH, followed by size exclusion chromatography to remove any traces of aggregate present. Since FcγRIIIA binds preferentially to aggregated IgG, removal of aggregates will be desirable for certain applications. The binding proteins can be purified to substantial purity if desired, e.g., at least about 80% pure, often at least about 90% pure, more often least about 95%, or at least about 98% pure. In this context, the percent purity is calculated as a weight percent of the total protein content of the preparation, and does not include constituents which are deliberately added to the composition after the binding protein is purified.

CD16A binding proteins can be modified after expression. For example, derivation of antibodies with polyethylene glycol ("pegylation") is reported to increase residence time (half-life and stability) and reduce immunogenicity in vivo without alteration of biological activity. See, e.g., Leong et al., 2001, *Cytokine* 16:106-19; Koumenis et al., 2000, *Int J Pharm* 198:83-95; U.S. Pat. No. 6,025,158. CD16A binding proteins can be conjugated to a detectable label or ligand (e.g., a radioisotope or biotin). Other modifications are well known in the art and are also contemplated.

G. Properties of CD16A Binding Proteins

In certain embodiments, CD16A binding proteins having properties as described below are used in the methods of the invention.

i) Binding Affinity

CD16A binding proteins can be described by reference to their binding properties and biological activity. In various embodiments, the binding constant for the interaction of a CD16A binding protein of the invention and CD16A is between 0.1 and 5 nM, less than about 2.5 nM, less than about 1 nM, or less than about 0.5 nM. Usually the binding protein binds CD16A with an affinity that is within 4-fold, optionally within 2-fold, of the binding affinity exhibited under similar conditions by 3G8 or the chimeric antibody comprising the heavy chain Ch3G8VH and the light chain Ch3G8VL as described herein below. In an embodiment, the binding affinity for CD16A is greater than that of 3G8. In an alternative embodiment, the binding affinity for CD16B is no greater than, and preferably less than, 3G8 or the chimeric antibody Ch3G8.

Binding can be measured using a variety of methods, including ELISA, biosensor (kinetic analysis), and radioimmunoassay (RIA). ELISA is well known (see, Harlow and Lane, supra, and Ausubel et al., supra) and can be carried out using conditioned medium containing binding proteins or, alternatively, with purified antibodies. The concentration of antibody that results in 50% apparent maximal binding provides an estimate of antibody Kd.

Binding can also be detected using a biosensor assay, which also provides information on the kinetic and equilibrium properties of antibody binding to FcγRIIIA. An exemplary biosensor assay uses the BIAcore system (Malmqvist et al., 1997, *Curr. Opin. Chem. Biol.* 1:378-83). The BIAcore system relies on passing analyte over a sensor chip onto which the ligand (e.g., CD16A) is immobilized. The binding of the analyte can be measured by following surface plasmon resonance (SPR) signal, which changes in direct proportion to the mass bound to the chip. A fixed concentration of analyte is passed over the chip for a specific amount of time, allowing for the measurement of the association rate, k(on). Following this phase, buffer alone is passed over the chip and the rate at which the analyte dissociates from the surface, k(off) can be measured. The equilibrium dissociation constant can be calculated from the ratio of the kinetic constants; Kd=k(on)/k(off).

A radioimmunoassay (RIA) can be used to measure the affinity of antibodies for FcγRIII-bearing cells, and to measure inhibition of IgG complexes to cells by these antibodies. In an exemplary assay, $^{125}$I labeled binding protein is prepared and specific radioactivity of the protein determined. Labeled binding protein and cells are mixed for several hours, the cells and bound material are separated from the unbound material by centrifugation, and the radioactivity in both compartments is determined. A direct binding format is used to determine the Kd of, and the number of binding sites for, iodinated binding protein using Scatchard analysis of the binding data. Controls containing an excess of cold (unlabeled) binding protein competitor can be included to ensure the results reflect specific interactions. Examples of suitable cells include (1) NK cells or macrophages derived from normal human peripheral blood lymphocytes; (2) Cells obtained from huCD16A transgenic mice (Li, 1996 *J. Exp. Med.* 183:1259-63); (3) mammalian cell lines expressing the extracellular portion of CD16A fused to the transmembrane and intracellular domain of RII or another receptor (such as CD8 or LFA-3); (4) mammalian cell lines (e.g., CHO, HEK-293, COS) transfected transiently or stably with CD16A expression vectors (and optionally coexpressing gamma chain for optimal expression receptor expression).

Examples of expression vectors useful for expression of CD16A and other polypeptides for use in binding assays include mammalian expression vectors (e.g., pCDNA 3.1 or pCI-neo) that contain a strong promoter/enhancer sequence (e.g., CMV immediate early) and a polyadenylation/transcription termination site flanking a polylinker region into which the CD16A gene is introduced. Usually the vector includes a selectable marker such as a neomycin resistance gene.

In one embodiment, the CD16A expressed for use in assays has the sequence:

(SEQ ID NO:116)
MWQLLLPTALLLLVSAGMRTEDLPKAVVFLEPQWYRVLEKDSVTLKCQGA

YSPEDNSTQWFHNESLISSQASSYFIDAATVDDSGEYRCQTNLSTLSDPV

QLEVHIGWLLLQAPRWVFKEEDPIHLRCHSWKNTALHKVTYLQNGKGRKY

FHHNSDFYIPKATLKDSGSYFCRGLFGSKNVSSETVNITITQGLAVSTIS

SFFPPGYQVSFCLVMVLLFAVDTGLYFSVKTNIRSSTRDWKDHKFKWRKD

PQDK.

CD16A with the sequence:

(SEQ ID NO:117)
MWQLLLPTALLLLVSAGMRTEDLPKAVVFLEPQWYRVLEKDSVTLKCQGA

YSPEDNSTQWFHNESLISSQASSYFIDAATVDDSGEYRCQTNLSTLSDPV

QLEVHIGWLLLQAPRWVFKEEDPIHLRCHSWKNTALHKVTYLQNGKGRKY

FHHNSDFYIPKATLKDSGSYFCRGLVGSKNVSSETVNITITQGLAVSTIS

SFFPPGYQVSFCLVMVLLFAVDTGLYFSVKTNIRSSTRDWKDHKFKWRKD

PQDK can also be used. Additional CD16A variants and substitutes will be known to, or readily discernible from the scientific literature by, the ordinarily skilled reader.

Competitive assay formats can be used to measure the ability of a CD16A binding protein to inhibit binding of another molecule to the receptor. For example, in one competitive assay format a fixed amount of labeled 3G8 is mixed with varying amounts of either unlabeled 3G8, CD16A binding protein or an irrelevant IgG (control) and added to FcγRIIIA expressing cells. After incubation and separation of the cell-bound material from the material free in solution, the amount of bound labeled 3G8 (and/or optionally also the unbound labeled 3G8) is determined. The concentration of unlabeled mAb which results in a 50% decrease in the binding of labeled 3G8 (IC50) is then determined from this data.

ii. Blocking Immune Complex Binding to FcγRIIIA

Another characteristic of the CD16A binding proteins of the invention is the ability to inhibit binding of immune complexes to CD16A ("IC Blocking Activity"). Usually the binding protein has IC Blocking Activity that is within 4-fold, preferably within 2-fold, of the activity exhibited under similar conditions by 3G8 or the chimeric antibody, Ch3G8, described herein.

Assays for measuring ability of an antibody to block binding of complexed IgG to CD16 are known. See, e.g., Knapp et al., 1989, LEUKOCYTE TYPING IV, Oxford University Press, Oxford, p. 574-97; and Edberg and Kimberly, 1997, *J Immunol* 159:3849-57. One suitable assay is an RIA assay with the format described above for the competitive assay, but substituting $^{125}$I-labeled aggregated irrelevant human $IgG_1$ for the $^{125}$I-labeled 3G8 used in the competitive assay described above.

The invention provides a method of inhibiting the binding of IgG antibodies to CD16 on a cell by contacting the cell with a CD16A binding protein under conditions in which the CD16A binding protein binds the FcγRIII on the cell. The contacting can be in vivo (e.g., by administering the binding protein in a mammal) or in vitro (e.g., by addition of antibodies to cultured cells expressing the FcγRIII). IgG antibodies that are inhibited from binding the FcγRIII can be administered to the animal or added to a culture medium before or after addition or administration of the binding protein, or may be present in an animal normally or in response to a disease state. In one embodiment, the CD16 on the surface of the cell is CD16A.

iii. In Vivo Protection Against Platelet Depletion

The ability of the CD16A binding proteins of the invention to reduce deleterious immune responses can be assessed in a variety of animal models. An exemplary model system is a mouse model for idiopathic thrombocytopenic purpura (ITP) (see, Oyaizu et al., 1988, *J Exp. Med.* 167:2017-22; Mizutani et al., 1993, *Blood* 82:837-44). See Example 9, infra. Other suitable models are known in the art. Other animal models include rodent models of inflammatory diseases described in, for example, *Current Protocols in Immunology* (in some cases modified by using animals transgenic for human CD16A). Transgenic mice can be made using routine methods or can be purchased from commercial sources (e.g., Taconic Inc., German Town, N.Y.).

A example of a procedure suitable for assessing the ability of a CD16A binding protein to provide protection from platelet depletion in a mouse model is described in Example 8, infra. CD16A binding proteins can be administered to muFcγRIII-/-, huFcγRIIIA transgenic mice at a variety of concentrations, and ITP subsequently induced in the mice (e.g., by administering the 6A6 or chimeric 6A6 antibody) to the mice. At timed intervals after the administration of 6A6/ch6A6, the mice are bled and the platelet counts are determined. Optionally, the $IC_{50}$ for each molecule is then determined at the time point where maximal platelet depletion is observed in the negative control group. Based on the results of Example 8 and on prior studies, maximum depletion occurred 2-6 hr after 6A6 administration. $IC_{50}$s are determined graphically, using a curve-fitting program such as the four-parameter fit provided in the SigmaPlot program.

Statistically significant inhibition of depletion of platelets after administration of 6A6 in the treatment group compared to the untreated group and a group administered an identical formulation of an irrelevant, isotype matched mAb is indicative of the desired biological activity.

Experiments in which protection by CD16A binding proteins was assayed are described in the Examples, infra. Preparations of recombinant mouse 3G8 produced in HEK-293 cells, chimeric 3G8 with human IgG1 or IgG2 constant domains (ch3G8-γ1 produced in HEK-293 and CHO-K1 cells, and ch3G8-γ2 produced in HEK-293 cells), and a ch3G8-γ1 variant (ch3G8-γ1 D265A) did not provide significant protection. Murine 3G8, produced from the hybridoma, and a chimeric version of 3G8 containing an aglycosylated human G1 constant region (Ch3G8-G1 N297Q), produced in HEK-293 cells, were able to protect animals from platelet depletion in the mouse model. As shown in Example 10, 11 and 15-17, infra, Ch3G8 N297Q and aglycosylated humanized antibodies protected against platelet depletion in the ITP mouse model. Although not intending to be bound by a particular theory, one possibility is that since ch3G8 N297Q is largely devoid of effector function, it is more efficient than ch3G8 in protecting mice against ITP. Thus, these data suggest that anti-CD16A antibodies without effector function (e.g., aglycosylated antibodies) have advantages compared to some glycosylated (e.g., glycosylated recombinant) antibodies. Further, as described in the examples, administration of aglycosylated anti-CD16A antibody to muFcgRIII-/-, huFcRIIIB transgenic mice did not result in neutrophil depletion in the blood, spleen, and bone marrow. Without intending to be bound by a particular theory, there are several possible explanations for these unexpected results. Protein glycosylation is known to vary in different cell lines, especially those from different species. A difference in the nature of the carbohydrate attached to the antibody constant region as a consequence of expression in different cell types may be responsible for the difference in activity, i.e., if the lack of activity results in part from effector cell activation caused by ch3G8 binding to Fc receptors (or complement) via the antibody Fc region in a glycosylation-dependent manner. Alternatively, recombinant murine and ch3G8 may contain other post-translational modifications that affect activity and which can be eliminated by using different cell lines to express the CD16A binding proteins. It is possible that a combination of isotype and/or isotype containing mutations to eliminate effector function may provide similar protective effects as elimination of the carbohydrate on the Fc.

5. Methods of Treatment

A number of diseases and conditions characterized by a deleterious immune response can be treated using the binding proteins of the invention, i.e., a CD16A binding protein as described herein (e.g., comprising a $V_L$ and/or $V_H$ sequence as disclosed herein and, optionally, a Fc region modified as disclosed herein to have a reduced effector function). In one embodiment, the binding protein is administered to a subject with an autoimmune disease (i.e., a disease characterized by the production of autoantibodies). It is believed that pathogenic IgG antibodies observed in autoimmune diseases are either the pathogenic triggers for these diseases or contribute to disease progression and mediate disease through the inappropriate activation of cellular Fc receptors. Aggregated autoantibodies and/or autoantibodies complexed with self antigens (immune complexes) bind to activating FcRs, thereby triggering the pathogenic sequelae of numerous autoimmune diseases (which occur in part because of immunologically mediated inflammation against self tissues). Without intending to be bound by a particular mechanism of action, the CD16A binding proteins described herein interfere with and reduce the interaction of the autoimmune antibodies and FcγRIII receptors.

Examples of autoimmune diseases that can be treated include, without limitation, idiopathic thrombocytopenic purpura (ITP), rheumatoid arthritis (RA), systemic lupus erythrematosus (SLE), autoimmune hemolytic anemia (AHA), scleroderma, autoantibody triggered urticaria, pemphigus, vasculitic syndromes, systemic vasculitis, Goodpasture's syndrome, multiple sclerosis (MS), psoriatic arthritis, ankylosing spondylitis, Sjögren's syndrome, Reiter's syndrome, Kawasaki's disease, polymyositis and dermatomyositis. Other examples of diseases or conditions that can be treated according to the invention also include any diseases susceptible to treatment with intravenous immunoglobulin (IVIG) therapy (e.g., allergic asthma). Thus, the treatment of autoimmune diseases heretofore treated by IVIG therapy (in one embodiment, a condition other than ITP) is contemplated. While detailed understanding of the mechanism of action of IVIG has not been established, it is proposed that modulating the activity of cellular FcγRs plays a role in its in vivo efficacy. The protective activity of IVIG may rely on the small percentage of dimeric or polymeric IgG present in the preparation. The specificity of the FcγRIII pathway in coupling cytotoxic and immune complex antibodies to effector responses and the ability to directly block this pathway with a mAb strongly suggests that an anti-FcγRIII antibody will have enhanced activity relative to IVIG.

A reduction in a deleterious immune response can be detected as a reduction in inflammation. Alternatively, a reduction in a deleterious immune response can be detected as a reduction in symptoms characteristic of the condition being treated (e.g., a reduction in symptoms exhibited by a subject suffering from an autoimmune condition), or by other criteria that will be easily recognized by physicians and experimentalists in the field of autoimmunity. It will be apparent that, in many cases, specific indicia of reduction will depend on the specific condition being treated. For example, for illustration and not limitation, a reduction in a deleterious immune response in a subject with ITP can be detected as a rise in platelet levels in the subject. Similarly, a reduction in a deleterious immune response in a subject with anemia can be detected as a rise in RBC levels in the subject. A clinician will recognize significant changes in platelet or RBC levels, or other reponses following treatment.

The deleterious immune response is optionally due to idiopathic thrombocytopenic purpura resulting from the administration of an antiplatelet antibody, optionally murine monoclonal antibody 6A6, to a muFcγRIII-/-, huFcγRIIIA transgenic mouse.

In one aspect, the invention provides a method for treating an autoimmune disease, such as ITP, by administering a CD16A binding protein that is largely devoid of effector function. In an embodiment, the CD16A binding protein comprises Fc regions derived from human IgG. In an embodiment, the Fc regions are aglycosyl. In an embodiment, position 297 of each of the $C_H2$ domains is a residue other than asparagine or proline. In one aspect, the binding protein comprises a variable region sequence as described elsewhere herein. However, as discussed herein, the compositions and treatment methods of the invention are not limited to specific CD16A binding proteins derived from murine mAb 3G8, but are applicable to CD16A binding proteins in general. In an embodiment, the CD16A binding protein is a tetrameric antibody protein having two light chains and two heavy chains.

In a related aspect, the invention provides methods of reducing a deleterious immune response in a mammal without significantly reducing neutrophil levels or inducing neutropenia (e.g., severe neutropenia or moderate neutropenia) by administering to the mammal a therapeutically effective amount of a pharmaceutical composition comprising a CD16A binding protein described herein. In an embodiment, the mammal is human. In an embodiment, the mammal is a nonhuman mammal (e.g., mouse) comprising one or more human transgenes.

For therapeutic applications, the binding proteins of the invention are formulated with a pharmaceutically acceptable excipient or carrier, e.g., an aqueous carrier such as water, buffered water, 0.4% saline, 0.3% glycine and the like, optionally including other substances to increase stability, shelf-life or to approximate physiological conditions (sodium acetate, sodium chloride, potassium chloride, calcium chloride, sodium lactate, histidine and arginine). For administration to an individual, the composition is preferably sterile, and free of pyrogens and other contaminants. The concentration of binding protein can vary widely, e.g., from less than about 0.01%, usually at least about 0.1% to as much as 5% by weight. Methods for preparing parentally administerable compositions are known or apparent to those skilled in the art and are described in more detail in, for example, Remington, THE SCIENCE OF PRACTICE AND PHARMACY, 20th Edition Mack Publishing Company, Easton, Pa., 2001). The pharmaceutical compositions of the invention are typically administered by a parenteral route, most typically intravenous, subcutaneous, intramuscular, but other routes of administration can be used (e.g., mucosal, epidermal, intraperitoneal, oral, intranasal, and intrapulmonary). Although not required, pharmaceutical compositions are preferably supplied in unit dosage form suitable for administration of a precise amount. In one embodiment, CD16A binding proteins can be administered in a form, formulation or apparatus for sustained release (e.g., release over a period of several weeks or months).

In one embodiment, polynucleotides encoding CD16A binding proteins (e.g., CD16A binding protein expression vectors) are administered to a patient. Following administration, the CD16A binding protein is expressed in the patient. Vectors useful in administration of CD16A binding proteins can be viral (e.g., derived from adenovirus) or nonviral. Usually the vector will comprise a promoter and, optionally, an enhancer that serve to drive transcription of a protein or proteins. Such therapeutic vectors can be introduced into cells or tissues in vivo, in vitro or ex vivo. For ex vivo therapy, vectors may be introduced into cells, e.g., stem cells, taken from the patient and clonally propagated for autologous transplant back into the same patient (see, e.g., U.S. Pat. Nos. 5,399,493 and 5,437,994).

The compositions can be administered for prophylactic and/or therapeutic treatments. In prophylactic applications, compositions are administered to a patient prior to an expected or potential deleterious immune response. For example, idiopathic thrombocytopenic purpura and systemic lupus erythrematosus are conditions in which a deleterious immune response can be exacerbated by administration of certain medications. The CD16A binding compositions of the invention can be administered in anticipation of such medication-induced responses to reduce the magnitude of the response. In therapeutic applications, compositions are administered to a patient already suffering from a deleterious immune response in an amount sufficient to at least partially ameliorate the condition and its complications. An amount adequate to accomplish this may be a "therapeutically effective amount" or "therapeutically effective dose." Amounts effective for these uses depend upon the severity of the condition and the general state of the patient's own immune system, but generally range from about 0.01 to about 100 mg of antibody per dose, with dosages of from 0.1 to 50 mg and 1 to 10 mg per patient being more commonly used. An "inflammation reducing amount" of the binding protein can also be administered to a mammal to reduce a deleterious immune response.

The administration of the CD16A binding proteins can be administered according to the judgement of the treating physician, e.g., daily, weekly, biweekly or at any other suitable interval, depending upon such factors, for example, as the nature of the ailment, the condition of the patient and half-life of the binding protein.

CD16A binding proteins can be administered in combination with other treatments directed to alleviation of the deleterious immune response or its symptoms or sequelae. Thus, the binding proteins can be administered as part of a therapeutic regimen that includes co-administration of another agent or agents, e.g., a chemotherapeutic agent such as a non-steroidal anti-inflammatory drug (e.g., aspirin, ibuprofen), steroids (e.g., a corticosteroid, prednisone), immunosuppressants (e.g., cyclosporin A, methotrexate, cytoxan), and antibodies (e.g., in conjunction with IVIG).

6. Increasing the Therapeutic Efficacy of a CD16A Binding Protein

In a related aspect, the invention provides a method for increasing the therapeutic efficacy of a CD16A binding protein comprising one or more Fc domains (e.g., anti-CD16A antibodies comprising two Fc domains) by modifying the protein so that it has Fc region(s) with reduced binding to at least one Fc effector ligand compared to the original (i.e., unmodified) Fc region. For example, the Fc region can be modified so that the Fc region is not glycosylated. As described above, modification of the Fc region can be accomplished in several ways (e.g., by genetic mutation, by choice of expression system to change the Fc glycosylation pattern, and the like). In one embodiment, the Fc effector ligand is FcγRIII. In one embodiment, the Fc effector ligand is the C1q component of complement. As used in this context, a subject CD16A binding protein has increased "therapeutic efficacy" compared to a reference binding protein that induces neutropenia when administered if the subject CD16A binding protein does not induce neutropenia (or results in less severe neutropenia). For example, a CD16A binding protein that reduces the severity of a deleterious immune response (e.g., ITP or experimentally induced ITP in a mammal) and reduces neutrophil levels in the animal by x % has greater "therapeutic efficacy" than a CD16A binding protein that reduces the severity of a deleterious immune response and reduces neutrophil levels in the animal by y %, if y is greater than x, e.g. two-fold greater. In one embodiment, the protein is modified by mutation such that the modified protein is aglycosylated.

For example, the invention provides methods for producing a modified CD16 binding protein comprising a modified immunoglobulin heavy chain, the modified CD16 binding protein having greater therapeutic efficacy than a parent CD16 binding protein comprising a parent immunoglobulin heavy chain, by (i) introducing at least one mutation into a parent polynucleotide that encodes the parent immunoglobulin heavy chain to produce a modified polynucleotide that encodes the modified immunoglobulin heavy chain, the mutation introducing into the modified immunoglobulin heavy chain an amino acid substitution that changes, reduces or eliminates glycosylation in the $C_H2$ domain of the parent immunoglobulin heavy chain; and (ii) expressing the modified polynucleotide in a cell as the modified immunoglobulin heavy chain so as to produce the modified CD16 binding protein heavy chain. Optionally, the heavy chain is produced under conditions of co-expression with a light chain to produce a tetrameric antibody.

7. EXAMPLES

Example 1

Mouse 3G8 VH and VL and Chimeric Molecules Generated therefrom

A) Mouse 3G8 VH and VL

The cDNA encoding the mouse 3G8 antibody light chain was cloned. The sequence of the 3G8 antibody heavy chain was provided by Dr. Jeffry Ravetch. The amino acid sequences of the 3G8 $V_H$ and $V_L$ are provided in Tables 1 and 3, infra. Nucleic acid sequences encoding the variable regions are:

```
{3G8VH}
                                                 SEQ ID NO:1
CAGGTTACTCTGAAAGAGTCTGGCCCTGGGATATTGCAGCCCTCCCAGAC

CCTCAGTCTGACTTGTTCTTTCTCTGGGTTTTCACTGAGGACTTCTGGTA

TGGGTGTAGGCTGGATTCGTCAGCCTTCAGGGAAGGGTCTAGAGTGGCTG

GCACACATTTGGTGGGATGATGACAAGCGCTATAATCCAGCCCTGAAGAG
```

-continued

```
CCGACTGACAATCTCCAAGGATACCTCCAGCAACCAGGTATTCCTCAAAA

TCGCCAGTGTGGACACTGCAGATACTGCCACATACTACTGTGCTCAAATA

AACCCCGCCTGGTTTGCTTACTGGGGCCAAGGGACTCTGGTCACTGTCTC

TGCA

{3G8VL}
                                                 SEQ ID NO:3
GACACTGTGCTGACCCAATCTCCAGCTTCTTTGGCTGTGTCTCTAGGGCA

GAGGGCCACCATCTCCTGCAAGGCCAGCCAAAGTGTTGATTTTGATGGTG

ATAGTTTTATGAACTGGTACCAACAGAAACCAGGACAGCCACCCAAACTC

CTCATCTATACTACATCCAATCTAGAATCTGGGATCCCAGCCAGGTTTAG

TGCCAGTGGGTCTGGGACAGACTTCACCCTCAACATCCATCCTGTGGAGG

AGGAGGATACTGCAACCTATTACTGTCAGCAAAGTAATGAGGATCCGTAC

ACGTTCGGAGGGGGGACCAAGCTGGAAATAAAA
```

B) Chimeric Heavy Chain

To create a chimeric gene coding for expression of the mouse 3G8 VH fused to a human constant domain, the nucleic acid encoding the 3G8 $V_H$ was fused to sequences encoding a signal peptide (see Orlandi et al., 1989, *Proc. Natl. Acad. Sci. U.S.A* 86:3833-37; in lower case underline below) and a human Cγ1 constant region (in lower case below) using standard techniques (including overlapping PCR amplification). To facilitate cloning, a SacI site was introduced, resulting in a single residue change in VH FR4 (ala→ser). This change in FR4 does not affect binding to CD16. The resulting nucleic acid had the sequence shown below. The region encoding the $V_H$ domain is in upper case.

```
{ch3G8VH}
gctagcgtttaaacttaagcttgttgactagtgagatcacagttctctctacagtta  SEQ ID NO:5 ctgagcacacaggacctcaccatgggatggagctgtatcatcctcttcttggtagca acagctacaggtaaggggctcacagtagcaggcttgaggtctggacatatatatggg tgacaatgacatccactttgcctttctctccacaggtgtccactccCAGGTTACCCT

GAAAGAGTCTGGCCCTGGGATATTGCAGCCCTCCCAGACCCTCAGTCTGACTTGTTC

TTTCTCTGGGTTTTCACTGAGGACTTCTGGTATGGGTGTAGGCTGGATTCGTCAGCC

TTCAGGGAAGGGTCTAGAGTGGCTGGCACACATTTGGTGGGATGATGACAAGCGCTA

TAATCCAGCCCTGAAGAGCCGACTGACAATCTCCAAGGATACCTCCAGCAACCAGGT

ATTCCTCAAAATCGCCACTGTGGACACTGCAGATACTGCCACATACTACTGTGCTCA

AATAAACCCCGCCTGGTTTGCTTACTGGGGCCAAGGGACTCTGGTCACTGTGAGCTC

Agcctccaccaagggcccatcggtcttccccctggcaccctcctccaagagcacctc tgggggcacagcggccctgggctgcctggtcaaggactacttccccgaaccggtgac ggtgtcgtggaactcaggcgccctgaccagcggcgtgcacaccttcccggctgtcct acagtcctcaggactctactccctcagcagcgtggtgaccgtgccctccagcagctt gggcacccagacctacatctgcaacgtgaatcacaagcccagcaacaccaaggtgga caagagagttgagcccaaatcttgtgacaaaactcacacatgcccaccgtgcccagc acctgaactcctggggggaccgtcagtcttcctcttccccccaaaacccaaggacac
```

```
cctcatgatctcccggacccctgaggtcacatgcgtggtggtggacgtgagccacga agaccctgaggtcaagttcaactggtacgtggacggcgtggaggtgcataatgccaa gacaaagccgcggggaggagcagtacaacagcacgtaccgtgtggtcagcgtcctcac cgtcctgcaccaggactggctgaatggcaaggagtacaagtgcaaggtctccaacaa agccctcccagcccccatcgagaaaaccatctccaaagccaagggcagccccgaga accacaggtgtacaccctgcccccatcccgggatgagctgaccaagaaccaggtcag cctgacctgcctggtcaaaggcttctatcccagcgacatcgccgtggagtgggagag caatgggcagccggagaacaactacaagaccacgcctcccgtgctggactccgacgg ctccttcttcctctacagcaagctcaccgtggacaagagcaggtggcagcaggggaa cgtcttctcatgctccgtgatgcatgaggctctgcacaaccactacacgcagaagag cctctccctgtctccgggtaaatgagtgcggccgcgaattc
```

This construct was inserted into the pCI-Neo (Promega Biotech) at the NheI-EcoRI sites of the polylinker for use for expression of the chimeric heavy chain in cells.

C) Chimeric Light Chain

To create a chimeric gene coding for the mouse 3G8 $V_L$ fused to a human constant domain, this 3G8 $V_L$ segment was fused to a signal sequence (as for the $V_H$ above; (lower case underlined) and a human Cκ constant region (lower case) cDNA using standard techniques, resulting in a nucleic acid with the sequence shown below:

ch3G8VL

SEQ ID NO:6

```
gctagctgagatcacagttctctctacagttactgagcacacaggacctc accatgggatggagctgtatcatcctcttcttggtagcaacagctacagg taaggggctcacagtagcaggcttgaggtctggacatatatatgggtgac aatgacatccactttgcctttctctccacaggtgtccactccGACACTGT

GCTGACCCAATCTCCAGCTTCTTTGGCTGTGTCTCTAGGGCAGAGGGCCA

CCATCTCCTGCAAGGCCAGCCAAAGTGTTGATTTTGATGGTGATAGTTTT

ATGAACTGGTACCAACAGAAACCAGGACAGCCACCCAAACTCCTCATCTA

TACTACATCCAATCTAGAATCTGGGATCCCAGCCAGGTTTAGTGCCAGTG

GGTCTGGGACAGACTTCACCCTCAACATCCATCCTGTGGAGGAGGAGGAT

ACTGCAACCTATTACTGTCAGCAAAGTAATGAGGATCCGTACACGTTCGG

AGGGGGGACCAAGCTTGAGATCAAAcgaactgtggctgcaccatcggtct tcatcttcccgccatctgatgagcagttgaaatctggaactgcctctgtt gtgtgcctgctgaataacttctatcccagagaggccaaagtacagtggaa ggtggataacgccctccaatcgggtaactcccaggagagtgtcacagagc aggacagcaaggacagcacctacagcctcagcagcaccctgacgctgagc aaagcagactacgagaaacacaaagtctacgcctgcgaagtcacccatca gggcctgagctcgcccgtcacaaagagcttcaacaggggagagtgttagt tctagagtcgactctagaggatccccgggtaccgagctcgaattc
```

This construct was inserted into pCI-Neo (Promega Biotech) at the NheI-EcoRI sites of the polylinker for use for expression of the chimeric light chain in cells.

D) Expression

The ch3G8VH and ch3G8VL chimeric proteins described above can be co-expressed to form a chimeric antibody, referred to as ch3G8. The chimeric antibody ch3G8 can be expressed either in a myeloma or in other mammalian cells (e.g., CHO, HEK-293). An example of a procedure for expression of CD16A binding proteins such as ch3G8 and variants is provided in Example 4, infra.

Example 2

Humanized Anti-CD16A Binding Proteins

A) Humanized Heavy Chain

CDR encoding sequences from the mouse 3G8 $V_H$ clone were fused to framework sequences derived from the human germline VH sequence VH2-70 to create a polynucleotide encoding a $V_H$ designated Hu3G8VH. The polynucleotide was generated by an overlapping PCR procedure. In a first step, using the primers and strategy shown below and the mouse 3G8 $V_H$ polynucleotide (SEQ ID NO: 1) as template.

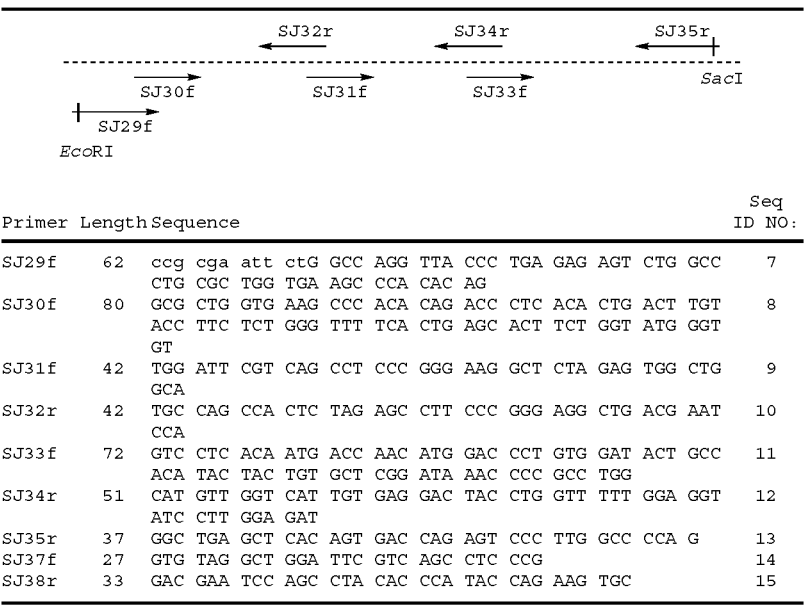

| Primer | Length | Sequence | Seq ID NO: |
|---|---|---|---|
| SJ29f | 62 | ccg cga att ctG GCC AGG TTA CCC TGA GAG AGT CTG GCC CTG CGC TGG TGA AGC CCA CAC AG | 7 |
| SJ30f | 80 | GCG CTG GTG AAG CCC ACA CAG ACC CTC ACA CTG ACT TGT ACC TTC TCT GGG TTT TCA CTG AGC ACT TCT GGT ATG GGT GT | 8 |
| SJ31f | 42 | TGG ATT CGT CAG CCT CCC GGG AAG GCT CTA GAG TGG CTG GCA | 9 |
| SJ32r | 42 | TGC CAG CCA CTC TAG AGC CTT CCC GGG AGG CTG ACG AAT CCA | 10 |
| SJ33f | 72 | GTC CTC ACA ATG ACC AAC ATG GAC CCT GTG GAT ACT GCC ACA TAC TAC TGT GCT CGG ATA AAC CCC GCC TGG | 11 |
| SJ34r | 51 | CAT GTT GGT CAT TGT GAG GAC TAC CTG GTT TTT GGA GGT ATC CTT GGA GAT | 12 |
| SJ35r | 37 | GGC TGA GCT CAC AGT GAC CAG AGT CCC TTG GCC CCA G | 13 |
| SJ37f | 27 | GTG TAG CTG GA TTC GTC AGC CTC CCG | 14 |
| SJ38r | 33 | GAC GAA TCC AGC CTA CAC CCA TAC CAG AAG TGC | 15 |

The resulting fragment was digested with EcoRI and SacI and cloned into pUC18. After sequencing, one plasmid was selected for a final round of overlapping PCR to correct a deletion which occurred during the second PCR step. The resulting polynucleotide had the sequence:

{hu3G8VH}
SEQ ID NO:16
CAGGTTACCCTGAGAGAGTCTGGCCCTGCGCTGGTGAAGCCCACACAGAC

CCTCACACTGACTTGTACCTTCTCTGGGTTTTCACTGAGCACTTCTGGTA

TGGGTGTAGGCTGGATTCGTCAGCCTCCCGGGAAGGCTCTAGAGTGGCTG

GCACACATTTGGTGGGATGATGACAAGCGCTATAATCCAGCCCTGAAGAG

CCGACTGACAATCTCCAAGGATACCTCCAAAAACCAGGTAGTCCTCACAA

TGACCAACATGGACCCTGTGGATACTGCCACATACTACTGTGCTCGGATA

AACCCCGCCTGGTTTGCTTACTGGGGCCAAGGGACTCTGGTCACTGTGAG

CTCA

The Hu3G8VH sequence was then combined with segments coding for a secretion signal sequence (as described above; lower case underline) and cDNA for the human Cγ1 constant region (lower case). The resulting polynucleotide had the sequence:

{hu3G8VH-1}
SEQ ID NO:17
<u>gctagcgtttaaacttaagcttgttgactagtgagatcacagttctctct</u>

<u>acagttactgagcacacaggacctcaccatgggatgagctgtatcatcc</u>

<u>tcttcttggtagcaacagctacaggtaaggggctcacagtagcaggcttg</u>

<u>aggtctggacatatatatgggtgacaatgacatccactttgcctttctct</u>

<u>ccacaggtgtccactcc</u>CAGGTTACCCTGAGAGAGTCTGGCCCTGCGCTG

GTGAAGCCCACACAGACCCTCACACTGACTTGTACCTTCTCTGCGTTTTC

ACTGAGCACTTCTGGTATGGGTGTAGGCTGGATTCGTCAGCCTCCCGGGA

-continued

AGGCTCTAGAGTGGCTGGCACACATTTCGTGGGATGATGACAAGCGCTAT

AATCCAGCCCTGAAGAGCCGACTGACAATCTCCAAGGATACCTCCAAAAA

CCAGGTAGTCCTCACAATGACCAACATGGACCCTGTGGATACTGCCACAT

ACTACTGTGCTCGGATAAACCCCGCCTGGTTTGCTTACTGGGGCCAAGGG

ACTCTGGTCACTGTGAGCTCAgcctccaccaagggcccatcggtcttccc cctggcaccctcctccaagagcacctctgggggcacagcggccctgggct gcctggtcaaggactacttccccgaaccggtgacggtgtcgtggaactca ggcgccctgaccagcggcgtgcacaccttcccggctgtcctacagtcctc aggactctactccctcagcagcgtggtgaccgtgccctccagcagcttgg gcacccagacctacatctgcaacgtgaatcacaagcccagcaacaccaag gtggacaagagagttgagcccaaatcttgtgacaaaactcacacatgccc accgtgcccagcacctgaactcctggggggaccgtcagtcttcctcttcc ccccaaaacccaaggacaccctcatgatctcccggacccctgaggtcaca tgcgtggtggtggacgtgagccacgaagaccctgaggtcaagttcaactg gtacgtggacggcgtggaggtgcataatgccaagacaaagccgcgggagg agcagtacaacagcacgtaccgtgtggtcagcgtcctcaccgtcctgcac caggactggctgaatggcaaggagtacaagtgcaaggtctccaacaaagc cctcccagcccccatcgagaaaaccatctccaaagccaaagggcagcccc gagaaccacaggtgtacaccctgcccccatcccgggatgagctgaccaag aaccaggtcagcctgacctgcctggtcaaaggcttctatcccagcgacat cgccgtggagtgggagagcaatgggcagccggagaacaactacaagacca cgcctcccgtgctggactccgacggctccttcttcctctacagcaagctc accgtggacaagagcaggtggcagcaggggaacgtcctctcatgctccgt -continued
```
gatgcatgaggctctgcacaaccactacacgcagaagagcctctccctgt
ctccgggtaaatgagtgcggccgcgaattc
```

For expression in mammalian cells (HEK-293), the Hu3G8VH-1 sequence was cloned into the pCI-Neo polylinker at the NheI-EcoRI sites, following intervening cloning into pUC and pCDNA3.1.

B) Humanized Light Chain

CDR encoding sequences from the mouse 3G8 $V_L$ clone were fused to framework sequences derived from the human B3 germline V-κ gene. The polynucleotide was generated by an overlapping PCR procedure using the primers and strategy shown below and the mouse 3G8 $V_L$ polynucleotide (SEQ ID NO: 2) as template.

-continued
```
taaggggctcacagtagcaggcttgaggtctggacatatatatgggtgac
aatgacatccactttgcctttctctccacaggtgtccactccGACACTGT
GCTGACCCAATCTCCAGCTTCTTTGGCTGTGTCTCTAGGCCAGAGGGCCA
CCATCTCCTGCAAGGCCAGCCAAAGTGTTGATTTTGATGCTGATAGTTTT
ATGAACTGGTACCAACAGAAACCAGGACAGCCACCCAAACTCCTCATCTA
TACTACATCCAATCTAGAATCTGGGATCCCAGCCAGGTTTAGTGCCAGTG
GGTCTGGGACAGACTTCACCCTCAACATCCATCCTGTGGAGCAGGAGGAT
ACTGCAACCTATTACTGTCAGCAAAGTAATGAGGATCCGTACACGTTCGG
```

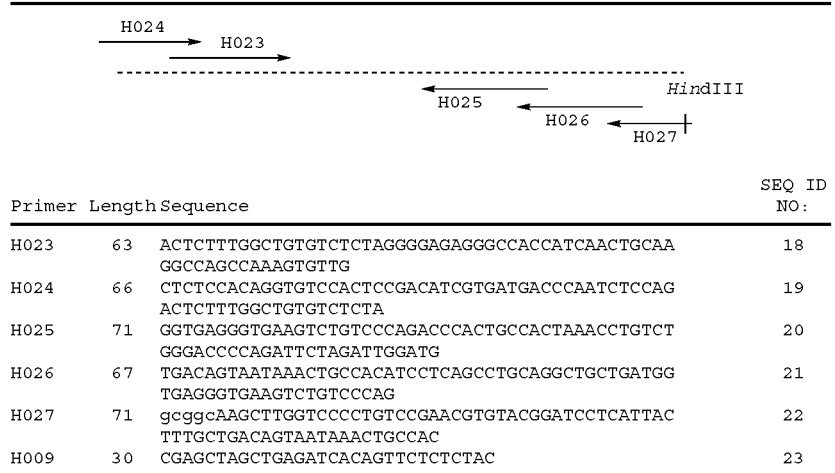

| Primer | Length | Sequence | SEQ ID NO: |
|---|---|---|---|
| H023 | 63 | ACTCTTTGGCTGTGTCTCTAGGGGAGAGGGCCACCATCAACTGCAA GGCCAGCCAAAGTGTTG | 18 |
| H024 | 66 | CTCTCCACAGGTGTCCACTCCGACATCGTGATGACCCAATCTCCAG ACTCTTTGGCTGTGTCTCTA | 19 |
| H025 | 71 | GGTGAGGGTGAAGTCTGTCCCAGACCCACTGCCACTAAACCTGTCT GGGACCCCAGATTCTAGATTGGATG | 20 |
| H026 | 67 | TGACAGTAATAAACTGCCACATCCTCAGCCTGCAGGCTGCTGATGG TGAGGGTGAAGTCTGTCCCAG | 21 |
| H027 | 71 | gcggcAAGCTTGGTCCCCTGTCCGAACGTGTACGGATCCTCATTAC TTTGCTGACAGTAATAAACTGCCAC | 22 |
| H009 | 30 | CGAGCTAGCTGAGATCACAGTTCTCTCTAC | 23 |

The resulting polynucleotide had the sequence

{hu3G8VL}
SEQ ID NO:25
```
GACACTGTGCTGACCCAATCTCCAGCTTCTTTGGCTGTGTCTCTAGGGCA
GAGGGCCACCATCTCCTGCAAGGCCAGCCAAAGTGTTGATTTTGATGGTC
ATAGTTTTATGAACTGGTACCAACAGAAACCAGGACAGCCACCCAAACTC
CTCATCTATACTACATCCAATCTAGAATCTGGGATCCCAGCCAGCTTTAG
TGCCAGTGGGTCTGGGACAGACTTCACCCTCAACATCCATCCTGTGGAGG
AGGAGGATACTGCAACCTATTACTGTCAGCAAAGTAATGAGGATCCGTAC
ACGTTCGGAGGGGGGACCAAGCTTGAGATCAAA
```

The Hu3G8 VL gene segment was combined with a signal sequence (as described above, lower case, underline) and a human C-κ constant region (lower case) cDNA using standard techniques resulting in a product with the sequence below:

{hu3G8VL-1}
SEQ ID NO:26
```
gctagctgagatcacagttctctctacagttactgagcacacaggacctc
accatgggatggagctgtatcatcctcttcttggtagcaacagctacagg
```
-continued
```
AGGGGGGACCAAGCTTGAGATCAAAcgaactgtggctgcaccatcggtct
tcatcttcccgccatctgatgagcagttgaaatctggaactgcctctgtt
gtgtgcctgctgaataacttctatcccagagaggccaaagtacagtggaa
ggtggataacgccctccaatcgggtaactcccaggagagtgtcacagagc
aggacagcaaggacagcacctacagcctcagcagcaccctgacgctgagc
aaagcagactacgagaaacacaaagtctacgcctgcgaagtcacccatca
gggcctgagctcgcccgtcacaaagagcttcaacaggggagagtgttagt
tctagagtcgactctagaggatccccgggtaccgagctcgaattc
```

This construct was inserted into pCI-Neo for expression in mammalian cells.

Example 3

Variant CD16A Binding Proteins

Additional expression constructs were made in which sequence changes were introduced in the $V_L$ or $V_H$ domains by site directed mutagenesis. A typical mutagenesis reaction contained 10 ng plasmid DNA (isolated from a methylation competent strain of E. coli), 125 ng each of a forward and reverse primer, each containing the mutation of interest, reaction buffer, and dNTPs in 0.05 ml volume. 2.5 units of PFUTURBO® DNA polymerase (Stratagene) was added and the reaction was subjected to 15 cycles of 95°, 30 sec; 55°, 1 min; 68°, 12 min. The product of the PCR was then digested with DpnI endonuclease and the restricted DNA was used to transform *E. coli* strain XL-10 GOLD® ultra-competent cells. Because DpnI only digests methylated DNA it will digest the parental, non-mutated, plasmid leaving the newly synthesized non-methylated product, containing the mutation of interest, as the predominant species.

The sequences of the variant $V_H$ domains are shown in Table 3. The sequences of the variant $V_L$ domains are shown in Table 4.

Example 4

Expression in Mammalian Cells

Various combinations of heavy and light chain expression plasmids (e.g., comprising the chimeric, humanized and variant $V_L$ and $V_H$ domains fused to human Cγ1 and Cκ constant domains as described above) were co-transfected into HEK-293 cells for transient expression of recombinant tetrameric antibodies (i.e., comprising 2 heavy chains and 2 light chains), sometimes referred to herein as "recombinant antibodies." Transfection was carried out using LIPO-FECTAMINE® 2000 (Invitrogen) in 6 well plates according to the manufacturer's instructions.

Recombinant antibodies were prepared by cotransfection of a heavy chain expression plasmid (i.e., encoding a heavy chain comprising a $V_H$ and constant domains) and light chain expression plasmids (i.e., encoding a light chain comprising a $V_L$ and constant domains) together into HEK-293 cells for transient expression of recombinant antibodies.

Hu3G8VH variants listed in Table 3 were coexpressed with the hu3G8VL-1 light chain. For reference, most assays included (i) recombinant antibodies produced by coexpression of ch3G8VH and ch3G8VL ("ch3G8VH/ch3G8VL") and (ii) recombinant antibodies produced by coexpression of hu3G8VH-1 and hu3G8VL-1 ("hu3G8VH-1/hu3G8VL-1").

Hu3G8VL variants listed in Table 4 were coexpressed with the ch3G8VH heavy chain. For reference, most assays included (i) recombinant antibodies produced by coexpression of ch3G8VH and ch3G8VL ("ch3G8VH/ch3G8VL") and (ii) recombinant antibodies produced by coexpression of ch3G8VH and hu3G8VL-1 ("ch3G8VH/hu3G8VL-1").

After three days, the levels of recombinant antibodies in the conditioned media were determined by ELISA, and the recombinant antibodies were analyzed by ELISA for binding to captured sCD16A as described in Examples 5. Selected antibodies were assayed for cell binding to cells expressing the extracellular domain of CD16A, as shown in Example 6.

Example 5

ELISA Determination of Binding to CD16A

Sandwich ELISA was performed to detect binding of antibodies to a soluble form of CD16A.

Soluble Human CD16A

A soluble form of human CD16A was expressed from HEK-293 cells using a pcDNA3.1-derived expression vector containing the CD16A gene truncated just prior to the transmembrane region. To create the vector, cDNA encoding CD16A was amplified using the primers 3A$_{left}$ [gttggatcctc-caactgctctgctacttctagttt] (SEQ ID NO:27) and 3A$_{right}$ [gaaaagcttaaagaatgatgagatggttgacact] (SEQ ID NO:28) digested with BamHI and HindIII, and cloned into the vector pcDNA3.1 (Novagen) at the Bam/HindIII site of the polylinker. The construct was used to transiently transfect HEK-293 cells. For some assays, the secreted product was purified from conditioned medium using affinity chromatography on a human IgG Sepharose column. In some assays, the amount of sCD16A in conditioned medium was quantitated and unpurified sCD16A was used. Purification was not required since the ELISA capture antibody (LNK16 mAb) specifically bound the antigen, allowing removal of contaminants in washing steps.

The amino acid sequence of the sCD16 construct is shown below. (The signal sequence, underlined, is cleaved off during expression. Note the last seven residues are derived from the vector pCDNA3.1 rather than from the CD16A gene):

```
                                          (SEQ ID NO:29)
MWQLLLPTALLLLVSAGMRTEDLPKAVVFLEPQWYRVLEKDSVTLKCQGA

YSPEDNSTQWFHNESLISSQASSYFIDAATVDDSGEYRCQTNLSTLSDPV

QLEVHIGWLLLQAPRWVFKEEDPIHLRCHSWKNTALHKVTYLQNGKGRKY

FHHNSDFYIPKATLKDSGSYFCRGLFGSKNVSSETVNITITQGLAVSTIS

SFFKLAAARV
```

ELISA Format

Plates were first coated with 100 ng/well of the anti-CD16 mAb LNK-16 (Advanced ImmunoChemical, Long Beach Calif.; see 5th Human Lymphocyte Differentiation Antigens Workshop) in carbonate buffer at room temperature for 2 hrs. Any anti-sCD16A antibody that does not block binding by 3G8 can be used. After blocking for 30 minutes with PBS-T-BSA, sCD16A conditioned medium was added at a dilution of 1/10 and incubated at room temperature for 16 hrs. Alternatively, when purified sCD16 was used, it was diluted to a concentration of 50 ng/ml in PBS-T-BSA. 0.05 ml was added to each well and incubated for at least 2 hrs at room temperature.

The plate was washed and dilutions of recombinant antibodies starting at 0.5 µg/ml in PBS-T-BSA were then added and incubated for 1 hr at room temp. Binding of recombinant antibodies to the captured sCD16A was then measured using an anti-human IgG-HRP conjugate and TMB substrate. After stopping color development using dilute sulfuric acid, the plate was read at 450 nM.

Results of Binding Assays

This example shows that the binding properties of humanized anti-CD16A antibodies for binding to CD16A are the same or similar to the properties of the chimeric 3G8 antibody.

Based on the comparative binding studies, the recombinant antibodies were classified as binding with high, intermediate, or low affinity. Antibodies with high and intermediate binding affinity are discussed above in section 4. The recombinant antibodies with a $V_H$ domain of hu3G8VH-9, 10, 11, 13, 15, 21, 38, 39, or 41 showed little or no binding to sCD16A. From these data it appears certain substitutions (or combinations of substitutions) are generally detrimental to binding. For example, substitution of tyrosine or aspartic acid at $V_H$ position 52 (i.e., 52Y and 52D) or threonine at position 94 (94T) are detrimental to binding. Similarly, the combination of leucine at position 50 with aspartic acid at position 54 (50L+54N) is detrimental to binding, as is the combination of arginine at 94 and aspartic acid at 101 (94R+101D). However, aspartic acid at 101 is tolerated when position 94 is glutamine, lysine, histidine or alanine (but not arginine). Further 34V+94R+101D has intermediate activity. This indicates a relationship between positions 34, 94 and 101 in maintaining high affinity binding, and suggests that 34V may be an especially important residue. Likewise, recombinant antibodies with a $V_L$ domain of hu3G8VL-6, 7, 8, 9, 11, 12, 13, and 14 showed little or no binding to sCD16A. From these data it appears certain substitutions (or combinations of substitutions) are generally detrimental to binding. For example, substitution of alanine at position 34 (34A) or tyrosine at position 92 (92Y) is generally detrimental to binding.

Results of an exemplary binding assay are shown in FIG. 1.

Example 6

Antibody Binding to Cells Expressing CD16A

The ability of selected humanized antibodies to bind to CD16A expressed by CHO-K1 cells as assayed by direct binding competition assays.

CHO-K1 cells expressing extracellular domain of FcRIIIa fused to the transmembrane and intracellular domain of FcRIIb were used for cell binding assays. Cells were plated at 40,000 cells per well in 96 well flat bottom tissue culture plates (FALCON® MICROTEST™ Tissue Culture plate, 96 well) and incubated at 37° C. $CO_2$ incubator for approximately 24 hr. The plate was then gently washed three times with 25 mM Hepes, 75 uM EDTA, 11.5 mM KCl, 115 mM NaCl, 6 mM MgSO4, 1.8 mM CaCl2, 0.25% BSA (binding buffer).

Figure 2:
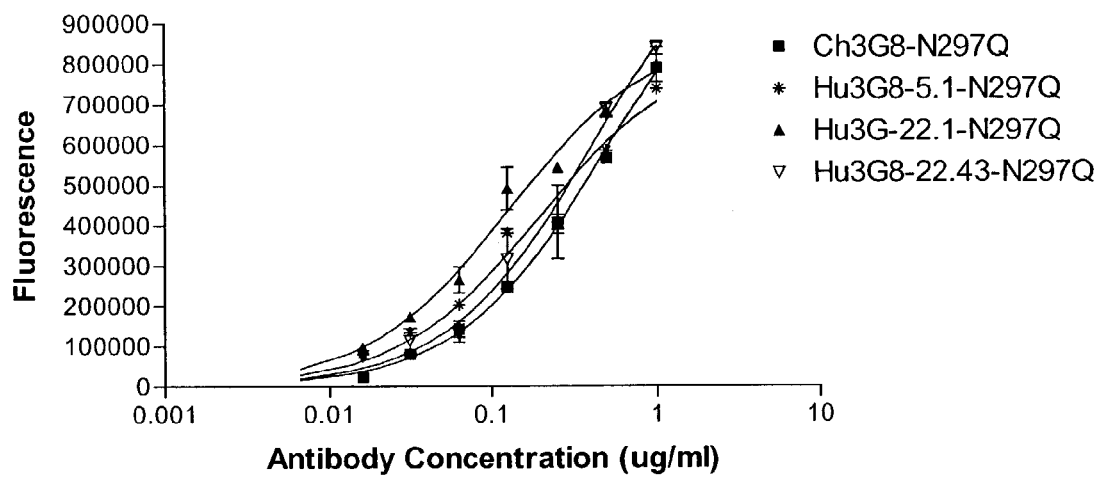
FIG. 2 shows results of an assay for binding of humanized and chimeric antibodies to CHO-K1 cells expressing the extracellular domain of CD16A. Hu3G8-22.1 is an antibody with the heavy chain Hu3G8VH-22, and the light chain Hu3G8VL-1. Hu3G8-5.1 is an antibody with the heavy chain Hu3G8VH-5, and the light chain Hu3G8VL-1. Hu3G8-22.43 is an antibody with the heavy chain Hu3G8VH-22, and the light chain Hu3G8VL-43. N297Q indicates the antibody is aglycosylated.

For indirect binding assays, 100 µl of a serial dilution of anti-CD16 Mab (final concentration: 1 ug/ml, 0.5, 0.25, 0.125, 0.0625, 0.03, 0.015, 0 ug/ml) was then added to wells in binding buffer. The plate was then incubated at 23° C. for 1 hr and washed three times with binding buffer. 50 µl/well of Europium (EU)-labeled-antihuman-IgG (100 ng/ml) was then added to each well and the plate was incubated at 23° C. for 30 minutes then washed three times with binding buffer. Finally, 100 µl DELFIA® enhancement solution, an acidic chelating detergent solution intended for use in the quantative determination of $Eu^{3+}/Sm^{3+}$ (PerkinElmer/Wallac) was added. After incubating with shaking for 15 minutes, the plate was read for time resolved fluorescence (excitation 340 nm; emission 615 nm) in a VICTOR² instrument (PerkinElmer/Wallac). The results of the assay are shown in FIG. 2.

Figure 3:
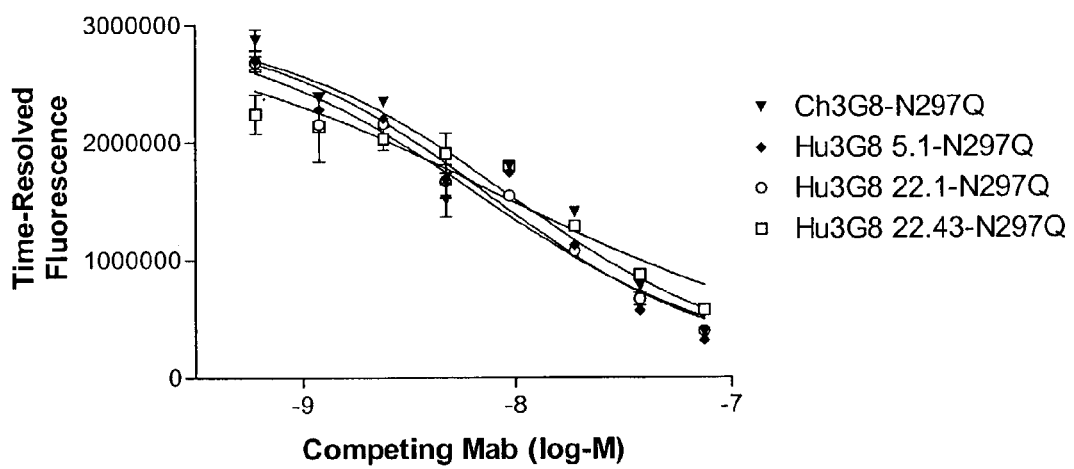
FIG. 3 shows results of a cell based competition assay. The aglycosylated humanized antibodies shown compete with aglycosylated chimeric antibody for binding to CHO-K1 cells expressing the extracellular domain of CD16A.

The CHO-K1 cells described above were also used in competition assays. After washing with binding buffer as described above, varying amounts of purified unlabeled Mab (1.2-75 nM final concentration) were mixed with a fixed concentration of Eu-Ch3G8-N297Q (final concentration 2.5 nM). The plate was then incubated at 23° C. for 1 hr and washed three times with binding buffer. 100 µl DELFIA® enhancement solution (PerkinElmer/Wallac) was the added and after incubating with shaking for 15 minutes, the plate was read for time resolved fluorescence (excitation 340 nm; emission 615 nm) in a VICTOR² instrument (PerkinElmer/Wallac). The results of the assay are shown in FIG. 3.

These assays demonstrate that the humanized anti CD16A monoclonal antibodies bind with high affinity to CD16A on the surface of transfected cells. Hu3G8-22.1-N297Q binds to CD16A bearing cells with higher affinity than Ch3G8-N297Q.

Example 7

Inhibition of Binding of sCD16A to Immune Complexes

Assay of 4-4-20 Binding to FITC-BSA

The binding of ch4-4-20 or ch4-4-20 (D265A) to FITC-BSA was assessed by ELISA. (Ch4-4-20 is identical to Ch3G8 except that it contains the respective VH and VL regions of 4-4-20 instead of those of 3G8. Thus it retains high affinity and specificity for the hapten fluorescein. 4-4-20 is described in Bedzyk et al., 1989, *J Biol Chem* 264:1565-9.) FITC-BSA (1 ug/ml-50 ng/well) was coated onto Nunc maxisorb immunoplates in carbonate buffer and allowed to bind for approximately 16 hr. Following blocking with BSA, dilutions of ch4-4-20 were added to the wells and allowed to bind for 1 hr at RT. After washing out unbound Mab, HRP-conjugated goat anti-human Ig secondary was added. One hour later the secondary antibody was removed, washed and developed with TMB substrate. Following addition of an acidic stop solution the plate was read at 450 nm. Both ch4-4-20 and ch4-4-20(D265A) bound to the FITC-BSA with high affinity (data not shown).

Assay of sFcR Binding to ch4-4-20/FITC-BSA Immune Complexes

The same format was used to assay binding of sFcRs to immune complexes (IC) formed on the ELISA plate between ch4-4-20 and FITC-BSA. In this case we have used either biotinylated sFcR or biotinylated anti-human G2 Mab as a secondary reagent, followed by streptavidin-HRP detection.

Inhibition of sFcR Binding to IC by Murine, Chimeric and Humanized 3G8

Figure 4:
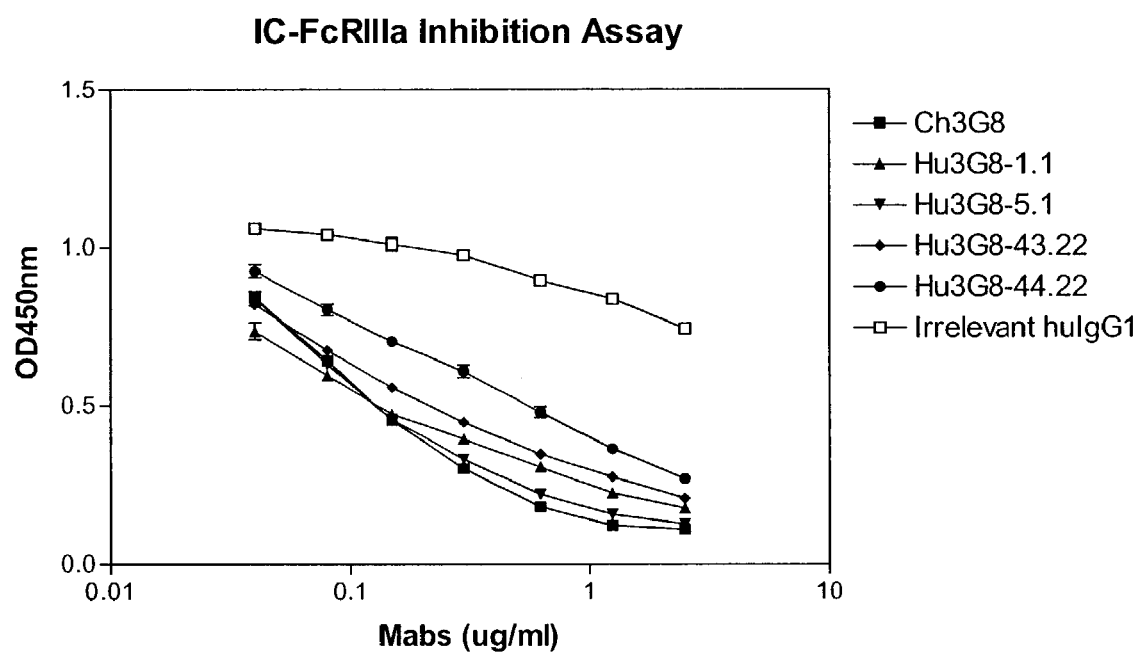
FIG. 4 shows inhibition of binding of sCD16A to immune complexes. Hu3G8-1.1 is an antibody with the heavy chain Hu3G8VH-1, and the light chain Hu3G8VL-1.

The concentrations of ch4-4-20 and sFcR were fixed to give approximately 90 percent maximal signal in the assay. sCD16A was premixed with serial dilutions of murine, chimeric or humanized 3G8 and incubated for one hour prior to adding to the plate containing the immune complex. Serial dilutions of humanized or chimeric 3G8 were incubated with sCD16A-G2-biotin for one hour. The mixtures were then added to ELISA wells containing an immune complex between a human IgG1 chimeric form of the anti-fluorescein Mab 4-4-20 and FITC-BSA. After one hour, binding of the soluble receptor to the IC was detected using streptavidin-HRP conjugate and TMB development. The results are shown in FIG. 4. This assay indicates that humanized anti-CD16A antibodies are potent inhibitors of CD16A binding to IgG in immune complexes.

Example 8

Analysis of Anti-CD16A Monoclonal Antibody Panel

A panel of hybridomas was generated following immunizing and boosting mice with sCD16A using standard methods. Eight 96-well plates were screened by ELISA for binding activity on plates coated directly with sCD16A. Ninety-three of these gave a positive signal and were expanded further. Of these, 37 were positive for binding to human blood cells by FACS. These supernatants were then analyzed for their ability to block the interaction of CD16A with immune complexes and for the similarity of the binding site (epitope) to that of 3G8. Assays included capture ELISA using chimeric 3G8 down and inhibition of immune complex binding to sRIIIa-Ig. Based on these assays antibodies with binding and inhibitory properties similar to 3G8 were isolated, as well as Mabs with binding and/or inhibitory properties distinct from 3G8.

DJ130c (DAKO) and 3G8 were used as controls in the assays. Mab DJ130c is a commercially available Mab which binds CD16 at an epitope distinct from 3G8 (Tamm and Schmidt). This Mab does not block FcRIIIa-immune complex binding (Tamm and Schmidt). In an ELISA-based inhibition assay, DJ130c enhances rather than inhibits binding.

The data indicate that the panel contains antibodies which bind to the same epitope as Ch3G8 and block sCD16A binding to immune complexes. The panel of Mabs also contains antibodies which do not bind to the same epitope as Ch3G8. Most of these latter antibodies do not block the interaction of sCD16a with IgG in immune complexes.

TABLE

| | | Effect on sCD16a Binding to Immune Complexes | | |
|---|---|---|---|---|
| Assay | Result | Inhibition | Enhancement | No Effect |
| Binding to sCD16 | Positive | 2 | 5 (+DJ-130c) | 17 |
| Captured by Ch3G8 | Negative | 11 (+3G8) | 0 | 2 |

Example 9

Induction of Platelet Depletion In Vivo

The in vivo activity of a CD16A binding protein for blocking human Fc-FcγRIII interactions induced by autoantibodies can be evaluated using animal models of autoimmune diseases. One suitable model is the "passive mouse model" of ITP and the anti-platelet mAb 6A6 (see, Oyaizu et al., 1988, *J Exp. Med.* 167:2017-22; Mizutani et al., 1993, *Blood* 82:837-44). 6A6 is an IgG2a isotype mAb derived from a NZW×BSXB F1 individual. Administration of 6A6 depletes platelets in muFcγRIII −/−, huFcγRIIIA transgenic mice but not in muFcγRIII−/− mice without the human transgene. See Samuelsson et al., 2001, *Science* 291:484-86. Other anti-platelet monoclonal antibodies can be used in place of 6A6 in the model. Alternatively, a polyclonal anti-platelet antibody can be used.

CD16A binding proteins that confer the greatest degree of protection from platelet depletion can be identified by administrating CD16A binding proteins to a muFcγRIII −/−, huFcγRIIIA transgenic mouse and measuring any reduction in mAb 6A6 induced platelet depletion.

A related assay can be carried out using a chimeric human IgG$_1$κ chimeric derivative of 6A6 in place of the mouse mAb in the protocol provided above, so that the depleting mAb had a human isotype. To conduct this assay, a chimeric 6A6 monoclonal antibody (ch6A6) was prepared by fusing the cDNA segments encoding the murine anti-platelet monoclonal antibody 6A6 V$_H$ and V$_L$ regions to the human Cγ1 and Cκ cDNA segments, respectively. The resulting genes were co-expressed in 293 cells and chimeric 6A6 was purified by protein A affinity chromatography followed by size exclusion chromatography.

To demonstrate that the chimeric 6A6 antibody induces platelet depletion, ch6A6 was administered to muFcγRIII−/−, huFcγRIIIA transgenic mice. The ch6A6 was administered to each animal either i.v. or intraperitoneally (i.p.) (0.1 µg/g).

Animals were bled 2 hrs, 5 hrs, 24 hrs and 48 hrs after administration of ch6A6, and plasma platelet counts were determined using a Z2™ COULTER COUNTER® particle counter and size analyzer equipped with a 70 µm aperture. Particles between 1.5 and 4 µm in size (corresponding to platelets) were counted and the data were analyzed by plotting the platelet count versus time for each concentration.

Two hours after injection of 0.1 µg/g ch6A6 i.p., approximately 75% of the platelets were depleted. The number of platelets remained low for 5 hours after ch6A6 injection then progressively increased to return to normal 72 hours after ch6A6 injection.

Two hours after injection of 0.1 µg/g ch6A6 i.v., approximately 60% of the platelets were depleted. The number of platelets remained low for 6 hours after ch6A6 injection then progressively increased to return to normal 48 hours after ch6A6 injection.

Example 10

Analysis of the Ability of CD16 Binding Antibodies to Protect Mice from Platelet Depletion The ability of CD16A binding proteins to reduce platelet depletion in experimental ITP can be assayed as described below. CD16A binding proteins were administered intravenously (i.v.) to groups of muFcγRIII$^{-/-}$, huFcγRIIIA transgenic mice at concentrations of 0.5, 1, 2 or 5 µg/g in phosphate buffered saline (PBS). Controls were PBS alone or an irrelevant human IgGI (negative control) or human intravenous immunoglobulin (IVIG; positive control). One hour after administration of the CD16A binding protein or control, ITP was induced by administering 0.1 µg/g ch6A6 to each animal either intravenously or intraperitoneally. Animals were bled 2 hrs, 5 hrs, 24 hrs and 48 hrs after administration of ch6A6. Plasma platelet counts were determined using the Z2™ COULTER COUNTER® particle counter and size analyzer as described above and the data were analyzed by plotting the platelet count versus time for each concentration of administered binding protein.

Figure 5:
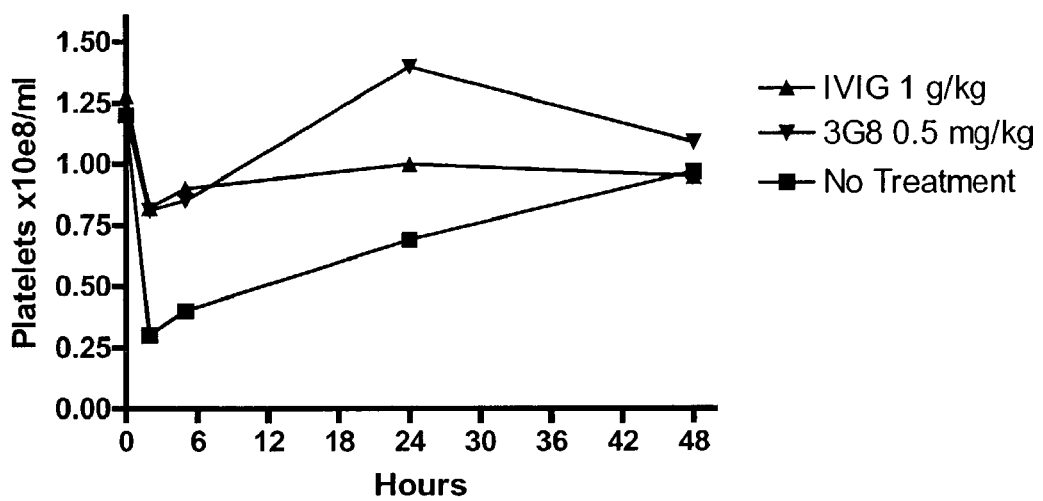
FIG. 5 shows ITP protection in mice injected i.v. with mAb 3G8 (0.5 μg/g) or human IVIG (1 mg/g) one hour before ch6A6 i.p. injection.
Figure 6:
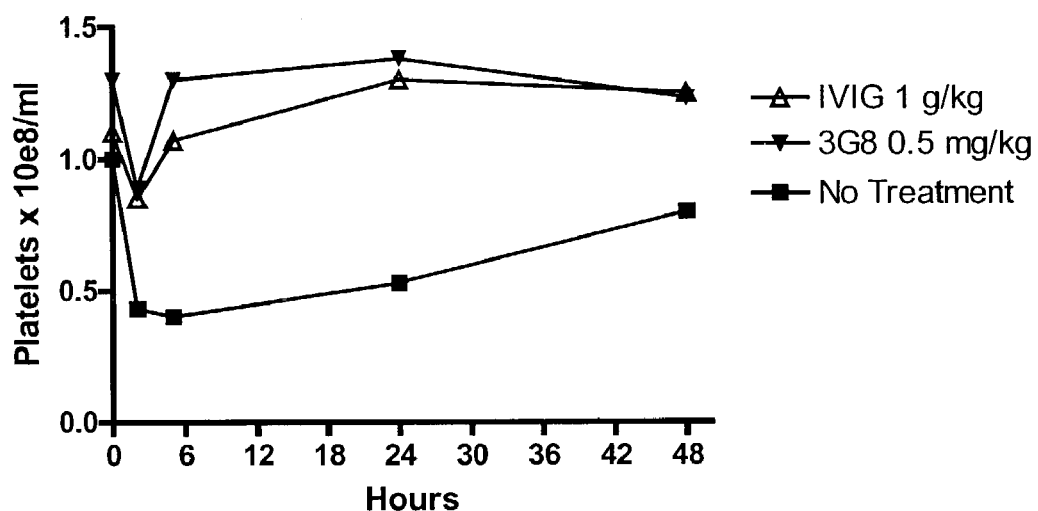
FIG. 6 shows ITP protection in mice injected i.v. with mAb 3G8 (0.5 μg/g) or human IVIG (1 mg/g) one hour before ch6A6 i.v. injection.

When muFcγRIII$^{-/-}$, huFcγRIIIA transgenic mice were injected with murine 3G8 (0.5 µg/g) one hour before i.p. injection of ch6A6, 33% of the platelets were depleted at the 2 hours time point (FIG. 5). The number of platelets then progressively increased to return to normal 24 hours after ch6A6 injection. When muFcγRIII$^{-/-}$, huFcγRIIIA transgenic mice were injected with murine 3G8 (0.5 µg/g) one hour before i.v. injection of ch6A6, 30% of the platelets were depleted at the 2 hours time point (FIG. 6). The number of platelets then rapidly increased to return to normal 5 hours after ch6A6 injection.

These results were similar to the protection seen when human IVIG is administered. When muFcγRIII$^{-/-}$, huFcγRIIIA transgenic mice were injected with human IVIG (1 mg/g) one hour before i.p. injection of ch6A6, 33% of the platelets were depleted at the 2 hours time point (FIG. 5). The number of platelets then progressively increased to return to normal 24 hours after ch6A6 injection. When muFcγRIII$^{-/-}$, huFcγRIIIA transgenic mice were injected with human IVIG (1 mg/g) one hour before i.v. injection of ch6A6, 20% of the platelets were depleted at the 2 hours time point (FIG. 6). The number of platelets then rapidly increased to return to normal 5 hours after ch6A6 injection.

The results shown in FIGS. 5 and 6 show that m3G8 protects mice from ch6A6-mediated platelet depletion, and that the level of protection was similar to the protection conferred by IVIG.

Figure 7:
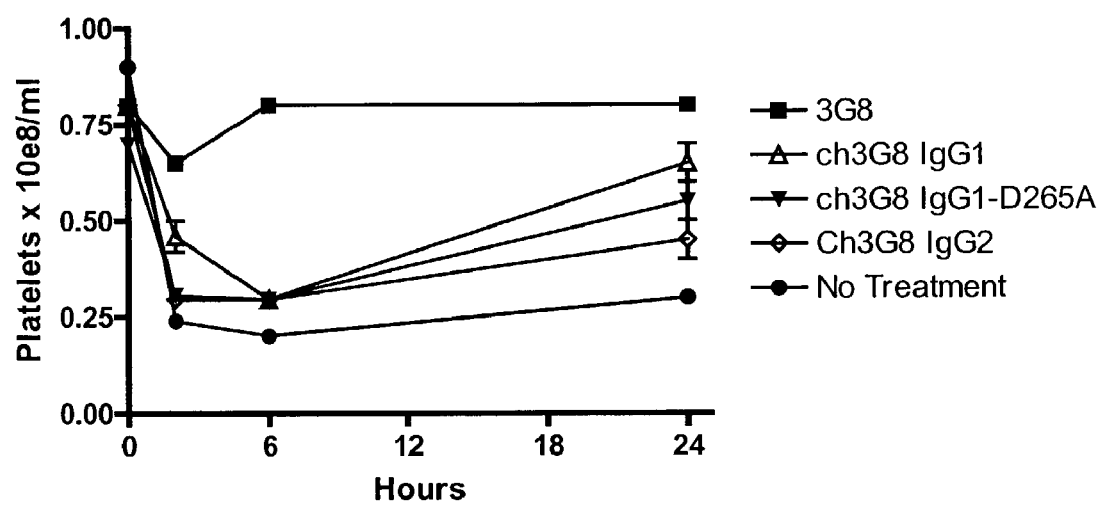
FIG. 7 shows the absence of ITP protection in mice injected i.v. with ch3G8 (0.5 μg/g) one hour before 6A6 i.p. injection.

Preparations of recombinant mouse 3G8 produced in HEK-293 cells, chimeric 3G8 with human IgG1 or IgG2 constant domains (ch3G8-γ1 produced in HEK-293 and CHO-K1 cells, and ch3G8-γ2 produced in HEK-293 cells), and a ch3G8-γ1 variant (ch3G8-γ1 D265A) did not provide significant protection in this experiment. When muFcγRIII$^{-/-}$, huFcγRIIIA transgenic mice were injected with ch3G8γ1 or γ2 (0.5 μg/g) one hour before i.p. injection of 6A6, approximately 60% of the platelets were depleted at the 5 hour time point (FIG. 7). The number of platelets then progressively returned to normal. Although depletion was not as severe as in mice that received no anti-CD16A binding protein, these chimeric antibodies provided significantly less protection, if any, than murine 3G8. A ch3G8 variant in which aspartic acid 265 was changed to alanine showed similar results. Interestingly, as is shown in Example 11, modification of the ch3G8 to produce an aglycosylated variant increased the protective effect of the antibody.

Example 11

Ch3G8 N297Q Protects Mice from ch6A6-Mediated Platelet Depletion

An aglycosylated version of ch3G8-γ1 was prepared by mutating the expression polynucleotide encoding ch3G8-γ1 so that residue 297 was changed from asparagine (N) to glutamine acid (Q), and expressing the encoded antibody. Residue 297 lies in an N-linked glycosylation site, and this mutation prevents glycosylation of the Fc domain at this site. This aglycosylated antibody, ch3G8 N297Q, was produced in HEK-293 cells as described for ch3G8-γ1 (see Example 4, supra). The ability of ch3G8-N297Q to protect against ch6A6-mediated platelet depletion was tested using the protocol described above.

Figure 8:
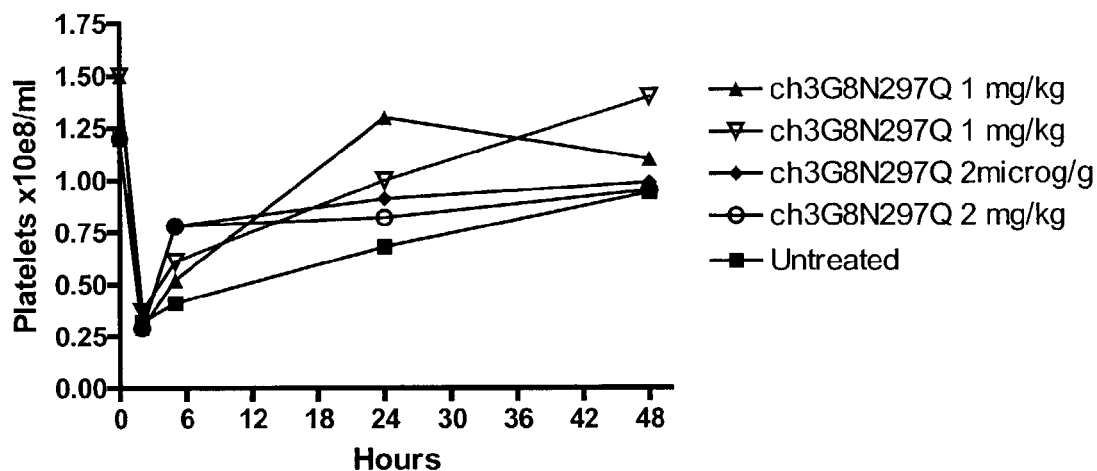
FIG. 8 shows protection from ITP in mice injected i.v. with ch3G8 N297Q one hour before ch6A6 i.p. injection.

When muFcγRIII$^{-/-}$, huFcγRIIIA transgenic mice were injected with 1 μg/g of the aglycosyl form of ch3G8 (ch3G8 N297Q) one hour before i.p. injection of ch6A6, approximately 75% of the platelets were depleted at the 2-hour time point (FIG. 8). Platelet levels increased faster than in the absence of ch3G8 N297Q, and returned to normal by 24 hours after ch6A6 injection.

Figure 9:
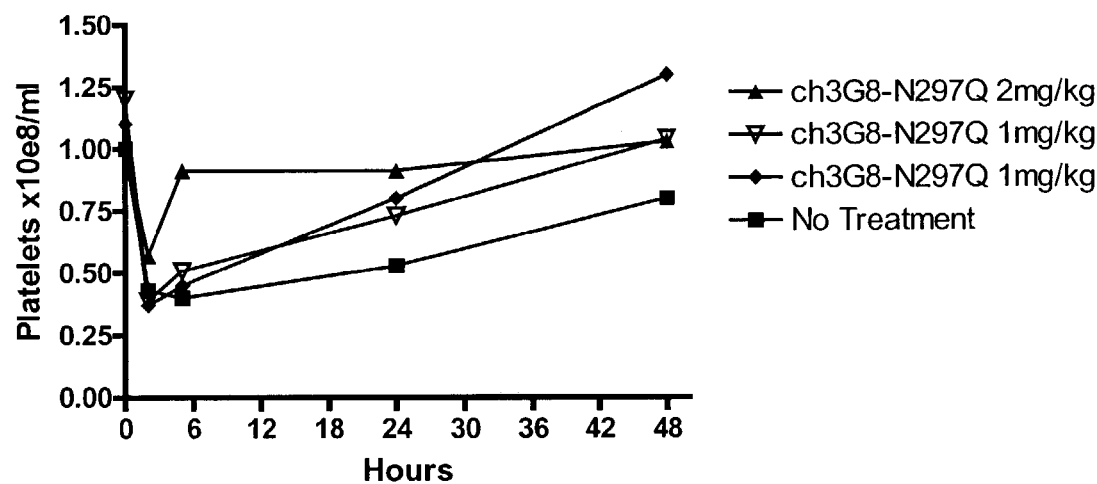
FIG. 9 shows protection from ITP in mice injected i.v. with ch3G8 N297Q one hour before ch6A6 i.v. injection.

When muFcγRIII$^{-/-}$, huFcγRIIIA transgenic mice were injected with 1 μg/g ch3G8 N297Q one hour before i.v. injection of ch6A6, approximately 60% of the platelets were depleted at the 2 hours time point (FIG. 9). Platelet levels increased faster than in the absence of ch3G8 N297Q, and returned to normal by 48 hours after ch6A6 injection.

When muFcγRIII$^{-/-}$, huFcγRIIIA transgenic mice were injected with ch3G8 N297Q (2 μg/g) one hour before i.v. injection of ch6A6, only 40% of the platelets were depleted at the 2 hours time point (FIG. 9). Platelet levels increased faster than in the absence of ch3G8 N297Q, and returned to normal by 5 hours after ch6A6 injection.

Thus, ch3G8-N297Q was consistently able to significantly improve platelet counts. Binding of 3G8 to human CD16 on effector cells blocks the ability of CD16 to interact with immune complexes and trigger effector functions such as ADCC or phagocytosis. Chimeric and mouse 3G8 molecules have similar ability to bind CD16 and are similar in their ability to inhibit the binding of sCD16 to immune complexes in vitro. Without intending to be bound by a particular mechanism, the binding (and thus) the blocking activity of the mAb is thought to be confined to the Fab portion of the antibody and blocking of huCD16 is believed to be the mechanism of protection in the transgenic mouse ITP model. The data above suggest that the glycosylation state of the Fc domain can affect the in vivo protective capacity of anti-CD16A antibodies. Ablation of Fc domain glycosylation (e.g., with D265A or N297Q mutations, or by using a human gamma2 Fc domain) reduces or eliminates Fc binding to FcR. In the case of the aglycosyl (N297Q) variant, complement fixation is also abolished.

Example 12

Neutrophil Levels Following Administration of Aglycosyl CD16A Binding Proteins

The effect of an aglycosylated CD16A binding protein on neutrophil levels was tested and compared to that of glycosylated CD16A binding proteins. CD16A binding proteins, or the controls such as irrelevant human IgG1 (negative control) or murine RB6-8C5 (positive control), were administered to groups of muFcγRIII$^{-/-}$, huFcγRIIIB transgenic mice at a concentration of 5 μg/g in phosphate buffered saline (PBS). Another negative control was administered PBS alone. Twenty four hours later, mice were euthanized and blood, spleen and bone marrow were collected. Neutrophils were analyzed by FACS. Staining experiments were performed in RPMI containing 3% FCS. Murine cells were stained using FITC-conjugated 3G8 (PharMingen) and R-PE-conjugated RB6-8C5 (PharMingen). Samples were analyzed by flow-cytometry using a FACSCALIBUR™ (Becton Dickinson).

Figure 10:
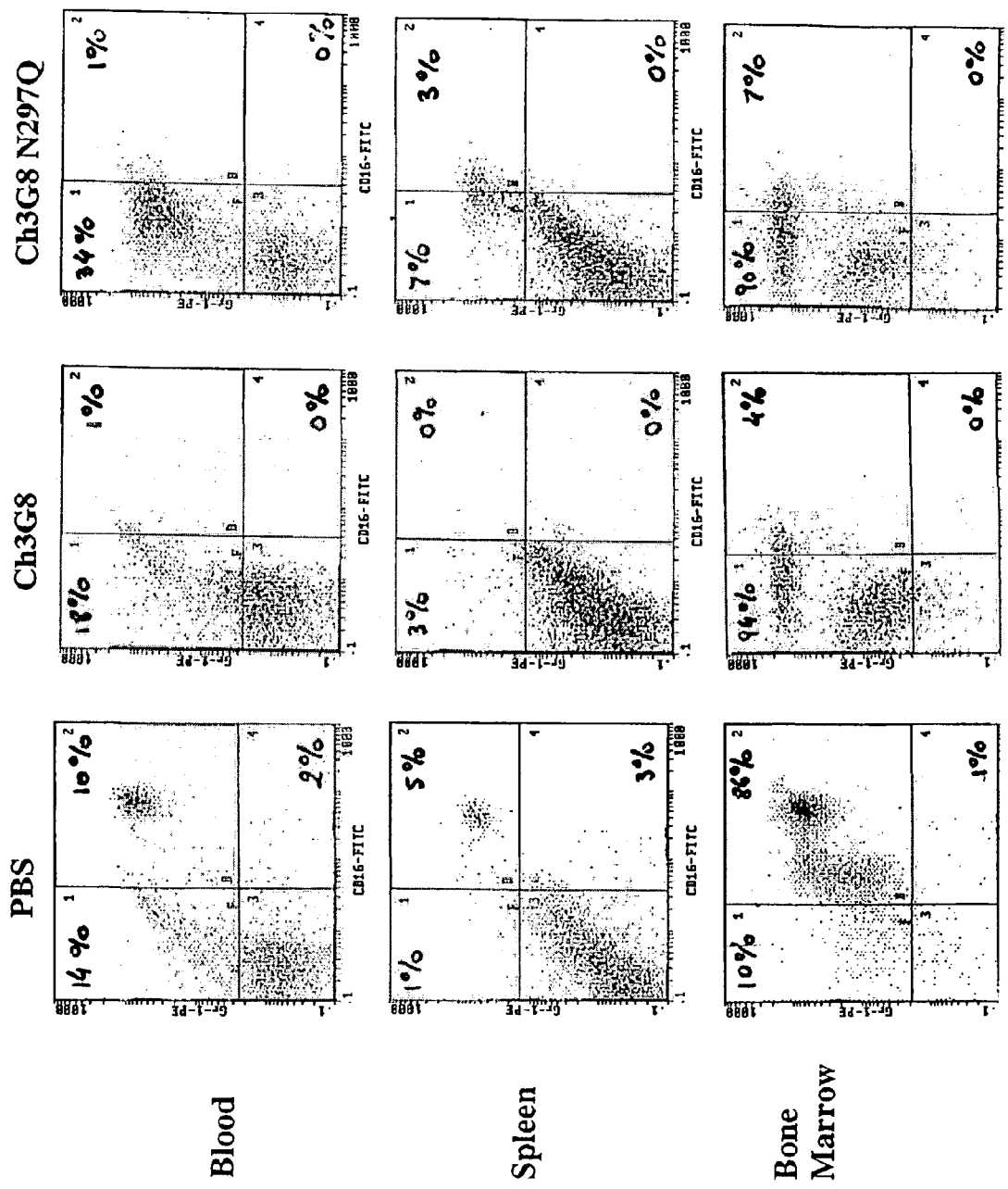
FIG. 10 shows the results of FACS scans of neutrophils following administration of CD16A binding protein or controls. The x-axis shows labeling with antibody to CD16, and the y-axis shows labeling with antibody to the Gr-1 antigen. The upper right quadrant shows neutrophils; the upper left quadrant shows other granulocytes and neutrophils that no longer stain with 3G8-FITC.

Intraperitoneal injection of 5 μg/g ch3G8 (prepared as described above) resulted in murine neutrophil depletion in the blood and spleen (FIG. 10; upper right quadrant). Similar results were seen following administration of murine 3G8 (results not shown). In the bone marrow of ch3G8 treated animals, neutrophils stained weakly for CD16, which could indicate receptor occupancy by the chimeric antibody or shedding (FIG. 10; see shift from the upper right quadrant to the upper left quadrant). In contrast, intraperitoneal injection of 5 μg/g ch3G8 N297Q did not result in murine neutrophil depletion in the blood, spleen or bone marrow (FIG. 10). In additional experiments, humanized glycosylated 3G8 antibodies showed substantially more depletion of circulating blood neutrophils compared to aglycosylated forms of the same antibodies.

Example 13

Autoimmune Hemolytic Anemia Model

This example demonstrates that administration of CD16A binding protein prevents red blood cell depletion in a model of autoimmune hemolytic anemia.

Figure 11:
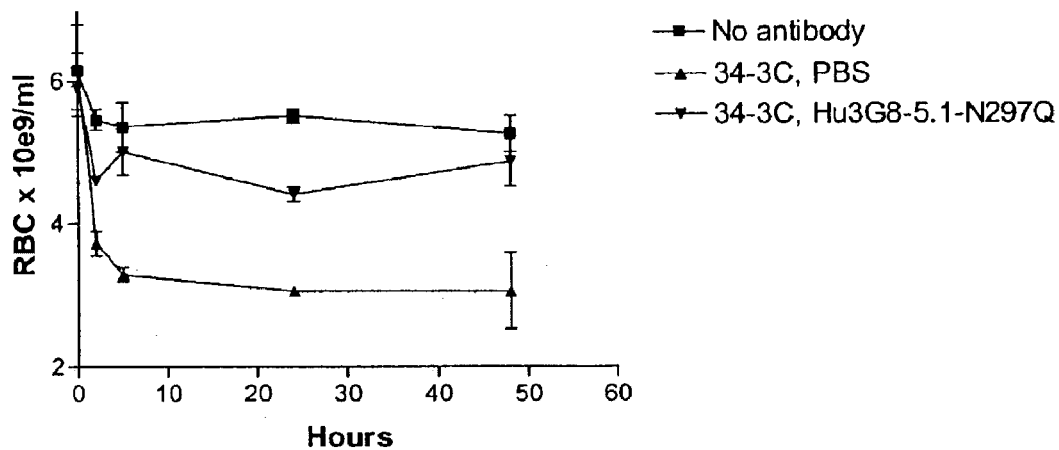
FIG. 11 shows prevention of AIHA with a humanized anti-CD16 antibody.

The ability of the Hu3G8-5.1-N297Q monoclonal antibody to prevent antibody-dependent red blood cell depletion in muFcRIII−/−, huFcRIIIa+ mice was evaluated. Hu3G8-5.1-N297Q is an aglycosy antibody with the heavy chain Hu3G8VH-5 and the light chain Hu3G8VH-1 and the indicated substitution of asparagine 297. Mice were bled on day 0 and RBC levels were determined using a Z2™ COULTER COUNTER® particle analyzer. The next day groups of 3 animals each were then injected intravenously with either 0.5 mg/kg Hu3G8-5.1-N297Q or PBS. One group of mice did not receive any compound. One hour later, RBC depletion was induced in the first two groups by administering mouse anti-RBC IgG2a Mab 34-3C to each animal intraperitoneally (i.p.) (2.5 mg/kg). Animals were bled 2 hrs, 5 hrs, 24 hrs and 48 hrs after administration of 34-3C and RBC counts were determined. Data was analyzed by plotting RBC count versus. The data, depicted in FIG. 11, demonstrate the ability of Hu3G8-5.1-N297Q to prevent RBC depletion in this model.

Example 14

Inhibition of Antibody-Dependent Cellular Cytotoxicity (ADCC)

This example demonstrates that humanized 3G8 variants inhibit ADCC in vitro and with an activity similar to that of mouse 3G8.

Methods: The protocol for assessment of antibody dependent cellular cytotoxicity (ADCC) is similar to that previously described in (Ding et al., 1998, *Immunity* 8:403-11). Briefly, target cells from the HER2-overexpressing breast cancer cell line SK-BR-3 were labeled with the europium chelate bis(acetoxymethyl)2,2':6',2''-terpyridine-6,6''-dicarboxylate (DELFIA® BATDA Reagent, Perkin Elmer/Wallac). The labeled target cells were then opsonized (coated) with either chimeric anti-HER2 (ch4D5, 100 ng/ml) or chimeric anti-fluorescein (ch4-4-20, 1 ug/ml) antibodies. In the case of the anti-fluorescein antibody, SK-BR-3 cells were coated with the fluorescein hapten prior to antibody opsonization. Peripheral blood mononuclear cells (PBMC), isolated by FICOLL-PAQUE™ (Amersham Pharmacia) gradient centrifugation, were used as effector cells (Effector:Target ratio: ch4D5=(37.5:1) and ch4-4-20=(75:1)). Following a 3.5 hour incubation at 37° C., 5% CO2, cell supernatants were harvested and added to an acidic europium solution (DELFIA® Europium Solution, Perkin Elmer/Wallac). The fluorescence of the Europium-TDA chelates formed was quantitated in a time-resolved fluorometer (VICTOR$^2$ 1420, Perkin Elmer/Wallac). Maximal release (MR) and spontaneous release (SR) were determined by incubation of target cells with 2% TX-100 and media alone, respectively. Antibody independent cellular cytotoxicity (AICC) was measured by incubation of target and effector cells in the absence of antibody. Each assay is performed in triplicate. The mean percentage specific lysis was calculated as: (ADCC−AICC)/(MR−SR)×100.

Figure 12:
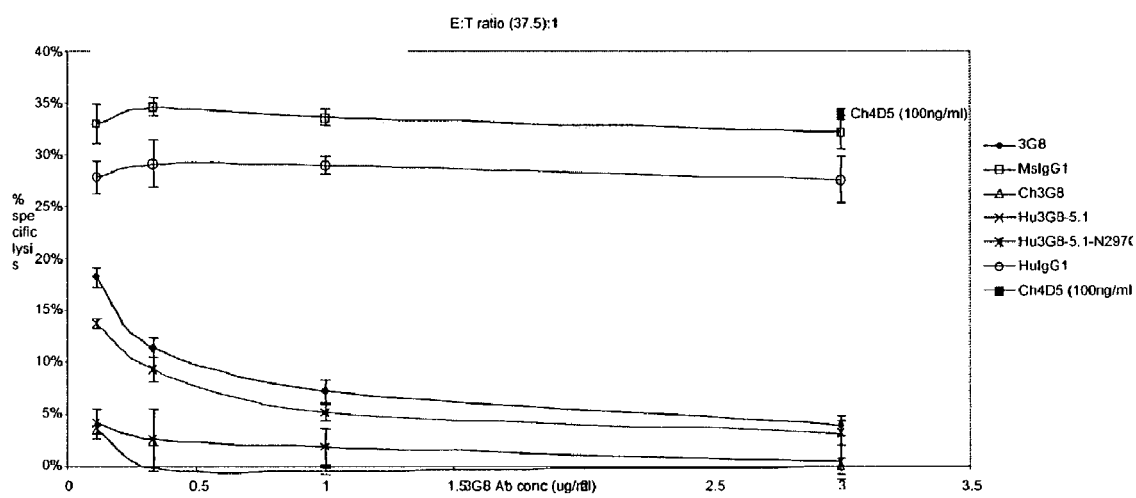
FIG. 12 shows inhibition of ch4D5 mediated ADCC by humanized 3G8 antibodies.
Figure 13A:
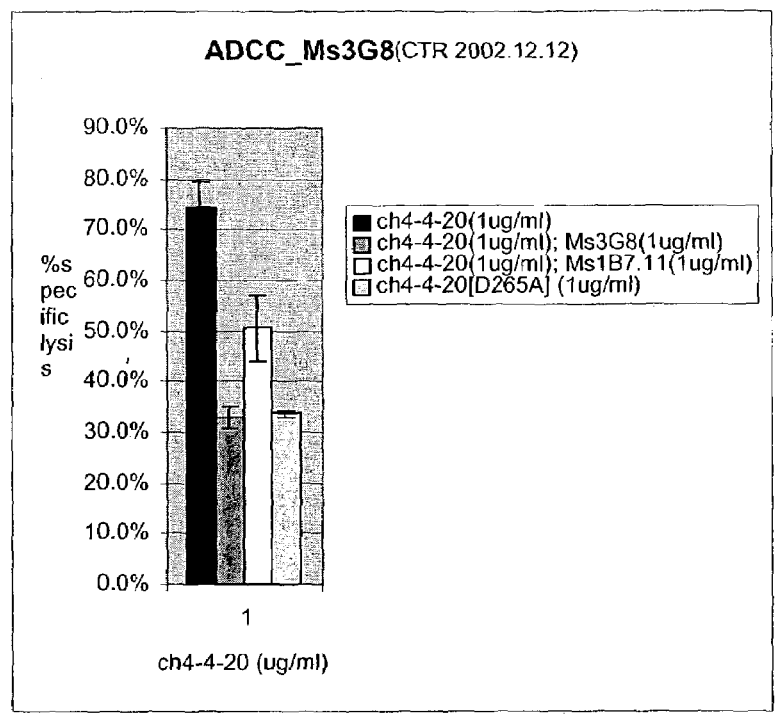
FIGS. 13A-B show inhibition of ch4-4-20 mediated ADCC by mouse 3G8 (FIG. 13A) and humanized 3G8 antibodies (FIG. 13B).
Figure 13B:
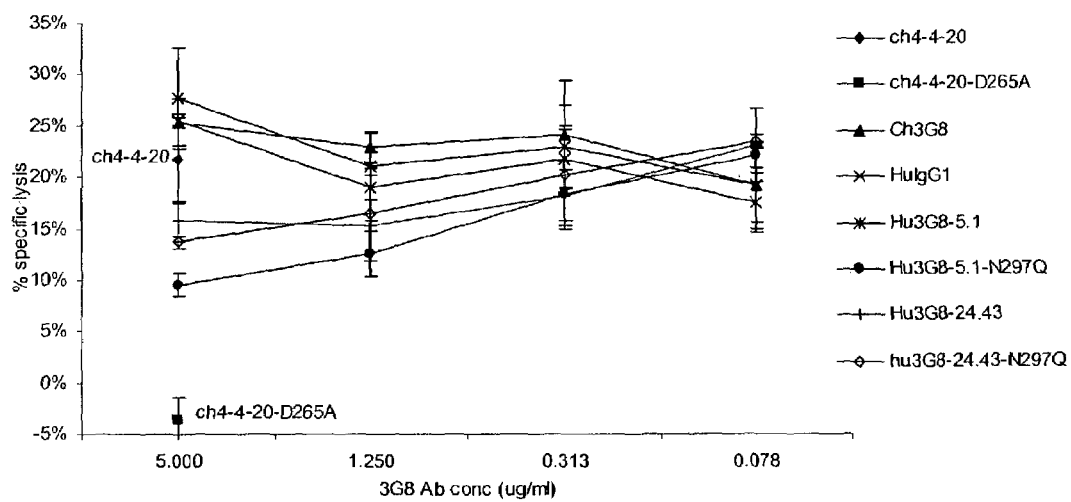

Results: Addition of anti-CD16 variants inhibited ADCC mediated through antibodies directed against the HER2/neu protein (ch4D5) (FIG. 12), or the hapten, fluorescein (ch4-4-20) (FIG. 13). Inhibition of the ch4D5 mediated ADCC was greater than 50% at 300 ng/ml for all 3G8 variants tested while isotype control antibodies had no effect in the assay. In the case of the anti-fluorescein antibody, inhibition was approximately 50% at concentrations above 1 ug/ml for murine 3G8 (FIG. 13A) and humanized 3G8 variants (FIG. 13B), while isotype control antibodies and chimeric 3G8 had little effect.

Example 15

Administration of Hu3G8-5.1-N297Q Prevents Immune Thrombocytopenia (ITP) in huFcRIIa+, huFcRIIIa+Mice This example shows that that administration of anti-CD16A antibodies protects against ITP mediated by CD32A. As in FcγRIII−/−, hCD16A mice, administration of the ch6A6 antibody induces ITP in FcγRIII−/−, hCD32A transgenic mice. Five hours after injection of 0.1 μg/g ch6A6 i.p., approximately 80% of the platelets are depleted (not shown). The number of platelets remained low for 24 hours after ch6A6 injection, and then progressively increased to return to normal 48 hours after ch6A6 injection. As expected, the i.v. injection of hu3G8-5.1 (0.5 μg/g) one hour prior to ch6A6 injection did not protect FcγRIII−/−, hCD32A mice against ITP (not shown).

Figure 14:
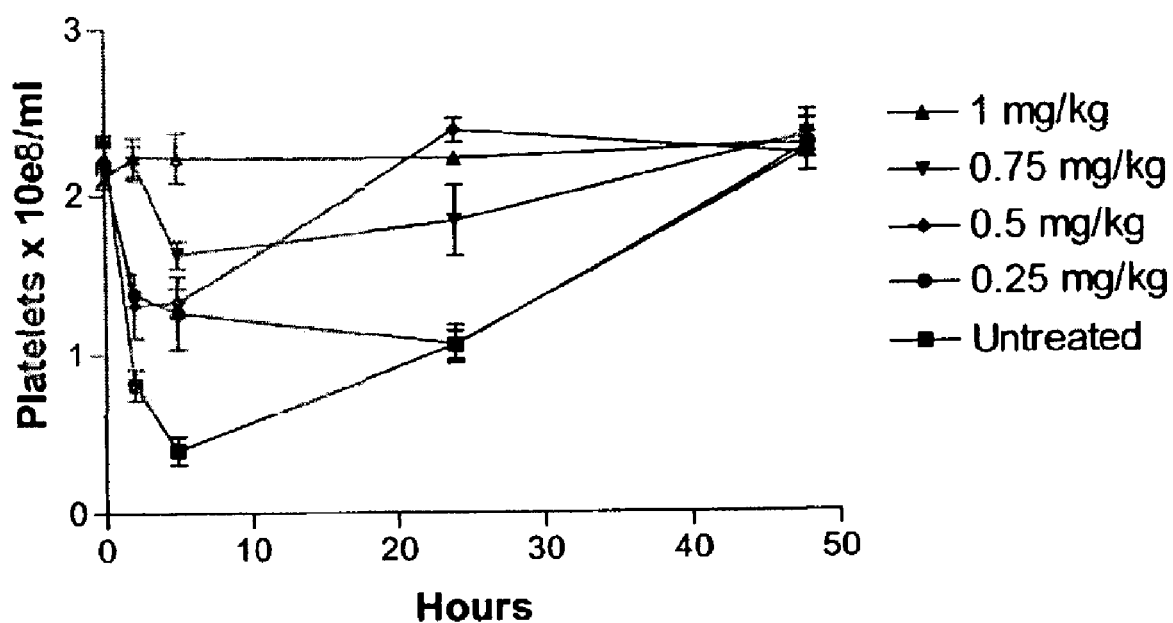
FIG. 14 shows protection of FcγRIII–/–, hCD16A, hCD32A mice against ITP by administration of hu3G8-5.1.

As in single transgenic mice, ch6A6 induces ITP in FcγRIII−/−, hCD16A, hCD32A double transgenic mice. Five hours after injection of 0.1 μg/g ch6A6 i.p., approximately 80% of the platelets were depleted (FIG. 14). The number of platelets remained low for 24 hours after ch6A6 injection, and then progressively increased to return to normal 48 hours after ch6A6 injection.

In contrast to FcγRIII−/−, hCD32A mice, FcγRIII−/−, hCD16A, hCD32A mice were protected against ITP by administration of hu3G8-5.1. Complete protection was observed when 1 μg/g h3G8 5.1 is injected one hour prior to ch6A6 i.p. injection; and partial protection resulted from administration of 0.75 μg/g or 0.5 μg/g of h3G8-5.1. (FIG. 14). Thus, the data indicate that although CD32A can mediate ITP, the injection of 1 μg/g of h3G8-5.1 completely and unexpectedly protects mice against platelet depletion.

Example 16

Figure 15A:
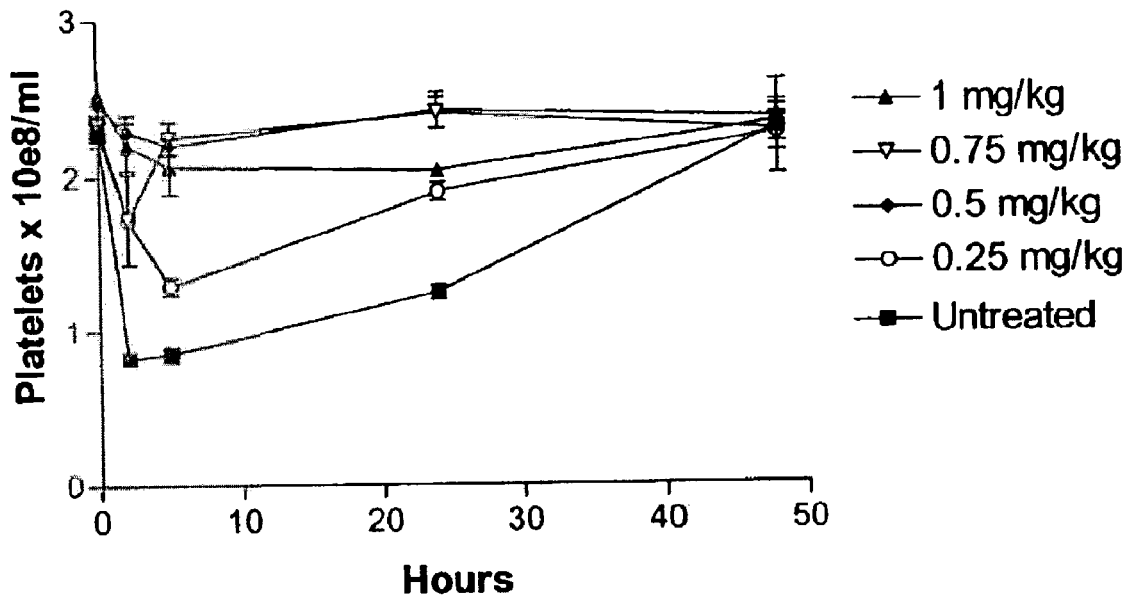
FIGS. 15A-B show protection of FcγRIII–/–, hCD16A mice against ITP by administration of hu3G8-5.1 N297Q.
Figure 15B:
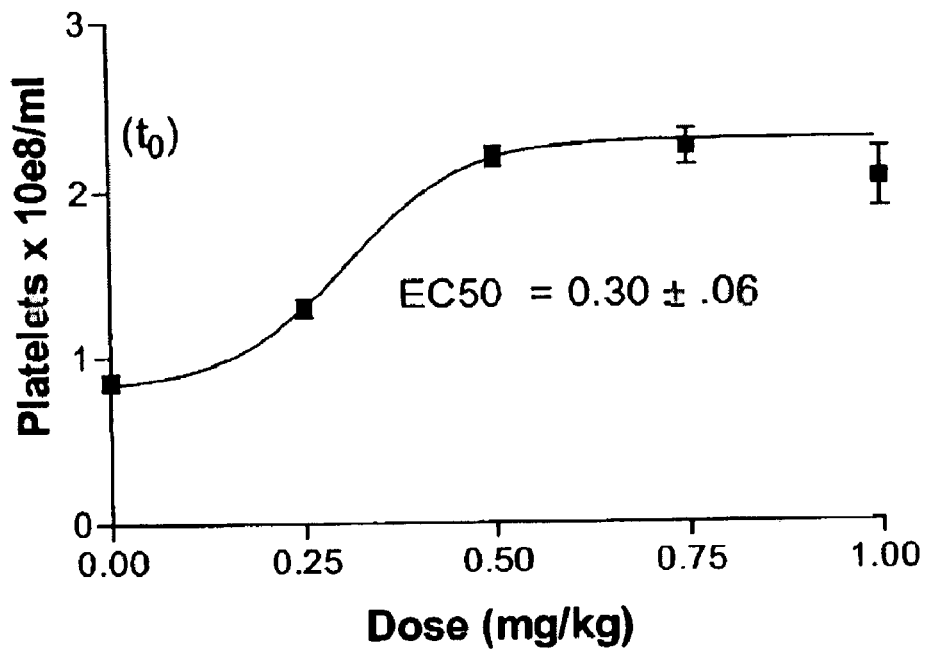

Prevention of Platelet Depletion Using Hu3G8-5.1-N297Q Produced in CHO-S Cell Line Hu3G8-5.1-N297Q was produced in a CHO-S cell line. The ability of this antibody to protect against ITP in FcγRIII−/−, hCD16A single transgenic mice was determined using the procedure described in Example 13. As is shown in FIG. 15, administration of 0.5 mg/kg or more Hu3G8-5.1-N297Q produced in CHO-S cells one hour prior to ch6A6 i.p. injection completely protects mice against ITP.

Example 17

Therapeutic Effect of Aglycosylated Humanized Antibodies

Figure 16A:
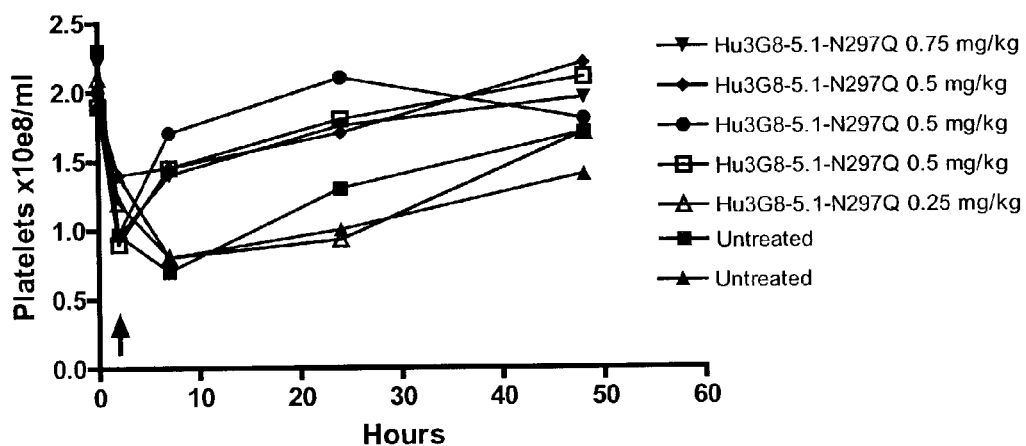
FIGS. 16A-B show the therapeutic effect of administration of aglycosylated humanized antibody subsequent to mice in which thrombocytopenia has been induced.

ITP was induced in mice as described above, by i.p. injection of 0.1 ug/g ch6A6 at time 0. Two hours later, the number of platelets in the plasma was determined to confirm the presence of ITP. Three hours after i.p. injection of ch6A6, mice were injected i.v. with hu3G8-5.1-N297Q at different concentration (arrow). The results (FIG. 16A) indicate that the number of platelets rapidly returns to normal after Hu3G8-5.1-N297Q injection whereas the number of platelets remains low in non-treated mice. These results demonstrate that administration of the hu3G8-5.1-N297Q antibody can be used to cure ITP in the mouse model.

Figure 16B:
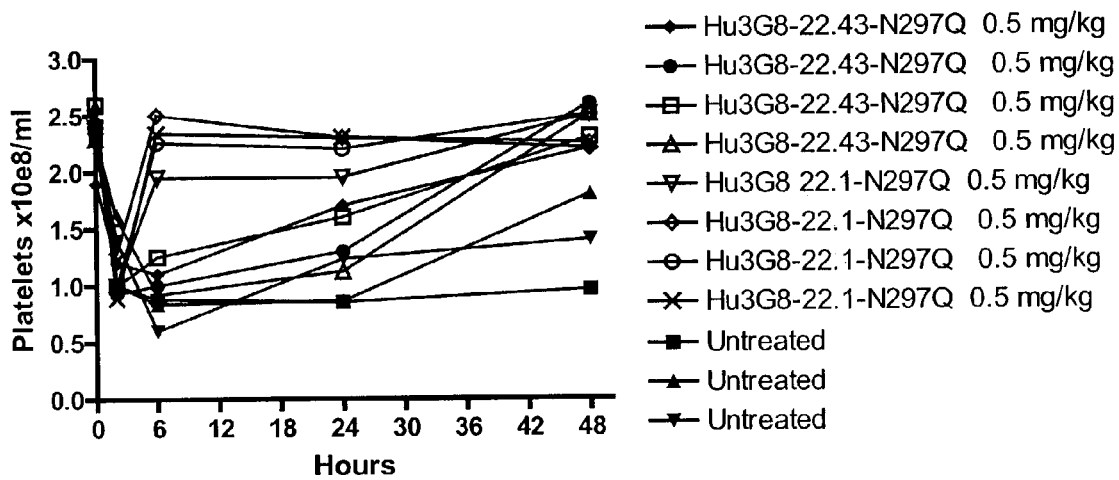

In this experiment, ITP was induced by i.p. injection of 0.1 ug/g ch6A6 at time 0. Two hours later, the number of platelets in the plasma was determined to confirm the presence of ITP. Three hours after i.p. injection of ch6A6, mice were injected i.v. with hu3G8-22.1-N297Q or hu3G8-22.43-N297Q at 0.5 ug/g (arrow). The results indicate that the number of platelets rapidly returns to normal after Hu3G8-22.1-N297Q injection whereas the number of platelets remains low in non-treated mice and in mice treated with Hu3G8-22.43-N297Q (FIG. 16B). These data indicate that hu3G8-22.1-N297Q can be used to cure ITP in the mouse model.

Example 18

Figure 17:
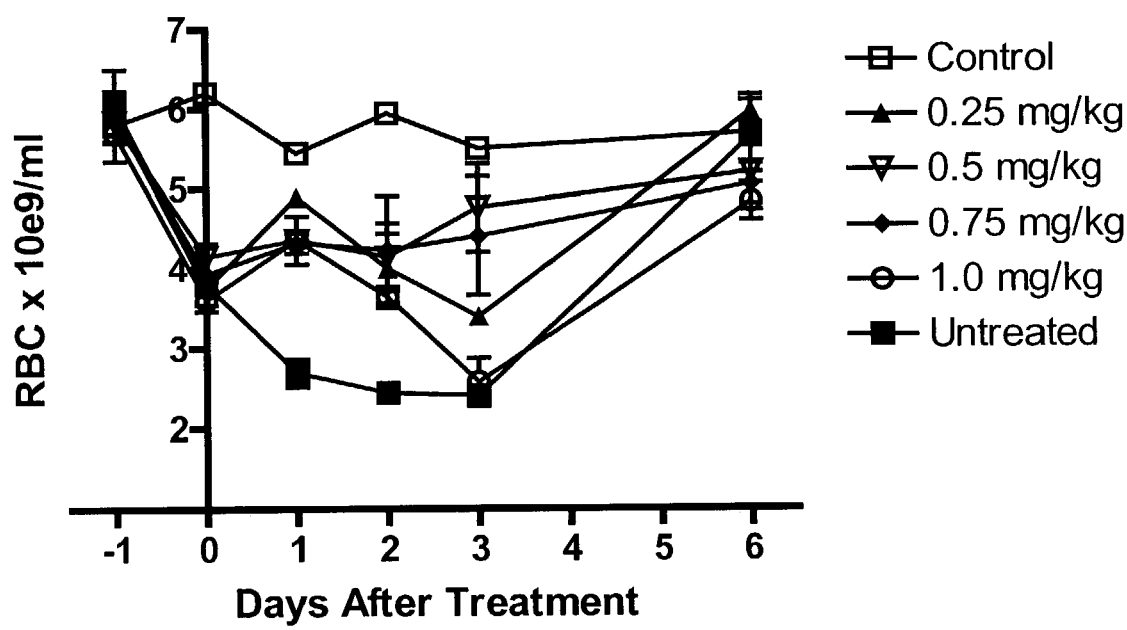
FIG. 17 shows the therapeutic effect of a humanized anti-CD16A antibody in treatment of autoimmune hemolytic anemia.

Therapeutic Effect of Hu3G8-22.1-N297Q in AHA in muFcγRIII−/−, huFcγRIIIA Transgenic Mice In this experiment, AHA was induced by i.p. injection of 50 ug mouse anti-RBC IgG2a Mab 34-3C at day 0. On day 1, the number of RBC in the blood was determined to confirm the presence of AHA. Two hours later, mice were injected i.v. with Hu3G8-22.1-N297Q at various concentrations (arrow). The results indicate that the number of RBC remained stable after Hu3G8-22.1-N297Q injection whereas the number of RBC continued to drop in non-treated mice (FIG. 17). The optimal concentration of Hu3G8-22.1-N297Q is 0.5 ug/g. The number of RBC returned to normal in all mice at day 7. Control mice were bled every day but not injected in order to determine the effect of repeated bleedings on the number of RBC. These results in the mouse model indicate that Hu3G8-22.1-N297Q can be used to cure AHA. Hu3G8-22.1-N297Q prevents further RBC depletion by autoantibodies and therefore protects mice against anemia.

TABLE 3A*

| | FR1 | CDR1 | FR2 | CDR2 | FR3 | CDR3 | FR4 |
|---|---|---|---|---|---|---|---|
| 3G8VH | A | A | A | A | A | A | A |
| Ch3G8VH | A | A | A | A | A | A | B |
| HxC | B | A | B | A | A | A | B |
| CxH | A | A | A | A | B | A | B |
| Hu3G8VH-1 | B | A | B | A | B | A | B |
| Hu3G8VH-2 | C | A | B | A | B | A | B |
| Hu3G8VH-3 | D | A | B | A | B | A | B |
| Hu3G8VH-4 | B | A | B | A | C | B | B |
| Hu3G8VH-5 | B | A | B | A | C | A | B |
| Hu3G8VH-6 | B | B | B | A | B | B | B |
| Hu3G8VH-7 | B | B | B | A | B | A | B |
| Hu3G8VH-8 | B | A | B | A | B | C | B |
| Hu3G8VH-9 | B | A | B | B | B | B | B |
| Hu3G8VH-10 | B | A | B | A | B | B | B |
| Hu3G8VH-11 | B | A | B | B | B | A | B |
| Hu3G8VH-12 | B | A | B | C | B | A | B |
| Hu3G8VH-13 | B | A | B | D | B | A | B |
| Hu3G8VH-14 | B | A | B | E | B | A | B |
| Hu3G8VH-15 | B | A | B | A | D | A | B |
| Hu3G8VH-16 | B | A | B | A | E | A | B |
| Hu3G8VH-17 | B | A | B | A | F | A | B |
| Hu3G8VH-18 | B | A | B | A | G | A | B |
| Hu3G8VH-19 | B | A | B | A | C | C | B |
| Hu3G8VH-20 | B | B | B | C | B | A | B |
| Hu3G8VH-21 | B | A | B | A | D | B | B |
| Hu3G8VH-22 | B | B | B | C | B | C | B |
| Hu3G8VH-23 | B | B | B | C | E | C | B |
| Hu3G8VH-24 | B | B | B | C | F | C | B |
| Hu3G8VH-25 | B | B | B | C | G | C | B |
| Hu3G8VH-26 | B | B | B | C | C | C | B |
| Hu3G8VH-27 | B | B | B | C | E | D | B |
| Hu3G8VH-28 | B | B | B | C | F | D | B |
| Hu3G8VH-29 | B | B | B | C | G | D | B |
| Hu3G8VH-30 | B | B | B | C | C | D | B |
| Hu3G8VH-31 | E | B | B | C | B | A | B |
| Hu3G8VH-32 | E | B | B | H | B | A | B |
| Hu3G8VH-33 | E | B | B | H | B | A | B |
| Hu3G8VH-34 | E | B | B | C | B | C | B |
| Hu3G8VH-35 | E | B | B | C | C | C | B |
| Hu3G8VH-36 | E | B | B | H | C | D | B |
| Hu3G8VH-37 | E | B | B | H | E | C | B |
| Hu3G8VH-38 | E | B | B | F | B | A | B |
| Hu3G8VH-39 | E | B | B | I | B | A | B |
| Hu3G8VH-40 | E | B | B | G | B | A | B |
| Hu3G8VH-41 | E | B | B | J | B | A | B |
| Hu3G8VH-42 | E | B | B | C | H | A | B |
| Hu3G8VH-43 | E | B | B | C | H | C | B |
| Hu3G8VH-44 | E | B | B | C | I | D | B |
| Hu3G8VH-45 | E | B | B | C | J | D | B |

*Letters in Table 3A refer to sequences in Tables 3B-H.

TABLE 3B

| | | FR1 | | | |
|---|---|---|---|---|---|
| A | B | C | D | E | RESIDUE |
| Q | Q | Q | Q | Q | 1 |
| V | V | V | V | I | 2 |
| T | T | T | T | T | 3 |
| L | L | L | L | L | 4 |
| K | R | K | R | K | 5 |
| E | E | E | E | E | 6 |
| S | S | S | S | S | 7 |
| G | G | G | G | G | 8 |
| P | P | P | P | P | 9 |
| G | A | A | A | T | 10 |
| I | L | L | L | L | 11 |
| L | V | V | V | V | 12 |
| Q | K | K | K | K | 13 |
| P | P | P | P | P | 14 |
| S | T | T | T | T | 15 |
| Q | Q | Q | Q | Q | 16 |
| T | T | T | T | T | 17 |
| L | L | L | L | L | 18 |
| S | T | T | T | T | 19 |
| L | L | L | L | L | 20 |
| T | T | T | T | T | 21 |
| C | C | C | C | C | 22 |
| S | T | T | T | T | 23 |
| F | F | F | F | F | 24 |
| S | S | S | S | S | 25 |
| G | G | G | G | G | 26 |
| F | F | F | F | F | 27 |
| S | S | S | S | S | 28 |
| L | L | L | L | L | 29 |
| R | S | S | R | S | 30 |
| 30 | 31 | 32 | 33 | 34 | Seq ID No |

TABLE 3C

| | CDR1 | |
|---|---|---|
| A | B | RESIDUE |
| T | T | 31 |
| S | S | 32 |
| G | G | 33 |
| M | V | 34 |
| G | G | 35 |
| V | V | 35A |
| G | G | 35B |
| 35 | 36 | Seq ID No |

TABLE 3D

| | FR2 | |
|---|---|---|
| A | B | RESIDUE |
| W | W | 36 |
| I | I | 37 |
| R | R | 38 |
| Q | Q | 39 |
| P | P | 40 |

TABLE 3D-continued

FR2

| A | B | RESIDUE |
|---|---|---------|
| S | P | 41 |
| G | G | 42 |
| K | K | 43 |
| G | A | 44 |
| L | L | 45 |
| E | E | 46 |
| W | W | 47 |
| L | L | 48 |
| A | A | 49 |
| 37 | 38 | Seq ID No. |

TABLE 3E

CDR2

| A | B | C | D | E | F | G | H | I | J | RESIDUE |
|---|---|---|---|---|---|---|---|---|---|---------|
| H | H | H | H | H | L | H | L | H | L | 50 |
| I | I | I | I | I | I | I | I | I | I | 51 |
| W | Y | W | Y | W | D | W | D | W | W | 52 |
| W | W | W | W | W | W | W | W | W | W | 53 |
| D | N | D | D | N | D | D | D | D | N | 54 |
| D | D | D | D | D | D | D | D | D | D | 55 |
| D | D | D | D | D | D | D | D | D | D | 56 |
| K | K | K | K | K | K | K | K | K | K | 57 |
| R | R | R | R | R | R | R | R | R | R | 58 |
| Y | Y | Y | Y | Y | Y | Y | Y | Y | Y | 59 |
| N | N | S | N | N | S | S | S | S | S | 60 |
| P | P | P | P | P | P | P | P | P | P | 61 |
| A | A | S | A | A | S | S | S | S | S | 62 |
| L | L | L | L | L | L | L | L | L | L | 63 |
| K | K | K | K | K | K | K | K | K | K | 64 |
| S | S | S | S | S | S | S | S | S | S | 65 |
| 39 | 40 | 41 | 42 | 43 | 44 | 45 | 46 | 47 | 48 | Seq ID No |

TABLE 3F

FR3

| A | B | C | D | E | F | G | H | I | J | RESIDUE |
|---|---|---|---|---|---|---|---|---|---|---------|
| R | R | R | R | R | R | R | R | R | R | 66 |
| L | L | L | L | L | L | L | L | L | L | 67 |
| T | T | T | T | T | T | T | T | T | T | 68 |
| I | I | I | I | I | I | I | I | I | I | 69 |
| S | S | S | S | S | S | S | T | T | T | 70 |
| K | K | K | K | K | K | K | K | K | K | 71 |
| D | D | D | D | D | D | D | D | D | D | 72 |
| T | T | T | T | T | T | T | T | T | T | 73 |
| S | S | S | S | S | S | S | S | S | S | 74 |
| S | K | K | K | K | K | K | K | K | K | 75 |
| N | N | N | N | N | N | N | N | N | N | 76 |
| Q | Q | Q | Q | Q | Q | Q | Q | Q | Q | 77 |
| V | V | V | V | V | V | V | V | V | V | 78 |
| F | V | V | V | V | V | V | V | V | V | 79 |
| L | L | L | L | L | L | L | L | L | L | 80 |
| K | T | T | T | T | T | T | T | T | T | 81 |
| I | M | M | M | M | M | M | M | M | M | 82 |
| A | T | T | T | T | T | T | T | T | T | 82A |
| S | N | N | N | N | N | N | N | N | N | 82B |
| V | M | M | M | M | M | M | M | M | M | 82C |
| D | D | D | D | D | D | D | D | D | D | 83 |
| T | P | P | P | P | P | P | P | P | P | 84 |
| A | V | V | V | V | V | V | V | V | V | 85 |
| D | D | D | D | D | D | D | D | D | D | 86 |
| T | T | T | T | T | T | T | T | T | T | 87 |
| A | A | A | A | A | A | A | A | A | A | 88 |
| T | T | T | T | T | T | T | T | T | T | 89 |
| Y | Y | Y | Y | Y | Y | Y | Y | Y | Y | 90 |
| Y | Y | Y | Y | Y | Y | Y | Y | Y | Y | 91 |

TABLE 3F-continued

FR3

| A | B | C | D | E | F | G | H | I | J | RESIDUE |
|---|---|---|---|---|---|---|---|---|---|---------|
| C | C | C | C | C | C | C | C | C | C | 92 |
| A | A | A | A | A | A | A | A | A | A | 93 |
| Q | R | Q | T | K | A | H | R | H | Q | 94 |
| 49 | 50 | 51 | 52 | 53 | 54 | 55 | 56 | 57 | 58 | Seq ID No |

TABLE 3G

CDR3

| A | B | C | D | RESIDUE |
|---|---|---|---|---------|
| I | I | I | I | 95 |
| N | N | N | N | 96 |
| P | P | P | P | 97 |
| A | A | A | A | 98 |
| W | W | Y | Y | 99 |
| F | F | F | F | 100 |
| A | D | A | D | 101 |
| Y | Y | Y | Y | 102 |
| 59 | 60 | 61 | 62 | Seq ID No |

TABLE 3H

FR4

| A | B | RESIDUE |
|---|---|---------|
| W | W | 103 |
| G | G | 104 |
| Q | Q | 105 |
| G | G | 106 |
| T | T | 107 |
| L | L | 108 |
| V | V | 109 |
| T | T | 110 |
| V | V | 111 |
| S | S | 112 |
| A | S | 113 |
| 63 | 64 | Seq ID No |

TABLE 4A*

V_L SEQUENCES

| | FR1 | CDR1 | FR2 | CDR2 | FR3 | CDR3 | FR4 |
|---|---|---|---|---|---|---|---|
| 3G8VL | A | A | A | A | A | A | A |
| Ch3G8VL | A | A | A | A | A | A | A |
| Hu3G8VL-1 | B | A | A | A | B | A | B |
| Hu3G8VL-2 | B | B | A | A | B | A | B |
| Hu3G8VL-3 | B | C | A | A | B | A | B |
| Hu3G8VL-4 | B | D | A | A | B | A | B |
| Hu3G8VL-5 | B | E | A | A | B | A | B |
| Hu3G8VL-6 | B | F | A | A | B | A | B |
| Hu3G8VL-7 | B | G | A | A | B | A | B |
| Hu3G8VL-8 | B | A | A | B | B | A | B |
| Hu3G8VL-9 | B | A | A | C | B | A | B |
| Hu3G8VL-10 | B | A | A | D | B | A | B |
| Hu3G8VL-11 | B | A | A | E | B | A | B |
| Hu3G8VL-12 | B | A | A | F | B | A | B |
| Hu3G8VL-13 | B | A | A | G | B | A | B |
| Hu3G8VL-14 | B | A | A | B | B | B | B |
| Hu3G8VL-15 | B | A | A | B | B | C | B |
| Hu3G8VL-16 | B | A | A | B | B | D | B |
| Hu3G8VL-17 | B | A | A | B | B | E | B |
| Hu3G8VL-18 | B | B | A | D | B | A | B |
| Hu3G8VL-19 | B | B | A | D | B | D | B |
| Hu3G8VL-20 | B | B | A | D | B | E | B |

TABLE 4A*-continued

V_L SEQUENCES

| | FR1 | CDR1 | FR2 | CDR2 | FR3 | CDR3 | FR4 |
|---|---|---|---|---|---|---|---|
| Hu3G8VL-21 | B | C | A | D | B | A | B |
| Hu3G8VL-22 | B | C | A | D | B | D | B |
| Hu3G8VL-23 | B | C | A | D | B | E | B |
| Hu3G8VL-24 | B | D | A | D | B | A | B |
| Hu3G8VL-25 | B | D | A | D | B | D | B |
| Hu3G8VL-26 | B | D | A | D | B | E | B |
| Hu3G8VL-27 | B | E | A | D | B | A | B |
| Hu3G8VL-28 | B | E | A | D | B | D | B |
| Hu3G8VL-29 | B | E | A | D | B | E | B |
| Hu3G8VL-30 | B | A | A | D | B | D | B |
| Hu3G8VL-31 | B | A | A | D | B | E | B |
| Hu3G8VL-32 | B | A | A | H | B | A | B |
| Hu3G8VL-33 | B | A | A | I | B | A | B |
| Hu3G8VL-34 | B | A | A | J | B | A | B |
| Hu3G8VL-35 | B | B | A | H | B | D | B |
| Hu3G8VL-36 | B | C | A | H | B | D | B |
| Hu3G8VL-37 | B | E | A | H | B | D | B |
| Hu3G8VL-38 | B | B | A | I | B | D | B |
| Hu3G8VL-39 | B | C | A | I | B | D | B |
| Hu3G8VL-40 | B | E | A | I | B | D | B |
| Hu3G8VL-41 | B | B | A | J | B | D | B |
| Hu3G8VL-42 | B | C | A | J | B | D | B |
| Hu3G8VL-43 | B | E | A | J | B | D | B |
| Hu3G8VL-44 | B | A | A | K | B | A | B |

*Letters in Table 4A refer to sequences in Tables 4B-H.

TABLE 4B

FR1

| A | B | RESIDUE |
|---|---|---|
| D | D | 1 |
| T | I | 2 |
| V | V | 3 |
| L | M | 4 |
| T | T | 5 |
| Q | Q | 6 |
| S | S | 7 |
| P | P | 8 |
| A | D | 9 |
| S | S | 10 |
| L | L | 11 |
| A | A | 12 |
| V | V | 13 |
| S | S | 14 |
| L | L | 15 |
| G | G | 16 |
| Q | E | 17 |
| R | R | 18 |
| A | A | 19 |
| T | T | 20 |
| I | I | 21 |
| S | N | 22 |
| C | C | 23 |
| 65 | 66 | Seq ID No |

TABLE 4C

CDR1

| A | B | C | D | E | F | G | RESIDUE |
|---|---|---|---|---|---|---|---|
| K | R | K | K | K | K | K | 24 |
| A | A | S | A | A | A | A | 25 |
| S | S | S | S | S | S | S | 26 |
| Q | Q | Q | Q | Q | Q | Q | 27 |
| S | S | S | S | S | S | S | 27A |
| V | V | V | V | V | V | V | 27B |
| D | D | D | D | D | D | D | 27C |

TABLE 4C-continued

CDR1

| A | B | C | D | E | F | G | RESIDUE |
|---|---|---|---|---|---|---|---|
| F | F | F | F | F | F | F | 27D |
| D | D | D | D | D | D | D | 28 |
| G | G | G | G | G | G | G | 29 |
| D | D | D | D | D | D | D | 30 |
| S | S | S | S | S | S | S | 31 |
| F | F | F | Y | F | F | Y | 32 |
| M | M | M | M | L | M | L | 33 |
| N | N | N | N | N | A | A | 34 |
| 67 | 68 | 69 | 70 | 71 | 72 | 73 | Seq ID No |

TABLE 4D

FR2

| A | RESIDUE |
|---|---|
| W | 35 |
| Y | 36 |
| Q | 37 |
| Q | 38 |
| K | 39 |
| P | 40 |
| G | 41 |
| Q | 42 |
| P | 43 |
| P | 44 |
| K | 45 |
| L | 46 |
| L | 47 |
| I | 48 |
| Y | 49 |
| 74 | Seq ID No |

TABLE 4E

CDR2

| A | B | C | D | E | F | G | H | I | J | K | RESIDUE |
|---|---|---|---|---|---|---|---|---|---|---|---|
| T | D | W | T | D | D | S | S | S | T | T | 50 |
| T | A | A | T | A | A | A | T | T | T | T | 51 |
| S | S | S | S | S | S | S | S | S | S | S | 52 |
| N | N | N | N | N | N | N | N | N | N | S | 53 |
| L | L | L | L | L | L | L | L | L | L | L | 54 |
| E | E | E | E | E | A | Q | E | Q | Q | Q | 55 |
| S | S | S | T | T | T | S | S | S | S | S | 56 |
| 75 | 76 | 77 | 78 | 79 | 80 | 81 | 82 | 83 | 84 | 85 | Seq ID No |

TABLE 4F

FR3

| A | B | RESIDUE |
|---|---|---|
| G | G | 57 |
| I | V | 58 |
| P | P | 59 |
| A | D | 60 |
| R | R | 61 |
| F | F | 62 |
| S | S | 63 |
| A | G | 64 |
| S | S | 65 |
| G | G | 66 |
| S | S | 67 |
| G | G | 68 |
| T | T | 69 |
| D | D | 70 |

TABLE 4F-continued

FR3

| A | B | RESIDUE |
|---|---|---------|
| F | F | 71 |
| T | T | 72 |
| L | L | 73 |
| N | T | 74 |
| I | I | 75 |
| H | S | 76 |
| P | S | 77 |
| V | L | 78 |
| E | Q | 79 |
| E | A | 80 |
| E | E | 81 |
| D | D | 82 |
| T | V | 83 |
| A | A | 84 |
| T | V | 85 |
| Y | Y | 86 |
| Y | Y | 87 |
| C | C | 88 |
| 86 | 87 | Seq ID No |

TABLE 4G

CDR3

| A | B | C | D | E | RESIDUE |
|---|---|---|---|---|---------|
| Q | Q | Q | Q | Q | 89 |
| Q | Q | Q | Q | Q | 90 |
| S | S | S | S | S | 91 |

TABLE 4G-continued

CDR3

| A | B | C | D | E | RESIDUE |
|---|---|---|---|---|---------|
| N | Y | Y | N | N | 92 |
| E | S | E | S | E | 93 |
| D | T | D | D | T | 94 |
| P | P | P | P | P | 95 |
| Y | Y | Y | Y | Y | 96 |
| T | T | T | T | T | 97 |
| 88 | 89 | 90 | 91 | 92 | Seq ID No |

TABLE 4H

FR4

| A | B | RESIDUE |
|---|---|---------|
| F | F | 98 |
| G | G | 99 |
| G | Q | 100 |
| G | G | 101 |
| T | T | 102 |
| K | K | 103 |
| L | L | 104 |
| E | E | 105 |
| I | I | 106 |
| K | K | 107 |
| 93 | 94 | Seq ID No |

TABLE 5

Hu3G8VL-1
(SEQ ID NO:95)
```
CGAGCTAGCTGAGATCACAGTTCTCTCTACAGTTACTGAGCACACAGGACCTCACCATGGGATGGAGCTGTATCATCCTC
TTCTTGGTAGCAACAGCTACAGGTAAGGGGCTCACAGTAGCAGGCTTGAGGTCTGGACATATATATGGGTGACAATGACA
TCCACTTTGCCTTTCTCTCCACAGGTGTCCACTCCGACATCGTGATGACCCAATCTCCAGACTCTTTGGCTGTGTCTCTA
GGGGAGAGGGCCACCATCAACTGCAAGGCCAGCCAAAGTGTTGATTTTGATGGTGATAGTTTTATGAACTGGTACCAACA
GAAACCAGGACAGCCACCCAAACTCCTCATCTATACTACATCCAATCTAGAATCTGGGGTCCCAGACAGGTTTAGTGGCA
GTGGGTCTGGGACAGACTTCACCCTCACCATCAGCAGCCTGCAGGCTGAGGATGTGGCAGTTTATTACTGTCAGCAAAGT
AATGAGGATCCGTACACGTTCGGACAGGGGACCAAGCTTGAgATcAAA
```
Hu3G8VL-1
(SEQ ID NO:96)
```
DIVMTQSPDSLAVSLGERATINCKASQSVDFDGDSFMNWYQQKPGQPPKLLIYTTSNLESGVPDRFSGSGSGTDFTLTIS
SLQAEDVAVYYCQQSNEDPYTFGQGTKLEIK
```
Hu3G8VL-1K
(SEQ ID NO:97)
```
CGAGCTAGCTGAGATCACAGTTCTCTCTACAGTTACTGAGCACACAGGACCTCACCATGGGATGGAGCTGTATCATCCTC
TTCTTGGTAGCAACAGCTACAGGTAAGGGGCTCACAGTAGCAGGCTTGAGGTCTGGACATATATATGGGTGACAATGACA
TCCACTTTGCCTTTCTCTCCACAGGTGTCCACTCCGACATCGTGATGACCCAATCTCCAGACTCTTTGGCTGTGTCTCTA
GGGGAGAGGGCCACCATCAACTGCAAGGCCAGCCAAAGTGTTGATTTTGATGGTGATAGTTTTATGAACTGGTACCAACA
GAAACCAGGACAGCCACCCAAACTCCTCATCTATACTACATCCAATCTAGAATCTGGGGTCCCAGACAGGTTTAGTGGCA
GTGGGTCTGGGACAGACTTCACCCTCACCATCAGCAGCCTGCAGGCTGAGGATGTGGCAGTTTATTACTGTCAGCAAAGT
AATGAGGATCCGTACACGTTCGGACAGGGGACCAAGCTTGAgATcAAACgAaCTGTGGCTGCACCATCGGTCTTCATCTT
CCCGCCATCTGATGAGCAGTTGAAATCTGGAACTGCCTCTGTTGTGTGCCTGCTGAATAACTTCTATCCCAGAGAGGCCA
AAGTACAGTGGAAGGTGGATAACGCCCTCCAATCGGGTAACTCCCAGGAGAGTGTCACAGAGCAGGACAGCAAGGACAGC
ACCTACAGCCTCAGCAGCACCCTGACGCTGAGCAAAGCAGACTACGAGAAACACAAAGTCTACGCCTGCGAAGTCACCCA
TCAGGGCCTGAGCTCGCCCGTCACAAAGAGCTTCAACAGGGGAGAGTGTTAGTTCTAGAGTCGACTCTAGAGGATCCCCG
GGTACCGAGCTCGAATTC
```
Hu3G8VL-1K
(SEQ ID NO:98)
```
DIVMTQSPDSLAVSLGERATINCKASQSVDFDGDSFMNWYQQKPGQPPKLLIYTTSNLESGVPDRFSGSGSGTDFTLTIS
SLQAEDVAVYYCQQSNEDPYTFGQGTKLEIKRTVAAPSVFIFPPSDEQLKSGTASVVCLLNNFYPREAKVQWKVDNALQS
GNSQESVTEQDSKDSTYSLSSTLTLSKADYEKHKVYACEVTHQGLSSPVTKSFNRGEC
```
Hu3G8VL-43
(SEQ ID NO:99)
```
CGAGCTAGCTGAGATCACAGTTCTCTCTACAGTTACTGAGCACACAGGACCTCACCATGGGATGGAGCTGTATCATCCTC
TTCTTGGTAGCAACAGCTACAGGTAAGGGGCTCACAGTAGCAGGCTTGAGGTCTGGACATATATATGGGTGACAATGACA
TCCACTTTGCCTTTCTCTCCACAGGTGTCCACTCCGACATCGTGATGACCCAATCTCCAGACTCTTTGGCTGTGTCTCTA
```

TABLE 5-continued

```
GGGGAGAGGGCCACCATCAACTGCAAGtCCAGCCAAAGTGTTGATTTTGATGGTGATAGTTTTATGAACTGGTACCAACA
GAAACCAGGACAGCCACCCAAACTCCTCATCTATACTACATCCAgTCTAGAATCTGGGGTCCCAGACAGGTTTAGTGGCA
GTGGGTCTGGGACAGACTTCACCCTCACCATCAGCAGCCTGCAGGCTGAGGATGTGGCAGTTTATTACTGTCAGCAAAGT
AATtcGGATCCGTACACGTTCGGACAGGGGACCAAGCTTGAgATcAAA
Hu3G8VL-43
```
(SEQ ID NO:100)
```
DIVMTQSPDSLAVSLGERATINCKSSQSVDFDGDSFMNWYQQKPGQPPKLLIYTTSSLESGVPDRFSGSGSGTDFTLTIS
SLQAEDVAVYYCQQSNSDPYTFGQGTKLEIK
Hu3G8VL-43 + Kappa
```
(SEQ ID NO:101)
```
CGAGCTAGCTGAGATCACAGTTCTCTCTACAGTTACTGAGCACACAGGACCTCACCATGGGATGGAGCTGTATCATCCTC
TTCTTGGTAGCAACAGCTACAGGTAAGGGGCTCACAGTAGCAGGCTTGAGGTCTGGACATATATATGGGTGACAATGACA
TCCACTTTGCCTTTCTCTCCACAGGTGTCCACTCCGACATCGTGATGACCCAATCTCCAGACTCTTTGGCTGTGTCTCTA
GGGGAGAGGGCCACCATCAACTGCAAGtCCAGCCAAAGTGTTGATTTTGATGGTGATAGTTTTATGAACTGGTACCAACA
GAAACCAGGACAGCCACCCAAACTCCTCATCTATACTACATCCAgTCTAGAATCTGGGGTCCCAGACAGGTTTAGTGGCA
GTGGGTCTGGGACAGACTTCACCCTCACCATCAGCAGCCTGCAGGCTGAGGATGTGGCAGTTTATTACTGTCAGCAAAGT
AATtcGGATCCGTACACGTTCGGACAGGGGACCAAGCTTGAgATcAAAGaACTGTGGCTGCACCATCGGTCTTCATCTT
CCCGCCATCTGATGAGCAGTTGAAATCTGGAACTGCCTCTGTTGTGTGCCTGCTGAATAACTTCTATCCCAGAGAGGCCA
AAGTACAGTGGAAGGTGGATAACGCCCTCCAATCGGGTAACTCCCAGGAGAGTGTCACAGAGCAGGACAGCAAGGACAGC
ACCTACAGCCTCAGCAGCACCCTGACGCTGAGCAAAGCAGACTACGAGAAACACAAAGTCTACGCCTGCGAAGTCACCCA
TCAGGGCCTGAGCTCGCCCGTCACAAAGAGCTTCAACAGGGGAGAGTGTTAGTTCTAGAGTCGACTCTAGAGGATCCCCG
GGTACCGAGCTCGAATTC
Hu3G8VL-43K
```
(SEQ ID NO:102)
```
DIVMTQSPDSLAVSLGERATINCKSSQSVDFDGDSFMNWYQQKPGQPPKLLIYTTSSLESGVPDRFSGSGSGTDFTLTIS
SLQAEDVAVYYCQQSNSDPYTFGQGTKLEIKRTVAAPSVFIFPPSDEQLKSGTASVVCLLNNFYPREAKVQWKVDNALQS
GNSQESVTEQDSKDSTYSLSSTLTLSKADYEKHKVYACEVTHQGLSSPVTKSPNRGEC
Hu3G8VH-1
```
(SEQ ID NO:103)
```
GCTAGCgtttaaacttaagcttGTTGACTAGTGAGATCACAGTTCTCTCTACAGTTACTGAGCACACAGGACCTCACCAT
GGGATGGAGCTGTATCATCCTCTTCTTGGTAGCAACAGCTACAGGTAAGGGGCTCACAGTAGCAGGCTTGAGGTCTGGAC
ATATATATGGGTGACAATGACATCCACTTTGCCTTTCTCTCCACAGGTGTCCACTCCCAGGTTACCCTGAGAGAGTCTGG
CCCTGCGCTGGTGAAGCCCACACAGACCCTCACACTGACTTGTACCTTCTCTGGGTTTTCACTGAGCACTTCTGGTATGG
GTGTAGGCTGGATTCGTCAGCCTCCCGGGAAGGCTCTAGAGTGGCTGGCACACATTTGGTGGGATGATGACAAGCGCTAT
AATCCAGCCCTGAAGAGCCGACTGACAATCTCCAAGGATACCTCCAAAAACCAGGTAGTCCTCACAATGACCAACATGGA
CCCTGTGGATACTGCCACATACTACTGTGCTCGGATAAACCCCGCCTGGTTTGCTTACTGGGGCCAAGGGACTCTGGTCA
CTGTGAGCTCA
Hu3G8VH-1
```
(SEQ ID NO:104)
```
QVTLRESGPALVKPTQTLTLTCTFSGFSLSTSGMGVGWIRQPPGKALEWLAHIWWDDDKRYNPALKSRLTISKDTSKNQV
VLTMTNMDPVDTATYYCARINPAWFAYWGQGTLVTVSS
Hu3G8VH-1G1
```
(SEQ ID NO:105)
```
GCTAGCgtttaaacttaagcttGTTGACTAGTGAGATCACAGTTCTCTCTACAGTTACTGAGCACACAGGACCTCACCAT
GGGATGGAGCTGTATCATCCTCTTCTTGGTAGCAACAGCTACAGGTAAGGGGCTCACAGTAGCAGGCTTGAGGTCTGGAC
ATATATATGGGTGACAATGACATCCACTTTGCCTTTCTCTCCACAGGTGTCCACTCCCAGGTTACCCTGAGAGAGTCTGG
CCCTGCGCTGGTGAAGCCCACACAGACCCTCACACTGACTTGTACCTTCTCTGGGTTTTCACTGAGCACTTCTGGTATGG
GTGTAGGCTGGATTCGTCAGCCTCCCGGGAAGGCTCTAGAGTGGCTGGCACACATTTGGTGGGATGATGACAAGCGCTAT
AATCCAGCCCTGAAGAGCCGACTGACAATCTCCAAGGATACCTCCAAAAACCAGGTAGTCCTCACAATGACCAACATGGA
CCCTGTGGATACTGCCACATACTACTGTGCTCGGATAAACCCCGCCTGGTTTGCTTACTGGGGCCAAGGGACTCTGGTCA
CTGTGAGCTCAgcctccaccaaggcccatcggtcttccccctggcaccctcctccaagagcacctctgggggcacagcg
gccctgggctgcctggtcaaggactacttccccgaaccggtgacggtgtcgtggaactcaggcgccctgaccagcggcgt
gcacaccttcccggctgtcctacagtcctcaggactctactccctcagcagcgtggtgaccgtgccctccagcagcttgg
gcacccagacctacatctgcaacgtgaatcacaagcccagcaacaccaaggtggacaagaaagttgagcccaaatcttgt
gacaaaactcacacatgcccaccgtgcccagcacctgaactcctggggggaccgtcagtcttcctcttccccccaaaacc
caaggacaccctcatgatctcccggacccctgaggtcacatgcgtggtggtggacgtgagccacgaagaccctgaggtca
agttcaactggtacgtggacggcgtggaggtgcataatgccaagacaaaaccgcgggaggagcagtacaacagcacgtac
cgtgtggtcagcgtcctcaccgtcctgcaccaggactggctgaatggcaaggagtacaagtgcaaggtctccaacaaagc
cctcccagcccccatcgagaaaaccatctccaaagccaaagggcagccccgagaaccacaggtgtacaccctgcccccat
cccgggatgagctgaccaagaaccaggtcagcctgacctgcctggtcaaaggcttctatcccagcgacatcgccgtggag
tgggagagcaatgggcagccggagaacaactacaagaccacgcctcccgtgctggactccgacggctccttcttcctcta
cagcaagctcaccgtggacaagagcaggtggcagcaggggaacgtcttctcatgctccgtgatgcatgaggctctgcaca
accactacacgcagaagagcctctccctgtctccgggtaaatgagtgcggccgcGAATTC
Hu3GSVH-1G1
```
(SEQ ID NO:107)
```
QVTLRESGPALVKPTQTLTLTCTFSGFSLSTSGMGVGWIRQPPGKALEWLAHIWWDDDKRYNPALKSRLTISKDTSKNQV
VLTMTNMDPVDTATYYCARINPAWFAYWGQGTLVTVSSASTKGPSVFPLAPSSKSTSGGTAALGCLVKDYFPEPVTVSWN
SGALTSGVHTFPAVLQSSGLYSLSSVVTVPSSSLGTQTYICNVNHKPSNTKVDKRVEPKSCDKTHTCPPCPAPELLGGPS
VFLFPPKPKDTLMISRTPEVTCVVVDVSHEDPEVKFNWYVDGVEVHNAKTKPREEQYNSTYRVVSVLTVLHQDWLNGKEY
KCKVSNKALPAPIEKTISKAKGQPREPQVYTLPPSRDELTKNQVSLTCLVKGFYPSDIAVEWESNGQPENNYKTTPPVLD
SDGSFFLYSKLTVDKSRWQQGNVFSCSVMHEALHNHYTQKSLSLSPGK
Hu3G8VH-5
```
(SEQ ID NO:108)
```
GCTAGCgtttaaacttaagcttGTTGACTAGTGAGATCACAGTTCTCTCTACAGTTACTGAGCACACAGGACCTCACCAT
GGGATGGAGCTGTATCATCCTCTTCTTGGTAGCAACAGCTACAGGTAAGGGGCTCACAGTAGCAGGCTTGAGGTCTGGAC
ATATATATGGGTGACAATGACATCCACTTTGCCTTTCTCTCCACAGGTGTCCACTCCCAGGTTACCCTGAGAGAGTCTGG
CCCTGCGCTGGTGAAGCCCACACAGACCCTCACACTGACTTGTACCTTCTCTGGGTTTTCACTGAGCACTTCTGGTATGG
GTGTAGGCTGGATTCGTCAGCCTCCCGGGAAGGCTCTAGAGTGGCTGGCACACATTTGGTGGGATGATGACAAGCGCTAT
AATCCAGCCCTGAAGAGCCGACTGACAATCTCCAAGGATACCTCCAAAAACCAGGTAGTCCTCACAATGACCAACATGGA
```

TABLE 5-continued

```
CCCTGTGGATACTGCCACATACTACTGTGCTCaaATAAACCCCGCCTGGTTTGCTTACTGGGGCCAAGGGACTCTGGTCA
CTGTGAGCTCA
```
Hu3G8VH-5

(SEQ ID NO:109)
```
QVTLRESGPALVKPTQTLTLTCTFSGFSLSTSGMGVGWIRQPPGKALEWLAHIWWDDDKRYNPALKSRLTISKDTSKNQV
VLTMTNMDPVDTATYYCAQINPAWFAYWGQGTLVTVSS
```
Hu3G8VH-5G1Ag (SEQ ID NO:110)
```
GCTAGCgtttaaacttaagcttGTTGACTAGTGAGATCACAGTTCTCTCTACAGTTACTGAGCACACAGGACCTCACCAT
GGGATGGAGCTGTATCATCCTCTTCTTGGTAGCAACAGCTACAGGTAAGGGGCTCACAGTAGCAGGCTTGAGGTCTGGAC
ATATATATGGGTGACAATGACATCCACTTTGCCTTTCTCTCCACAGGTGTCCACTCCCAGGTTACCCTGAGAGAGTCTGG
CCCTGCGCTGGTGAAGCCCACACAGACCCTCACACTGACTTGTACCTTCTCTGGGTTTTCACTGAGCACTTCTGGTATGG
GTGTAGGCTGGATTCGTCAGCCTCCCGGGAAGGCTCTAGAGTGGCTGGCACACATTTGGTGGGATGATGACAAGCGCTAT
AATCCAGCCCTGAAGAGCCGACTGACAATCTCCAAGGATACCTCCAAAAACCAGGTAGTCCTCACAATGACCAACATGGA
CCCTGTGGATACTGCCACATACTACTGTGCTCaaATAAACCCCGCCTGGTTTGCTTACTGGGGCCAAGGGACTCTGGTCA
CTGTGAGCTCAgcctccaccaagggcccatcggtcttccccctggcaccctcctccaagagcacctctgggggcacagcg
gccctgggctgcctggtcaaggactacttccccgaaccggtgacggtgtcgtggaactcaggcgccctgaccagcggcgt
gcacaccttcccggctgtcctacagtcctcaggactctactccctcagcagcggtggaccgtgccctccagcagcttgg
gcacccagacctacatctgcaacgtgaatcacaagcccagcaacaccaaggtggacaagagagttgagcccaaatcttgt
gacaaaactcacacatgcccaccgtgcccagcacctgaactcctgggggaccgtcagtcttcctcttccccccaaaacc
caaggacaccctcatgatctcccggacccctgaggtcacatgcgtggtggtggacgtgagccacgaagaccctgaggtca
agttcaactggtacgtggacggcgtggaggtgcataatgccaagacaaagccgcgggaggagcagtaCaGagcacgtac
cgtgtggtcagcgtcctcaccgtcctgcaccaggactggctgaatggcaaggagtacaagtgcaaggtctccaacaaagc
cctcccagcccccatcgagaaaaccatctccaaagccaaagggcagccccgagaaccacaggtgtacaccctgcccccat
cccgggatgagctgaccaagaaccaggtcagcctgacctgcctggtcaaaggcttctatcccagcgacatcgccgtggag
tgggagagcaatgggcagccggagaacaactacaagaccacgcctcccgtgctggactccgacggctccttcttcctcta
cagcaagctcaccgtggacaagagcaggtggcagcaggggaacgtcttctcatgctccgtgatgcatgaggctctgcaca
accactacacgcagaagagcctctccctgtctccgggtaaatgagtgcggccgcGAATTC
```
Hu3G8VH-5G1Ag (SEQ ID NO:111)
```
QVTLRESGPALVKPTQTLTLTCTFSGFSLSTSGMGVGWIRQPPGKALEWLAHIWWDDDKRYNPALKSRLTISKDTSKNQV
VLTMTNMDPVDTATYYCAQINPAWFAYWGQGTLVTVSSASTKGPSVFPLAPSSKSTSGGTAALGCLVKDYFPEPVTVSWN
SGALTSGVHTFPAVLQSSGLYSLSSVVTVPSSSLGTQTYICNVNHKPSNTKVDKRVEPKSCDKTHTCPPCPAPELLGGPS
VFLFPPKPKDTLMISRTPEVTCVVVDVSHEDPEVKFNWYVDGVEVHNAKTKPREEQYQSTYRVVSVLTVLHQDWLNGKEY
KCKVSNKALPAPIEKTISKAKGQPREPQVYTLPPSRDELTKNQVSLTCLVKGFYPSDIAVEWESNGQPENNYKTTPPVLD
SDGSFFLYSKLTVDKSRWQQGNVFSCSVMHEALHNHYTQKSLSLSPGK
```
Hu3G8VH-22

(SEQ ID NO:112)
```
GCTAGCgtttaaacttaagcttGTTGACTAGTGAGATCACAGTTCTCTCTACAGTTACTGAGCACACAGGACCTCACCAT
GGGATGGAGCTGTATCATCCTCTTCTTGGTAGCAACAGCTACAGGTAAGGGGCTCACAGTAGCAGGCTTGAGGTCTGGAC
ATATATATGGGTGACAATGACATCCACTTTGCCTTTCTCTCCACAGGTGTCCACTCCCAGGTTACCCTGAGAGAGTCTGG
CCCTGCGCTGGTGAAGCCCACACAGACCCTCACACTGACTTGTACCTTCTCTGGGTTTTCACTGAGCACTTCTGGTgTGG
GTGTAGGCTGGATTCGTCAGCCTCCCGGGAAGGCTCTAGAGTGGCTGGCACACATTTGGTGGGATGATGACAAGCGCTAT
tcTCCAtCCCTGAAGAGCCGACTGACAATCTCCAAGGATACCTCCAAAAACCAGGTAGTCCTCACAATGACCAACATGGA
CCCTGTGGATACTGCCACATACTACTGTGCTCGGATAAACCCCGCCTacTTTGCTTACTGGGGCCAAGGGACTCTGGTCA
CTGTGAGCTCA
```
Hu3G8VH-22

(SEQ ID NO:113)
```
QVTLRESGPALVKPTQTLTLTCTFSGFSLSTSGVGVGWIRQPPGKALEWLAHIWWDDDKRYSPSLKSRLTISKDTSKNQV
VLTMTNMDPVDTATYYCARINPAYFAYWGQGTLVTVS
```
Hu3G8VH-22G1Ag (SEQ ID NO:114)
```
GCTAGCgtttaaacttaagcttGTTGACTAGTGAGATCACAGTTCTCTCTACAGTTACTGAGCACACAGGACCTCACCAT
GGGATGGAGCTGTATCATCCTCTTCTTGGTAGCAACAGCTACAGGTAAGGGGCTCACAGTAGCAGGCTTGAGGTCTGGAC
ATATATATGGGTGACAATGACATCCACTTTGCCTTTCTCTCCACAGGTGTCCACTCCCAGGTTACCCTGAGAGAGTCTGG
CCCTGCGCTGGTGAAGCCCACACAGACCCTCACACTGACTTGTACCTTCTCTGGGTTTTCACTGAGCACTTCTGGTgTGG
GTGTAGGCTGGATTCGTCAGCCTCCCGGGAAGGCTCTAGAGTGGCTGGCACACATTTGGTGGGATGATGACAAGCGCTAT
tcTCCAtCCCTGAAGAGCCGACTGACAATCTCCAAGGATACCTCCAAAAACCAGGTAGTCCTCACAATGACCAACATGGA
CCCTGTGGATACTGCCACATACTACTGTGCTCGGATAAACCCCGCCTacTTTGCTTACTGGGGCCAAGGGACTCTGGTCA
CTGTGAGCTCAgcctccaccaagggcccatcggtcttccccctggcaccctcctccaagagcacctctgggggcacagcg
gccctgggctgcctggtcaaggactacttccccgaaccggtgacggtgtcgtggaactcaggcgccctgaccagcggcgt
gcacaccttcccggctgtcctacagtcctcaggactctactccctcagcagcggtggaccgtgccctccagcagcttgg
gcacccagacctacatctgcaacgtgaatcacaagcccagcaacaccaaggtggacaagagagttgagcccaaatcttgt
gacaaaactcacacatgcccaccgtgcccagcacctgaactcctgggggaccgtcagtcttcctcttccccccaaaacc
caaggacaccctcatgatctcccggacccctgaggtcacatgcgtggtggtggacgtgagccacgaagaccctgaggtca
agttcaactggtacgtggacggcgtggaggtgcataatgccaagacaaagccgcgggaggagcagtaCaGagcacgtac
cgtgtggtcagcgtcctcaccgtcctgcaccaggactggctgaatggcaaggagtacaagtgcaaggtctccaacaaagc
cctcccagcccccatcgagaaaaccatctccaaagccaaagggcagccccgagaaccacaggtgtacaccctgcccccat
cccgggatgagctgaccaagaaccaggtcagcctgacctgcctggtcaaaggcttctatcccagcgacatcgccgtggag
tgggagagcaatgggcagccggagaacaactacaagaccacgcctcccgtgctggactccgacggctccttcttcctcta
cagcaagctcaccgtggacaagagcaggtggcagcaggggaacgtcttctcatgctccgtgatgcatgaggctctgcaca
accactacacgcagaagagcctctccctgtctccgggtaaatgagtgcggccgcGAATTC
```
Hu3G8VH-22G1Ag (SEQ ID NO:115)
```
QVTLRESGPALVKPTQTLTLTCTFSGFSLSTSGVGVGWIRQPPGKALEWLAHIWWDDDKRYSPSLKSRLTISKDTSKNQV
VLTMTNMDPVDTATYYCARINPAYFAYWGQGTLVTVSSASTKGPSVFPLAPSSKSTSGGTAALGCLVKDYFPEPVTVSWN
SGALTSGVHTFPAVLQSSGLYSLSSVVTVPSSSLGTQTYICNVNHKPSNTKVDKRVEPKSCDKTHTCPPCPAPELLGGPS
VFLFPPKPKDTLMISRTPEVTCVVVDVSHEDPEVKFNWYVDGVEVHNAKTKPREEQYQSTYRVVSVLTVLHQDWLNGKEY
KCKVSNKALPAPIEKTISKAKGQPREPQVYTLPPSRDELTKNQVSLTCLVKGFYPSDIAVEWESNGQPENNYKTTPPVLD
```

TABLE 5-continued

```
SDGSFFLYSKLTVDKSRWQQGNVFSCSVMHEALHNHYTQKSLSLSPGK
Hu3G8VL-22
                                                                (SEQ ID NO:118)
DIVMTQSPDSLAVSLGERATINCKSSQSVDFDGDSFMNWYQQKPGQPPKLLIYTTSNLETGVPDRFSGSGSGTDFTLTIS
SLQAEDVAVYYCQQSNSDPYTFGQGTKLEIK
Hu3G8VL-22K
                                                                (SEQ ID NO:119)
DIVMTQSPDSLAVSLGERATINCKSSQSVDFDGDSFMNWYQQKPGQPPKLLIYTTSNLETGVPDRFSGSGSGTDFTLTIS
SLQAEDVAVYYCQQSNSDPYTFGQGTKLEIKRTVAAPSVFIFPPSDEQLKSGTASVVCLLNNFYPREAKVQWKVDNALQS
GNSQESVTEQDSKDSTYSLSSTLTLSKADYEKHKVYACEVTHQGLSSPVTKSFNRGEC
Hu3G8VL-22
                                                                (SEQ ID NO:106)
CGAGCTAGCTGAGATCACAGTTCTCTCTACAGTTACTGAGCACACAGGACCTCACCATGGGATGGAGCTGTATCATCCTC
TTCTTGGTAGCAACAGCTACAGGTAAGGGGCTCACAGTAGCAGGCTTGAGGTCTGGACATATATATGGGTGACAATGACA
TCCACTTTGCCTTTCTCTCCACAGGTGTCCACTCCGACATCGTGATGACCCAATCTCCAGACTCTTTGGCTGTGTCTCTA
GGGGAGAGGGCCACCATCAACTGCAAGTCCAGCCAAAGTGTTGATTTTGATGGTGATAGTTTTATGAACTGGTACCAACA
GAAACCAGGACAGCCACCCAAACTCCTCATCTATACTACATCCAATCTAGAAACTGGGGTCCCAGACAGGTTTAGTGGCA
GTGGGTCTGGGACAGACTTCACCCTCACCATCAGCAGCCTGCAGGCTGAGGATGTGGCAGTTTATTACTGTCAGCAAAGT
AATTCGGATCCGTACACGTTCGGACAGGGGACCAAGCTTGAgATcAAA
Hu3G8VL-22K
                                                                (SEQ ID NO:24)
CGAGCTAGCTGAGATCACAGTTCTCTCTACAGTTACTGAGCACACAGGACCTCACCATGGGATGGAGCTGTATCATCCTC
TTCTTGGTAGCAACAGCTACAGGTAAGGGGCTCACAGTAGCAGGCTTGAGGTCTGGACATATATATGGGTGACAATGACA
TCCACTTTGCCTTTCTCTCCACAGGTGTCCACTCCGACATCGTGATGACCCAATCTCCAGACTCTTTGGCTGTGTCTCTA
GGGGAGAGGGCCACCATCAACTGCAAGTCCAGCCAAAGTGTTGATTTTGATGGTGATAGTTTTATGAACTGGTACCAACA
GAAACCAGGACAGCCACCCAAACTCCTCATCTATACTACATCCAATCTAGAAACTGGGGTCCCAGACAGGTTTAGTGGCA
GTGGGTCTGGGACAGACTTCACCCTCACCATCAGCAGCCTGCAGGCTGAGGATGTGGCAGTTTATTACTGTCAGCAAAGT
AATTCGGATCCGTACACGTTCGGACAGGGGACCAAGCTTGAgATcAAACGaACTGTGGCTGCACCATCGGTCTTCATCTT
CCCGCCATCTGATGAGCAGTTGAAATCTGGAACTGCCTCTGTTGTGTGCCTGCTGAATAACTTCTATCCCAGAGAGGCCA
AAGTACAGTGGAAGGTGGATAACGCCCTCCAATCGGGTAACTCCCAGGAGAGTGTCACAGAGCAGGACAGCAAGGACAGC
ACCTACAGCCTCAGCAGCACCCTGACGCTGAGCAAAGCAGACTACGAGAAACACAAAGTCTACGCCTGCGAAGTCACCCA
TCAGGGCCTGAGCTCGCCCGTCACAAAGAGCTTCAACAGGGGAGAGTGTTAGTTCTAGAGTCGACTCTAGAGGATCCCCG
GGTACCGAGCTCGAATTC
```

It is understood that the examples and embodiments described herein are for illustrative purposes only and that various modifications or changes in light thereof will be suggested to persons skilled in the art and are to be included within the spirit and purview of this application and scope of the appended claims. All publications (including sequence accession numbers and corresponding annotations), patents and patent applications cited herein are hereby incorporated by reference in their entirety for all purposes to the same extent as if each individual publication, patent or patent application were specifically and individually indicated to be so incorporated by reference.

What is claimed is:

1. An isolated anti-CD16A antibody comprising a $V_H$ domain comprising a CDR1 having the amino acid sequence of SEQ ID NO:35, a CDR2 having the amino acid sequence of SEQ ID NO:39, and a CDR3 having the amino acid sequence of SEQ ID NO:59 and a $V_L$ domain comprising a CDR1 having the amino acid sequence of SEQ ID NO:67, a CDR2 having the amino acid sequence of SEQ ID NO:75, and a CDR3 having the amino acid sequence of SEQ ID NO:88, wherein said CDRs have an amino acid substitution selected from the group consisting of, in the $V_H$ domain, M34V in CDR1; H50L in CDR2, W52F in CDR2, D54N in CDR2, N60S in CDR2, A62S in CDR2; W99Y in CDR3, A101D in CDR3, and in the $V_L$ domain, K24R in CDR1, A25S in CDR1, F32Y in CDR1, M33L in CDR1, N34A in CDR1, T50D, T50W or T50S in CDR2, T51A in CDR2, N53S in CDR2, E55A or E55Q in CDR2, S56T in CDR2; N92Y in CDR3, N93S in CDR3, and D94T in CDR3, which positions are according to the Kabat numbering scheme.

2. The isolated antibody of claim 1 that lacks an Fc region or comprises an Fc region that lacks effector function.

3. The isolated antibody of claim 2 comprising an Fc region that lacks effector function, which Fc region is a human IgG$_1$ Fc region.

4. The isolated antibody of claim 3 wherein the amino acid corresponding to residue 297 of the Fc region according to the Kabat numbering scheme is not asparagine.

5. The isolated antibody of claim 2 that is a single chain antibody.

6. The isolated antibody of claim 1, wherein said antibody comprises two light chains and two heavy chains.

7. An isolated humanized anti-CD16A antibody comprising a heavy chain variable region having the sequence of SEQ ID NO:113 and a light chain variable region having the sequence of SEQ ID NO:96.

8. An isolated humanized anti-CD16A antibody comprising a $V_H$ CDR1 having the sequence of SEQ ID NO:35, a $V_H$ CDR2 having the sequence of SEQ ID NO:39, a $V_H$ CDR3 having the sequence of SEQ ID NO:59, and a $V_L$ domain having the amino acid sequence of SEQ ID NO:96.

9. An isolated humanized anti-CD16A antibody that comprises a $V_L$ domain having the amino acid sequence SEQ ID NO:96.

10. The isolated antibody of claim 9 that comprises a $V_H$ domain having the amino acid sequence of SEQ ID NO: 109 or SEQ ID NO: 104.

11. The isolated antibody of any of claims 7 and 8-10, wherein said antibody lacks an Fc region or comprises an Fc region that lacks effector function.

12. The isolated antibody of claim 11 comprising an Fc region that lacks effector function, which Fc region is a human $IgG_1$ Fc region.

13. The isolated antibody of claim 11 comprising an Fc region that lacks effector function, wherein amino acid sequence corresponding to residue 297 of the Fc region according to the Kabat numbering scheme is not glycosylated.

14. The isolated antibody of claim 13, wherein the amino acid corresponding to residue 297 of the Fc region according to the Kabat numbering scheme is not asparagine.

15. The isolated antibody of claim 3, wherein the amino acid corresponding to residue 297 of the Fc region according to the Kabat numbering scheme is not glycosylated.

16. An isolated anti-CD16A antibody comprising a $V_H$ CDR1 having the sequence of SEQ ID NO:35, a $V_H$ CDR2 having the sequence of SEQ ID NO:39, a $V_H$ CDR3 having the sequence of SEQ ID NO:59, and a light chain having the amino acid sequence of SEQ ID NO:98.

17. The isolated antibody claim 9, wherein said antibody comprises a heavy chain having the amino acid sequence of SEQ ID NO:111.

18. An isolated humanized anti-CD16A antibody comprising a light chain having the amino acid sequence of SEQ ID NO:98 and a heavy chain having the amino acid sequence of SEQ ID NO:111.

* * * * *

SEQUENCE LISTING s

```
<160> NUMBER OF SEQ ID NOS: 119

<210> SEQ ID NO 1
<211> LENGTH: 354
<212> TYPE: DNA
<213> ORGANISM: mouse

<400> SEQUENCE: 1
caggttactc tgaaagagtc tggccctggg atattgcagc cctcccagac cctcagtctg      60
acttgttctt tctctgggtt ttcactgagg acttctggta tgggtgtagg ctggattcgt     120
cagccttcag ggaagggtct agagtggctg gcacacattt ggtgggatga tgacaagcgc     180
tataatccag ccctgaagag ccgactgaca atctccaagg ataccctccag caaccaggta    240 ttcctcaaaa tcgccagtgt ggacactgca gatactgcca catactactg tgctcaaata    300
aaccccgcct ggtttgctta ctggggccaa gggactctgg tcactgtctc tgca           354

<210> SEQ ID NO 2
<211> LENGTH: 354
<212> TYPE: PRT
<213> ORGANISM: mouse
```

```
<400> SEQUENCE: 2

Cys Ala Gly Gly Thr Thr Ala Cys Thr Cys Thr Gly Ala Ala Gly
  1               5                  10                  15

Ala Gly Thr Cys Thr Gly Gly Cys Cys Cys Thr Gly Gly Ala Thr
                 20                  25                  30

Ala Thr Thr Gly Cys Ala Gly Cys Cys Thr Cys Cys Cys Ala Gly
             35                  40                  45

Ala Cys Cys Cys Thr Cys Ala Gly Cys Thr Gly Ala Cys Thr Thr
 50                  55                  60

Gly Thr Thr Cys Thr Thr Thr Cys Thr Cys Thr Gly Gly Thr Thr
 65              70                  75                  80

Thr Thr Cys Ala Cys Thr Gly Ala Gly Gly Ala Cys Thr Thr Cys Thr
                 85                  90                  95

Gly Gly Thr Ala Thr Gly Gly Thr Gly Thr Ala Gly Gly Cys Thr
                100                 105                 110

Gly Gly Ala Thr Thr Cys Gly Thr Cys Ala Gly Cys Cys Thr Cys
                115                 120                 125

Ala Gly Gly Gly Ala Ala Gly Gly Thr Cys Thr Ala Gly Ala Gly
                130                 135                 140

Thr Gly Gly Cys Thr Gly Gly Cys Ala Cys Ala Cys Ala Thr Thr
145                 150                 155                 160

Gly Gly Thr Gly Gly Gly Ala Thr Gly Ala Thr Gly Ala Cys Ala Ala
                165                 170                 175

Gly Cys Gly Cys Thr Ala Thr Ala Ala Thr Cys Cys Ala Gly Cys Cys
                180                 185                 190

Cys Thr Gly Ala Ala Gly Ala Gly Cys Cys Gly Ala Cys Thr Gly Ala
                195                 200                 205

Cys Ala Ala Thr Cys Thr Cys Cys Ala Ala Gly Gly Ala Thr Ala Cys
                210                 215                 220

Cys Thr Cys Cys Ala Gly Cys Ala Ala Cys Cys Ala Gly Gly Thr Ala
225                 230                 235                 240

Thr Thr Cys Cys Thr Cys Ala Ala Ala Ala Thr Cys Gly Cys Cys Ala
                245                 250                 255

Gly Thr Gly Thr Gly Gly Ala Cys Ala Cys Thr Gly Cys Ala Gly Ala
                260                 265                 270

Thr Ala Cys Thr Gly Cys Cys Ala Cys Ala Thr Ala Cys Thr Ala Cys
             275                 280                 285

Thr Gly Thr Gly Cys Thr Cys Ala Ala Ala Thr Ala Ala Ala Cys Cys
             290                 295                 300

Cys Cys Gly Cys Cys Thr Gly Gly Thr Thr Thr Gly Cys Thr Ala
305                 310                 315                 320

Cys Thr Gly Gly Gly Gly Cys Cys Ala Ala Gly Gly Ala Cys Thr
                325                 330                 335

Cys Thr Gly Gly Thr Cys Ala Cys Thr Gly Thr Cys Thr Cys Thr Gly
                340                 345                 350

Cys Ala

<210> SEQ ID NO 3
<211> LENGTH: 333
<212> TYPE: DNA
<213> ORGANISM: mouse

<400> SEQUENCE: 3
gacactgtgc tgacccaatc tccagcttct ttggctgtgt ctctagggca gagggccacc      60
```

```
atctcctgca aggccagcca aagtgttgat tttgatggtg atagttttat gaactggtac      120
caacagaaac caggacagcc acccaaactc ctcatctata ctacatccaa tctagaatct      180
gggatcccag ccaggtttag tgccagtggg tctgggacag acttcaccct caacatccat      240
cctgtggagg aggaggatac tgcaacctat tactgtcagc aaagtaatga ggatccgtac      300
acgttcggag ggggaccaa gctggaaata aaa                                    333
```

```
<210> SEQ ID NO 4
<211> LENGTH: 333
<212> TYPE: PRT
<213> ORGANISM: mouse

<400> SEQUENCE: 4

Gly Ala Cys Ala Cys Thr Gly Thr Gly Cys Ala Cys Cys Cys
  1               5                  10                  15

Ala Ala Thr Cys Thr Cys Cys Ala Gly Cys Thr Thr Cys Thr Thr Thr
              20                  25                  30

Gly Gly Cys Thr Gly Thr Gly Thr Cys Thr Thr Ala Gly Gly Gly
              35                  40                  45

Cys Ala Gly Ala Gly Gly Cys Cys Ala Cys Cys Ala Thr Cys Thr
 50                  55                  60

Cys Cys Thr Gly Cys Ala Ala Gly Gly Cys Cys Ala Gly Cys Cys Ala
 65                  70                  75                  80

Ala Ala Gly Thr Gly Thr Thr Gly Ala Thr Thr Thr Gly Ala Thr
              85                  90                  95

Gly Gly Thr Gly Ala Thr Ala Gly Thr Thr Thr Ala Thr Gly Ala
             100                 105                 110

Ala Cys Thr Gly Gly Thr Ala Cys Cys Ala Ala Cys Ala Gly Ala Ala
             115                 120                 125

Ala Cys Cys Ala Gly Gly Ala Cys Ala Gly Cys Cys Ala Cys Cys Cys
130                 135                 140

Ala Ala Ala Cys Thr Cys Cys Thr Cys Ala Thr Cys Thr Ala Thr Ala
145                 150                 155                 160

Cys Thr Ala Cys Ala Thr Cys Cys Ala Ala Thr Cys Thr Ala Gly Ala
             165                 170                 175

Ala Thr Cys Thr Gly Gly Ala Thr Cys Cys Ala Gly Cys Cys
             180                 185                 190

Ala Gly Gly Thr Thr Thr Ala Gly Thr Gly Cys Cys Ala Gly Thr Gly
             195                 200                 205

Gly Gly Thr Cys Thr Gly Gly Gly Ala Cys Ala Gly Ala Cys Thr Thr
             210                 215                 220

Cys Ala Cys Cys Cys Thr Cys Ala Ala Cys Ala Thr Cys Cys Ala Thr
225                 230                 235                 240

Cys Cys Thr Gly Thr Gly Gly Ala Gly Gly Ala Gly Gly Ala Gly Gly
                 245                 250                 255

Ala Thr Ala Cys Thr Gly Cys Ala Ala Cys Cys Thr Ala Thr Thr Ala
             260                 265                 270

Cys Thr Gly Thr Cys Ala Gly Cys Ala Ala Ala Gly Thr Ala Ala Thr
             275                 280                 285

Gly Ala Gly Gly Ala Thr Cys Cys Gly Thr Ala Cys Ala Cys Gly Thr
             290                 295                 300

Thr Cys Gly Gly Ala Gly Gly Gly Gly Gly Ala Cys Cys Ala Ala
305                 310                 315                 320
```

Gly Cys Thr Gly Gly Ala Ala Ala Thr Ala Ala Ala Ala
           325                 330

<210> SEQ ID NO 5
<211> LENGTH: 1580
<212> TYPE: DNA
<213> ORGANISM: Artificial Sequence
<220> FEATURE:
<223> OTHER INFORMATION: Synthetic construct

<400> SEQUENCE: 5

| | | | | | |
|---|---|---|---|---|---|
| gctagcgttt | aaacttaagc | ttgttgacta | gtgagatcac | agttctctct | acagttactg | 60 |
| agcacacagg | acctcaccat | gggatggagc | tgtatcatcc | tcttcttggt | agcaacagct | 120 |
| acaggtaagg | ggctcacagt | agcaggcttg | aggtctggac | atatatatgg | gtgacaatga | 180 |
| catccacttt | gcctttctct | ccacaggtgt | ccactcccag | gttaccctga | aagagtctgg | 240 |
| ccctgggata | ttgcagccct | cccagaccct | cagtctgact | tgttctttct | ctgggttttc | 300 |
| actgaggact | tctggtatgg | gtgtaggctg | gattcgtcag | ccttcaggga | agggtctaga | 360 |
| gtggctggca | cacatttggt | gggatgatga | caagcgctat | aatccagccc | tgaagagccg | 420 |
| actgacaatc | tccaaggata | cctccagcaa | ccaggtattc | ctcaaaatcg | ccagtgtgga | 480 |
| cactgcagat | actgccacat | actactgtgc | tcaaataaac | cccgcctggt | ttgcttactg | 540 |
| gggccaaggg | actctggtca | ctgtgagctc | agcctccacc | aagggcccat | cggtcttccc | 600 |
| cctggcaccc | tcctccaaga | gcacctctgg | gggcacagcg | gccctgggct | gcctggtcaa | 660 |
| ggactacttc | cccgaaccgg | tgacggtgtc | gtggaactca | ggcgccctga | ccagcggcgt | 720 |
| gcacaccttc | ccggctgtcc | tacagtcctc | aggactctac | tccctcagca | gcgtggtgac | 780 |
| cgtgccctcc | agcagcttgg | gcacccagac | ctacatctgc | aacgtgaatc | acaagcccag | 840 |
| caacaccaag | gtggacaaga | gagttgagcc | caaatcttgt | gacaaaactc | acacatgccc | 900 |
| accgtgccca | gcacctgaac | tcctgggggg | accgtcagtc | ttcctcttcc | ccccaaaacc | 960 |
| caaggacacc | ctcatgatct | cccggacccc | tgaggtcaca | tgcgtggtgg | tggacgtgag | 1020 |
| ccacgaagac | cctgaggtca | agttcaactg | gtacgtggac | ggcgtggagg | tgcataatgc | 1080 |
| caagacaaag | ccgcgggagg | agcagtacaa | cagcacgtac | cgtgtggtca | gcgtcctcac | 1140 |
| cgtcctgcac | caggactggc | tgaatggcaa | ggagtacaag | tgcaaggtct | ccaacaaagc | 1200 |
| cctcccagcc | cccatcgaga | aaaccatctc | caaagccaaa | gggcagcccc | gagaaccaca | 1260 |
| ggtgtacacc | ctgcccccat | cccgggatga | gctgaccaag | aaccaggtca | gcctgacctg | 1320 |
| cctggtcaaa | ggcttctatc | ccagcgacat | cgccgtggag | tgggagagca | atgggcagcc | 1380 |
| ggagaacaac | tacaagacca | cgcctcccgt | gctggactcc | gacggctcct | tcttcctcta | 1440 |
| cagcaagctc | accgtggaca | agagcaggtg | gcagcagggg | aacgtcttct | catgctccgt | 1500 |
| gatgcatgag | gctctgcaca | accactacac | gcagaagagc | ctctccctgt | ctccgggtaa | 1560 |
| atgagtgcgg | ccgcgaattc | | | | | 1580 |

<210> SEQ ID NO 6
<211> LENGTH: 895
<212> TYPE: DNA
<213> ORGANISM: Artificial Sequence
<220> FEATURE:
<223> OTHER INFORMATION: Synthetic construct

<400> SEQUENCE: 6
gctagctgag atcacagttc tctctacagt tactgagcac acaggacctc accatgggat    60

```
ggagctgtat catcctcttc ttggtagcaa cagctacagg taagggctc acagtagcag      120 gcttgaggtc tggacatata tatgggtgac aatgacatcc actttgcctt tctctccaca      180
ggtgtccact ccgacactgt gctgacccaa tctccagctt ctttggctgt gtctctaggg      240
cagagggcca ccatctcctg caaggccagc caaagtgttg attttgatgg tgatagtttt      300
atgaactggt accaacagaa accaggacag ccacccaaac tcctcatcta tactacatcc      360
aatctagaat ctgggatccc agccaggttt agtgccagtg gtctgggac agacttcacc       420 ctcaacatcc atcctgtgga ggaggaggat actgcaacct attactgtca gcaaagtaat      480
gaggatccgt acacgttcgg agggggacc aagcttgaga tcaaacgaac tgtggctgca      540
ccatcggtct tcatcttccc gccatctgat gagcagttga aatctggaac tgcctctgtt      600
gtgtgcctgc tgaataactt ctatcccaga gaggccaaag tacagtggaa ggtggataac      660
gccctccaat cgggtaactc ccaggagagt gtcacagagc aggacagcaa ggacagcacc      720
tacagcctca gcagcaccct gacgctgagc aaagcagact acgagaaaca caaagtctac      780
gcctgcgaag tcacccatca gggcctgagc tcgcccgtca caaagagctt caacagggga      840
gagtgttagt tctagagtcg actctagagg atccccgggt accgagctcg aattc           895

<210> SEQ ID NO 7
<211> LENGTH: 62
<212> TYPE: DNA
<213> ORGANISM: Artificial Sequence
<220> FEATURE:
<223> OTHER INFORMATION: Primer

<400> SEQUENCE: 7
ccgcgaattc tggccaggtt accctgagag agtctggccc tgcgctggtg aagcccacac      60
ag                                                                    62

<210> SEQ ID NO 8
<211> LENGTH: 80
<212> TYPE: DNA
<213> ORGANISM: Artificial Sequence
<220> FEATURE:
<223> OTHER INFORMATION: Primer

<400> SEQUENCE: 8
gcgctggtga agcccacaca gaccctcaca ctgacttgta ccttctctgg gttttcactg      60
agcacttctg gtatgggtgt                                                 80

<210> SEQ ID NO 9
<211> LENGTH: 42
<212> TYPE: DNA
<213> ORGANISM: Artificial Sequence
<220> FEATURE:
<223> OTHER INFORMATION: Primer

<400> SEQUENCE: 9
tggattcgtc agcctcccgg gaaggctcta gagtggctgg ca                        42

<210> SEQ ID NO 10
<211> LENGTH: 42
<212> TYPE: DNA
<213> ORGANISM: Artificial Sequence
<220> FEATURE:
<223> OTHER INFORMATION: Primer

<400> SEQUENCE: 10
tgccagccac tctagagcct tcccgggagg ctgacgaatc ca                        42
```

<210> SEQ ID NO 11
<211> LENGTH: 72
<212> TYPE: DNA
<213> ORGANISM: Artificial Sequence
<220> FEATURE:
<223> OTHER INFORMATION: Primer

<400> SEQUENCE: 11
gtcctcacaa tgaccaacat ggaccctgtg atactgcca catactactg tgctcggata      60
aaccccgcct gg                                                         72

<210> SEQ ID NO 12
<211> LENGTH: 51
<212> TYPE: DNA
<213> ORGANISM: Artificial Sequence
<220> FEATURE:
<223> OTHER INFORMATION: Primer

<400> SEQUENCE: 12
catgttggtc attgtgagga ctacctggtt tttggaggta tccttggaga t              51

<210> SEQ ID NO 13
<211> LENGTH: 37
<212> TYPE: DNA
<213> ORGANISM: Artificial Sequence
<220> FEATURE:
<223> OTHER INFORMATION: Primer

<400> SEQUENCE: 13
ggctgagctc acagtgacca gagtcccttg gccccag                              37

<210> SEQ ID NO 14
<211> LENGTH: 27
<212> TYPE: DNA
<213> ORGANISM: Artificial Sequence
<220> FEATURE:
<223> OTHER INFORMATION: Primer

<400> SEQUENCE: 14
gtgtaggctg gattcgtcag cctcccg                                         27

<210> SEQ ID NO 15
<211> LENGTH: 33
<212> TYPE: DNA
<213> ORGANISM: Artificial Sequence
<220> FEATURE:
<223> OTHER INFORMATION: Primer

<400> SEQUENCE: 15
gacgaatcca gcctacaccc ataccagaag tgc                                  33

<210> SEQ ID NO 16
<211> LENGTH: 354
<212> TYPE: DNA
<213> ORGANISM: Artificial Sequence
<220> FEATURE:
<223> OTHER INFORMATION: Synthetic construct

<400> SEQUENCE: 16
caggttaccc tgagagagtc tggccctgcg ctggtgaagc ccacacagac cctcacactg      60
acttgtacct tctctgggtt ttcactgagc acttctggta tgggtgtagg ctggattcgt     120
cagcctcccg ggaaggctct agagtggctg gcacacattt ggtgggatga tgacaagcgc     180

| | | |
|---|---|---|
| tataatccag ccctgaagag ccgactgaca atctccaagg ataccctccaa aaaccaggta | 240 | |
| gtcctcacaa tgaccaacat ggaccctgtg gatactgcca catactactg tgctcggata | 300 | |
| aaccccgcct ggtttgctta ctggggccaa gggactctgg tcactgtgag ctca | 354 | |

<210> SEQ ID NO 17
<211> LENGTH: 1580
<212> TYPE: DNA
<213> ORGANISM: Artificial Sequence
<220> FEATURE:
<223> OTHER INFORMATION: Synthetic construct

<400> SEQUENCE: 17

| | |
|---|---|
| gctagcgttt aaacttaagc ttgttgacta gtgagatcac agttctctct acagttactg | 60 |
| agcacacagg acctcaccat gggatggagc tgtatcatcc tcttcttggt agcaacagct | 120 |
| acaggtaagg ggctcacagt agcaggcttg aggtctggac atatatatgg gtgacaatga | 180 |
| catccacttt gcctttctct ccacaggtgt ccactcccag gttaccctga gagagtctgg | 240 |
| ccctgcgctg gtgaagccca cagaccct cacactgact tgtaccttct ctgggttttc | 300 |
| actgagcact tctggtatgg gtgtaggctg gattcgtcag cctcccggga aggctctaga | 360 |
| gtggctggca cacatttggt gggatgatga caagcgctat aatccagccc tgaagagccg | 420 |
| actgacaatc tccaaggata cctccaaaaa ccaggtagtc ctcacaatga ccaacatgga | 480 |
| ccctgtggat actgccacat actactgtgc tcggataaac cccgcctggt ttgcttactg | 540 |
| gggccaaggg actctggtca ctgtgagctc agcctccacc aagggcccat cggtcttccc | 600 |
| cctggcaccc tcctccaaga gcacctctgg gggcacagcg gccctgggct gcctggtcaa | 660 |
| ggactacttc cccgaaccgg tgacggtgtc gtggaactca ggcgccctga ccagcggcgt | 720 |
| gcacaccttc ccggctgtcc tacagtcctc aggactctac tccctcagca gcgtggtgac | 780 |
| cgtgccctcc agcagcttgg gcacccagac ctacatctgc aacgtgaatc acaagcccag | 840 |
| caacaccaag gtggacaaga gagttgagcc caaatcttgt gacaaaactc acacatgccc | 900 |
| accgtgccca gcacctgaac tcctgggggg accgtcagtc ttcctcttcc ccccaaaacc | 960 |
| caaggacacc ctcatgatct cccggacccc tgaggtcaca tgcgtggtgg tggacgtgag | 1020 |
| ccacgaagac cctgaggtca agttcaactg gtacgtggac ggcgtggagg tgcataatgc | 1080 |
| caagacaaag ccgcgggagg agcagtacaa cagcacgtac cgtgtggtca gcgtcctcac | 1140 |
| cgtcctgcac caggactggc tgaatggcaa ggagtacaag tgcaaggtct ccaacaaagc | 1200 |
| cctcccagcc cccatcgaga aaaccatctc caaagccaaa gggcagcccc gagaaccaca | 1260 |
| ggtgtacacc ctgcccccat cccgggatga gctgaccaag aaccaggtca gcctgacctg | 1320 |
| cctggtcaaa ggcttctatc ccagcgacat cgccgtggag tgggagagca atgggcagcc | 1380 |
| ggagaacaac tacaagacca cgcctcccgt gctggactcc gacggctcct tcttcctcta | 1440 |
| cagcaagctc accgtggaca agagcaggtg gcagcagggg aacgtcttct catgctccgt | 1500 |
| gatgcatgag gctctgcaca accactacac gcagaagagc ctctccctgt ctccgggtaa | 1560 |
| atgagtgcgg ccgcgaattc | 1580 |

<210> SEQ ID NO 18
<211> LENGTH: 63
<212> TYPE: DNA
<213> ORGANISM: Artificial Sequence
<220> FEATURE:
<223> OTHER INFORMATION: Primer

<400> SEQUENCE: 18

```
actctttggc tgtgtctcta ggggagaggg ccaccatcaa ctgcaaggcc agccaaagtg    60
ttg                                                                 63

<210> SEQ ID NO 19
<211> LENGTH: 66
<212> TYPE: DNA
<213> ORGANISM: Artificial Sequence
<220> FEATURE:
<223> OTHER INFORMATION: Primer

<400> SEQUENCE: 19
ctctccacag gtgtccactc cgacatcgtg atgacccaat ctccagactc tttggctgtg    60
tctcta                                                              66

<210> SEQ ID NO 20
<211> LENGTH: 71
<212> TYPE: DNA
<213> ORGANISM: Artificial Sequence
<220> FEATURE:
<223> OTHER INFORMATION: Primer

<400> SEQUENCE: 20
ggtgagggtg aagtctgtcc cagaccccact gccactaaac ctgtctggga ccccagattc    60
tagattggat g                                                         71

<210> SEQ ID NO 21
<211> LENGTH: 67
<212> TYPE: DNA
<213> ORGANISM: Artificial Sequence
<220> FEATURE:
<223> OTHER INFORMATION: Plasmid

<400> SEQUENCE: 21
tgacagtaat aaactgccac atcctcagcc tgcaggctgc tgatggtgag ggtgaagtct    60
gtcccag                                                             67

<210> SEQ ID NO 22
<211> LENGTH: 71
<212> TYPE: DNA
<213> ORGANISM: Artificial Sequence
<220> FEATURE:
<223> OTHER INFORMATION: Plasmid

<400> SEQUENCE: 22
gcggcaagct tggtcccctg tccgaacgtg tacggatcct cattactttg ctgacagtaa    60
taaactgcca c                                                        71

<210> SEQ ID NO 23
<211> LENGTH: 30
<212> TYPE: DNA
<213> ORGANISM: Artificial Sequence
<220> FEATURE:
<223> OTHER INFORMATION: Plasmid

<400> SEQUENCE: 23
cgagctagct gagatcacag ttctctctac                                    30

<210> SEQ ID NO 24
<211> LENGTH: 898
<212> TYPE: DNA
<213> ORGANISM: Artificial Sequence
<220> FEATURE:
```

<223> OTHER INFORMATION: Synthetic Construct

<400> SEQUENCE: 24

```
cgagctagct gagatcacag ttctctctac agttactgag cacacaggac ctcaccatgg      60
gatggagctg tatcatcctc ttcttggtag caacagctac aggtaagggg ctcacagtag     120
caggcttgag gtctggacat atatatgggt gacaatgaca tccactttgc ctttctctcc     180
acaggtgtcc actccgacat cgtgatgacc caatctccag actctttggc tgtgtctcta     240
ggggagaggg ccaccatcaa ctgcaagtcc agccaaagtg ttgattttga tggtgatagt     300
tttatgaact ggtaccaaca gaaaccagga cagccaccca aactcctcat ctatactaca     360
tccaatctag aaactggggt cccagacagg tttagtggca gtgggtctgg gacagacttc     420
accctcacca tcagcagcct gcaggctgag gatgtggcag tttattactg tcagcaaagt     480
aattcggatc cgtacacgtt cggacagggg accaagcttg agatcaaacg aactgtggct     540
gcaccatcgg tcttcatctt cccgccatct gatgagcagt tgaaatctgg aactgcctct     600
gttgtgtgcc tgctgaataa cttctatccc agagaggcca agtacagtg gaaggtggat     660
aacgccctcc aatcgggtaa ctcccaggag agtgtcacag agcaggacag caaggacagc     720
acctacagcc tcagcagcac cctgacgctg agcaaagcag actacgagaa acacaaagtc     780
tacgcctgcg aagtcaccca tcagggcctg agctcgcccg tcacaaagag cttcaacagg     840
ggagagtgtt agttctagag tcgactctag aggatccccg ggtaccgagc tcgaattc      898
```

<210> SEQ ID NO 25
<211> LENGTH: 333
<212> TYPE: DNA
<213> ORGANISM: Artificial Sequence
<220> FEATURE:
<223> OTHER INFORMATION: Synthetic Construct

<400> SEQUENCE: 25

```
gacactgtgc tgacccaatc tccagcttct ttggctgtgt ctctagggca gagggccacc      60
atctcctgca aggccagcca agtgttgat tttgatggtg atagttttat gaactggtac     120
caacagaaac caggacagcc acccaaactc ctcatctata ctacatccaa tctagaatct     180
gggatcccag ccaggtttag tggcagtggg tctgggacag acttcaccct caacatccat     240
cctgtggagg aggaggatac tgcaacctat tactgtcagc aaagtaatga ggatccgtac     300
acgttcggag ggggaccaa gcttgagatc aaa                                    333
```

<210> SEQ ID NO 26
<211> LENGTH: 895
<212> TYPE: DNA
<213> ORGANISM: Artificial Sequence
<220> FEATURE:
<223> OTHER INFORMATION: Synthetic Construct

<400> SEQUENCE: 26

```
gctagctgag atcacagttc tctctacagt tactgagcac acaggacctc accatgggat      60
ggagctgtat catcctcttc ttggtagcaa cagctacagg taaggggctc acagtagcag     120
gcttgaggtc tggacatata tatgggtgac aatgacatcc actttgcctt tctctccaca     180
ggtgtccact ccgacactgt gctgacccaa tctccagctt ctttggctgt gtctctaggg     240
cagagggcca ccatctcctg caaggccagc caaagtgttg attttgatgg tgatagtttt     300
atgaactggt accaacagaa accaggacag ccacccaaac tcctcatcta tactacatcc     360
aatctagaat ctgggatccc agccaggttt agtgccagtg ggtctgggac agacttcacc     420
```

```
ctcaacatcc atcctgtgga ggaggaggat actgcaacct attactgtca gcaaagtaat      480
gaggatccgt acacgttcgg agggggacc aagcttgaga tcaaacgaac tgtggctgca       540
ccatcggtct tcatcttccc gccatctgat gagcagttga atctggaac tgcctctgtt      600 gtgtgcctgc tgaataactt ctatcccaga gaggccaaag tacagtggaa ggtggataac     660
gccctccaat cgggtaactc ccaggagagt gtcacagagc aggacagcaa ggacagcacc     720
tacagcctca gcagcaccct gacgctgagc aaagcagact acgagaaaca caaagtctac     780
gcctgcgaag tcacccatca gggcctgagc tcgcccgtca caaagagctt caacagggga     840
gagtgttagt tctagagtcg actctagagg atccccgggt accgagctcg aattc           895
```

```
<210> SEQ ID NO 27
<211> LENGTH: 35
<212> TYPE: DNA
<213> ORGANISM: Artificial Sequence
<220> FEATURE:
<223> OTHER INFORMATION: Synthetic Construct

<400> SEQUENCE: 27
gttggatcct ccaactgctc tgctacttct agttt                                 35

<210> SEQ ID NO 28
<211> LENGTH: 34
<212> TYPE: DNA
<213> ORGANISM: Artificial Sequence
<220> FEATURE:
<223> OTHER INFORMATION: Synthetic Construct

<400> SEQUENCE: 28
gaaaagctta agaatgatg agatggttga cact                                   34

<210> SEQ ID NO 29
<211> LENGTH: 210
<212> TYPE: PRT
<213> ORGANISM: Artificial Sequence
<220> FEATURE:
<223> OTHER INFORMATION: Synthetic Construct

<400> SEQUENCE: 29
```

Met Trp Gln Leu Leu Pro Thr Ala Leu Leu Leu Val Ser Ala
 1               5                  10                  15

Gly Met Arg Thr Glu Asp Leu Pro Lys Ala Val Phe Leu Glu Pro
            20                  25                  30

Gln Trp Tyr Arg Val Leu Glu Lys Asp Ser Val Thr Leu Lys Cys Gln
        35                  40                  45

Gly Ala Tyr Ser Pro Glu Asp Asn Ser Thr Gln Trp Phe His Asn Glu
    50                  55                  60

Ser Leu Ile Ser Ser Gln Ala Ser Ser Tyr Phe Ile Asp Ala Ala Thr
65                  70                  75                  80

Val Asp Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
        115                 120                 125

His Ser Trp Lys Asn Thr Ala Leu His Lys Val Thr Tyr Leu Gln Asn
    130                 135                 140

Gly Lys Gly Arg Lys Tyr Phe His His Asn Ser Asp Phe Tyr Ile Pro

```
                145                 150                 155                 160
Lys Ala Thr Leu Lys Asp Ser Gly Ser Tyr Phe Cys Arg Gly Leu Phe
                165                 170                 175
Gly Ser Lys Asn Val Ser Ser Glu Thr Val Asn Ile Thr Ile Thr Gln
            180                 185                 190
Gly Leu Ala Val Ser Thr Ile Ser Ser Phe Phe Lys Leu Ala Ala Ala
        195                 200                 205
Arg Val
    210

<210> SEQ ID NO 30
<211> LENGTH: 30
<212> TYPE: PRT
<213> ORGANISM: Artificial Sequence
<220> FEATURE:
<223> OTHER INFORMATION: Synthetic Construct

<400> SEQUENCE: 30

Gln Val Thr Leu Lys Glu Ser Gly Pro Gly Ile Leu Gln Pro Ser Gln
1               5                   10                  15
Thr Leu Ser Leu Thr Cys Ser Phe Ser Gly Phe Ser Leu Arg
            20                  25                  30

<210> SEQ ID NO 31
<211> LENGTH: 30
<212> TYPE: PRT
<213> ORGANISM: Artificial Sequence
<220> FEATURE:
<223> OTHER INFORMATION: Synthetic Construct

<400> SEQUENCE: 31

Gln Val Thr Leu Arg Glu Ser Gly Pro Ala Leu Val Lys Pro Thr Gln
1               5                   10                  15
Thr Leu Thr Leu Thr Cys Thr Phe Ser Gly Phe Ser Leu Ser
            20                  25                  30

<210> SEQ ID NO 32
<211> LENGTH: 30
<212> TYPE: PRT
<213> ORGANISM: Artificial Sequence
<220> FEATURE:
<223> OTHER INFORMATION: Synthetic Construct

<400> SEQUENCE: 32

Gln Val Thr Leu Lys Glu Ser Gly Pro Ala Leu Val Lys Pro Thr Gln
1               5                   10                  15
Thr Leu Thr Leu Thr Cys Thr Phe Ser Gly Phe Ser Leu Ser
            20                  25                  30

<210> SEQ ID NO 33
<211> LENGTH: 30
<212> TYPE: PRT
<213> ORGANISM: Artificial Sequence
<220> FEATURE:
<223> OTHER INFORMATION: Synthetic Construct

<400> SEQUENCE: 33

Gln Val Thr Leu Arg Glu Ser Gly Pro Ala Leu Val Lys Pro Thr Gln
1               5                   10                  15
Thr Leu Thr Leu Thr Cys Thr Phe Ser Gly Phe Ser Leu Arg
            20                  25                  30
```

```
<210> SEQ ID NO 34
<211> LENGTH: 30
<212> TYPE: PRT
<213> ORGANISM: Artificial Sequence
<220> FEATURE:
<223> OTHER INFORMATION: Synthetic Construct

<400> SEQUENCE: 34

Gln Ile Thr Leu Lys Glu Ser Gly Pro Thr Leu Val Lys Pro Thr Gln
 1               5                  10                  15

Thr Leu Thr Leu Thr Cys Thr Phe Ser Gly Phe Ser Leu Ser
            20                  25                  30

<210> SEQ ID NO 35
<211> LENGTH: 7
<212> TYPE: PRT
<213> ORGANISM: Artificial Sequence
<220> FEATURE:
<223> OTHER INFORMATION: Synthetic Construct

<400> SEQUENCE: 35

Thr Ser Gly Met Gly Val Gly
 1               5

<210> SEQ ID NO 36
<211> LENGTH: 7
<212> TYPE: PRT
<213> ORGANISM: Artificial Sequence
<220> FEATURE:
<223> OTHER INFORMATION: Synthetic Construct

<400> SEQUENCE: 36

Thr Ser Gly Val Gly Val Gly
 1               5

<210> SEQ ID NO 37
<211> LENGTH: 14
<212> TYPE: PRT
<213> ORGANISM: Artificial Sequence
<220> FEATURE:
<223> OTHER INFORMATION: Synthetic Construct

<400> SEQUENCE: 37

Trp Ile Arg Gln Pro Ser Gly Lys Gly Leu Glu Trp Leu Ala
 1               5                  10

<210> SEQ ID NO 38
<211> LENGTH: 14
<212> TYPE: PRT
<213> ORGANISM: Artificial Sequence
<220> FEATURE:
<223> OTHER INFORMATION: Synthetic Construct

<400> SEQUENCE: 38

Trp Ile Arg Gln Pro Pro Gly Lys Ala Leu Glu Trp Leu Ala
 1               5                  10

<210> SEQ ID NO 39
<211> LENGTH: 16
<212> TYPE: PRT
<213> ORGANISM: Artificial Sequence
<220> FEATURE:
<223> OTHER INFORMATION: Synthetic Construct

<400> SEQUENCE: 39

His Ile Trp Trp Asp Asp Asp Lys Arg Tyr Asn Pro Ala Leu Lys Ser
 1               5                  10                  15
```

-continued

<210> SEQ ID NO 40
<211> LENGTH: 16
<212> TYPE: PRT
<213> ORGANISM: Artificial Sequence
<220> FEATURE:
<223> OTHER INFORMATION: Synthetic Construct

<400> SEQUENCE: 40

His Ile Tyr Trp Asn Asp Asp Lys Arg Tyr Asn Pro Ala Leu Lys Ser
1               5                   10                  15

<210> SEQ ID NO 41
<211> LENGTH: 16
<212> TYPE: PRT
<213> ORGANISM: Artificial Sequence
<220> FEATURE:
<223> OTHER INFORMATION: Synthetic Construct

<400> SEQUENCE: 41

His Ile Trp Trp Asp Asp Asp Lys Arg Tyr Ser Pro Ser Leu Lys Ser
1               5                   10                  15

<210> SEQ ID NO 42
<211> LENGTH: 16
<212> TYPE: PRT
<213> ORGANISM: Artificial Sequence
<220> FEATURE:
<223> OTHER INFORMATION: Synthetic Construct

<400> SEQUENCE: 42

His Ile Tyr Trp Asp Asp Asp Lys Arg Tyr Asn Pro Ala Leu Lys Ser
1               5                   10                  15

<210> SEQ ID NO 43
<211> LENGTH: 16
<212> TYPE: PRT
<213> ORGANISM: Artificial Sequence
<220> FEATURE:
<223> OTHER INFORMATION: Synthetic Construct

<400> SEQUENCE: 43

His Ile Trp Trp Asn Asp Asp Lys Arg Tyr Asn Pro Ala Leu Lys Ser
1               5                   10                  15

<210> SEQ ID NO 44
<211> LENGTH: 16
<212> TYPE: PRT
<213> ORGANISM: Artificial Sequence
<220> FEATURE:
<223> OTHER INFORMATION: Synthetic Construct

<400> SEQUENCE: 44

Leu Ile Asp Trp Asp Asp Asp Lys Arg Tyr Ser Pro Ser Leu Lys Ser
1               5                   10                  15

<210> SEQ ID NO 45
<211> LENGTH: 16
<212> TYPE: PRT
<213> ORGANISM: Artificial Sequence
<220> FEATURE:
<223> OTHER INFORMATION: Synthetic Construct

<400> SEQUENCE: 45

His Ile Phe Trp Asp Asp Asp Lys Arg Tyr Ser Pro Ser Leu Lys Ser
1               5                   10                  15

```
<210> SEQ ID NO 46
<211> LENGTH: 16
<212> TYPE: PRT
<213> ORGANISM: Artificial Sequence
<220> FEATURE:
<223> OTHER INFORMATION: Synthetic Construct

<400> SEQUENCE: 46

Leu Ile Trp Trp Asp Asp Asp Lys Arg Tyr Ser Pro Ser Leu Lys Ser
 1               5                  10                  15

<210> SEQ ID NO 47
<211> LENGTH: 16
<212> TYPE: PRT
<213> ORGANISM: Artificial Sequence
<220> FEATURE:
<223> OTHER INFORMATION: Synthetic Construct

<400> SEQUENCE: 47

His Ile Asp Trp Asp Asp Asp Lys Arg Tyr Ser Pro Ser Leu Lys Ser
 1               5                  10                  15

<210> SEQ ID NO 48
<211> LENGTH: 16
<212> TYPE: PRT
<213> ORGANISM: Artificial Sequence
<220> FEATURE:
<223> OTHER INFORMATION: Synthetic Construct

<400> SEQUENCE: 48

Leu Ile Trp Trp Asn Asp Asp Lys Arg Tyr Ser Pro Ser Leu Lys Ser
 1               5                  10                  15

<210> SEQ ID NO 49
<211> LENGTH: 32
<212> TYPE: PRT
<213> ORGANISM: Artificial Sequence
<220> FEATURE:
<223> OTHER INFORMATION: Synthetic Construct

<400> SEQUENCE: 49

Arg Leu Thr Ile Ser Lys Asp Thr Ser Ser Asn Gln Val Phe Leu Lys
 1               5                  10                  15

Ile Ala Ser Val Asp Thr Ala Asp Thr Ala Thr Tyr Tyr Cys Ala Gln
                20                  25                  30

<210> SEQ ID NO 50
<211> LENGTH: 32
<212> TYPE: PRT
<213> ORGANISM: Artificial Sequence
<220> FEATURE:
<223> OTHER INFORMATION: Synthetic Construct

<400> SEQUENCE: 50

Arg Leu Thr Ile Ser Lys Asp Thr Ser Lys Asn Gln Val Val Leu Thr
 1               5                  10                  15

Met Thr Asn Met Asp Pro Val Asp Thr Ala Thr Tyr Tyr Cys Ala Arg
                20                  25                  30

<210> SEQ ID NO 51
<211> LENGTH: 32
<212> TYPE: PRT
<213> ORGANISM: Artificial Sequence
<220> FEATURE:
<223> OTHER INFORMATION: Synthetic Construct
```

<400> SEQUENCE: 51

Arg Leu Thr Ile Ser Lys Asp Thr Ser Lys Asn Gln Val Val Leu Thr
1               5                   10                  15

Met Thr Asn Met Asp Pro Val Asp Thr Ala Thr Tyr Tyr Cys Ala Gln
            20                  25                  30

<210> SEQ ID NO 52
<211> LENGTH: 32
<212> TYPE: PRT
<213> ORGANISM: Artificial Sequence
<220> FEATURE:
<223> OTHER INFORMATION: Synthetic Construct

<400> SEQUENCE: 52

Arg Leu Thr Ile Ser Lys Asp Thr Ser Lys Asn Gln Val Val Leu Thr
1               5                   10                  15

Met Thr Asn Met Asp Pro Val Asp Thr Ala Thr Tyr Tyr Cys Ala Thr
            20                  25                  30

<210> SEQ ID NO 53
<211> LENGTH: 32
<212> TYPE: PRT
<213> ORGANISM: Artificial Sequence
<220> FEATURE:
<223> OTHER INFORMATION: Synthetic Construct

<400> SEQUENCE: 53

Arg Leu Thr Ile Ser Lys Asp Thr Ser Lys Asn Gln Val Val Leu Thr
1               5                   10                  15

Met Thr Asn Met Asp Pro Val Asp Thr Ala Thr Tyr Tyr Cys Ala Lys
            20                  25                  30

<210> SEQ ID NO 54
<211> LENGTH: 32
<212> TYPE: PRT
<213> ORGANISM: Artificial Sequence
<220> FEATURE:
<223> OTHER INFORMATION: Synthetic Construct

<400> SEQUENCE: 54

Arg Leu Thr Ile Ser Lys Asp Thr Ser Lys Asn Gln Val Val Leu Thr
1               5                   10                  15

Met Thr Asn Met Asp Pro Val Asp Thr Ala Thr Tyr Tyr Cys Ala Ala
            20                  25                  30

<210> SEQ ID NO 55
<211> LENGTH: 32
<212> TYPE: PRT
<213> ORGANISM: Artificial Sequence
<220> FEATURE:
<223> OTHER INFORMATION: Synthetic Construct

<400> SEQUENCE: 55

Arg Leu Thr Ile Ser Lys Asp Thr Ser Lys Asn Gln Val Val Leu Thr
1               5                   10                  15

Met Thr Asn Met Asp Pro Val Asp Thr Ala Thr Tyr Tyr Cys Ala His
            20                  25                  30

<210> SEQ ID NO 56
<211> LENGTH: 32
<212> TYPE: PRT
<213> ORGANISM: Artificial Sequence
<220> FEATURE:
<223> OTHER INFORMATION: Synthetic Construct

<400> SEQUENCE: 56

Arg Leu Thr Ile Thr Lys Asp Thr Ser Lys Asn Gln Val Val Leu Thr
1               5                   10                  15
Met Thr Asn Met Asp Pro Val Asp Thr Ala Thr Tyr Tyr Cys Ala Arg
            20                  25                  30

<210> SEQ ID NO 57
<211> LENGTH: 32
<212> TYPE: PRT
<213> ORGANISM: Artificial Sequence
<220> FEATURE:
<223> OTHER INFORMATION: Synthetic Construct

<400> SEQUENCE: 57

Arg Leu Thr Ile Thr Lys Asp Thr Ser Lys Asn Gln Val Val Leu Thr
1               5                   10                  15
Met Thr Asn Met Asp Pro Val Asp Thr Ala Thr Tyr Tyr Cys Ala His
            20                  25                  30

<210> SEQ ID NO 58
<211> LENGTH: 32
<212> TYPE: PRT
<213> ORGANISM: Artificial Sequence
<220> FEATURE:
<223> OTHER INFORMATION: Synthetic Construct

<400> SEQUENCE: 58

Arg Leu Thr Ile Thr Lys Asp Thr Ser Lys Asn Gln Val Val Leu Thr
1               5                   10                  15
Met Thr Asn Met Asp Pro Val Asp Thr Ala Thr Tyr Tyr Cys Ala Gln
            20                  25                  30

<210> SEQ ID NO 59
<211> LENGTH: 8
<212> TYPE: PRT
<213> ORGANISM: Artificial Sequence
<220> FEATURE:
<223> OTHER INFORMATION: Synthetic Construct

<400> SEQUENCE: 59

Ile Asn Pro Ala Trp Phe Ala Tyr
1               5

<210> SEQ ID NO 60
<211> LENGTH: 8
<212> TYPE: PRT
<213> ORGANISM: Artificial Sequence
<220> FEATURE:
<223> OTHER INFORMATION: Synthetic Construct

<400> SEQUENCE: 60

Ile Asn Pro Ala Trp Phe Asp Tyr
1               5

<210> SEQ ID NO 61
<211> LENGTH: 8
<212> TYPE: PRT
<213> ORGANISM: Artificial Sequence
<220> FEATURE:
<223> OTHER INFORMATION: Synthetic Construct

<400> SEQUENCE: 61

Ile Asn Pro Ala Tyr Phe Ala Tyr
1               5

```
<210> SEQ ID NO 62
<211> LENGTH: 8
<212> TYPE: PRT
<213> ORGANISM: Artificial Sequence
<220> FEATURE:
<223> OTHER INFORMATION: Synthetic Construct

<400> SEQUENCE: 62

Ile Asn Pro Ala Tyr Phe Asp Tyr
1               5

<210> SEQ ID NO 63
<211> LENGTH: 11
<212> TYPE: PRT
<213> ORGANISM: Artificial Sequence
<220> FEATURE:
<223> OTHER INFORMATION: Synthetic Construct

<400> SEQUENCE: 63

Trp Gly Gln Gly Thr Leu Val Thr Val Ser Ala
1               5                   10

<210> SEQ ID NO 64
<211> LENGTH: 11
<212> TYPE: PRT
<213> ORGANISM: Artificial Sequence
<220> FEATURE:
<223> OTHER INFORMATION: Synthetic Construct

<400> SEQUENCE: 64

Trp Gly Gln Gly Thr Leu Val Thr Val Ser Ser
1               5                   10

<210> SEQ ID NO 65
<211> LENGTH: 23
<212> TYPE: PRT
<213> ORGANISM: Artificial Sequence
<220> FEATURE:
<223> OTHER INFORMATION: Synthetic Construct

<400> SEQUENCE: 65

Asp Thr Val Leu Thr Gln Ser Pro Ala Ser Leu Ala Val Ser Leu Gly
1               5                   10                  15

Gln Arg Ala Thr Ile Ser Cys
            20

<210> SEQ ID NO 66
<211> LENGTH: 23
<212> TYPE: PRT
<213> ORGANISM: Artificial Sequence
<220> FEATURE:
<223> OTHER INFORMATION: Synthetic Construct

<400> SEQUENCE: 66

Asp Ile Val Met Thr Gln Ser Pro Asp Ser Leu Ala Val Ser Leu Gly
1               5                   10                  15

Glu Arg Ala Thr Ile Asn Cys
            20

<210> SEQ ID NO 67
<211> LENGTH: 15
<212> TYPE: PRT
<213> ORGANISM: Artificial Sequence
<220> FEATURE:
<223> OTHER INFORMATION: Synthetic Construct
```

-continued

<400> SEQUENCE: 67

Lys Ala Ser Gln Ser Val Asp Phe Asp Gly Asp Ser Phe Met Asn
1               5                   10                  15

<210> SEQ ID NO 68
<211> LENGTH: 15
<212> TYPE: PRT
<213> ORGANISM: Artificial Sequence
<220> FEATURE:
<223> OTHER INFORMATION: Synthetic Construct

<400> SEQUENCE: 68

Arg Ala Ser Gln Ser Val Asp Phe Asp Gly Asp Ser Phe Met Asn
1               5                   10                  15

<210> SEQ ID NO 69
<211> LENGTH: 15
<212> TYPE: PRT
<213> ORGANISM: Artificial Sequence
<220> FEATURE:
<223> OTHER INFORMATION: Synthetic Construct

<400> SEQUENCE: 69

Lys Ser Ser Gln Ser Val Asp Phe Asp Gly Asp Ser Phe Met Asn
1               5                   10                  15

<210> SEQ ID NO 70
<211> LENGTH: 15
<212> TYPE: PRT
<213> ORGANISM: Artificial Sequence
<220> FEATURE:
<223> OTHER INFORMATION: Synthetic Construct

<400> SEQUENCE: 70

Lys Ala Ser Gln Ser Val Asp Phe Asp Gly Asp Ser Tyr Met Asn
1               5                   10                  15

<210> SEQ ID NO 71
<211> LENGTH: 15
<212> TYPE: PRT
<213> ORGANISM: Artificial Sequence
<220> FEATURE:
<223> OTHER INFORMATION: Synthetic Construct

<400> SEQUENCE: 71

Lys Ala Ser Gln Ser Val Asp Phe Asp Gly Asp Ser Phe Leu Asn
1               5                   10                  15

<210> SEQ ID NO 72
<211> LENGTH: 15
<212> TYPE: PRT
<213> ORGANISM: Artificial Sequence
<220> FEATURE:
<223> OTHER INFORMATION: Synthetic Construct

<400> SEQUENCE: 72

Lys Ala Ser Gln Ser Val Asp Phe Asp Gly Asp Ser Phe Met Ala
1               5                   10                  15

<210> SEQ ID NO 73
<211> LENGTH: 15
<212> TYPE: PRT
<213> ORGANISM: Artificial Sequence
<220> FEATURE:
<223> OTHER INFORMATION: Synthetic Construct

```
<400> SEQUENCE: 73

Lys Ala Ser Gln Ser Val Asp Phe Asp Gly Asp Ser Tyr Leu Ala
1               5                   10                  15

<210> SEQ ID NO 74
<211> LENGTH: 15
<212> TYPE: PRT
<213> ORGANISM: Artificial Sequence
<220> FEATURE:
<223> OTHER INFORMATION: Synthetic Construct

<400> SEQUENCE: 74

Trp Tyr Gln Gln Lys Pro Gly Gln Pro Pro Lys Leu Leu Ile Tyr
1               5                   10                  15

<210> SEQ ID NO 75
<211> LENGTH: 7
<212> TYPE: PRT
<213> ORGANISM: Artificial Sequence
<220> FEATURE:
<223> OTHER INFORMATION: Synthetic Construct

<400> SEQUENCE: 75

Thr Thr Ser Asn Leu Glu Ser
1               5

<210> SEQ ID NO 76
<211> LENGTH: 7
<212> TYPE: PRT
<213> ORGANISM: Artificial Sequence
<220> FEATURE:
<223> OTHER INFORMATION: Synthetic Construct

<400> SEQUENCE: 76

Asp Ala Ser Asn Leu Glu Ser
1               5

<210> SEQ ID NO 77
<211> LENGTH: 7
<212> TYPE: PRT
<213> ORGANISM: Artificial Sequence
<220> FEATURE:
<223> OTHER INFORMATION: Synthetic Construct

<400> SEQUENCE: 77

Trp Ala Ser Asn Leu Glu Ser
1               5

<210> SEQ ID NO 78
<211> LENGTH: 7
<212> TYPE: PRT
<213> ORGANISM: Artificial Sequence
<220> FEATURE:
<223> OTHER INFORMATION: Synthetic Construct

<400> SEQUENCE: 78

Thr Thr Ser Asn Leu Glu Thr
1               5

<210> SEQ ID NO 79
<211> LENGTH: 7
<212> TYPE: PRT
<213> ORGANISM: Artificial Sequence
<220> FEATURE:
<223> OTHER INFORMATION: Synthetic Construct

<400> SEQUENCE: 79
```

Asp Ala Ser Asn Leu Glu Thr
1               5

<210> SEQ ID NO 80
<211> LENGTH: 7
<212> TYPE: PRT
<213> ORGANISM: Artificial Sequence
<220> FEATURE:
<223> OTHER INFORMATION: Synthetic Construct

<400> SEQUENCE: 80

Asp Ala Ser Asn Leu Ala Thr
1               5

<210> SEQ ID NO 81
<211> LENGTH: 7
<212> TYPE: PRT
<213> ORGANISM: Artificial Sequence
<220> FEATURE:
<223> OTHER INFORMATION: Synthetic Construct

<400> SEQUENCE: 81

Ser Ala Ser Asn Leu Gln Ser
1               5

<210> SEQ ID NO 82
<211> LENGTH: 7
<212> TYPE: PRT
<213> ORGANISM: Artificial Sequence
<220> FEATURE:
<223> OTHER INFORMATION: Synthetic Construct

<400> SEQUENCE: 82

Ser Thr Ser Asn Leu Glu Ser
1               5

<210> SEQ ID NO 83
<211> LENGTH: 7
<212> TYPE: PRT
<213> ORGANISM: Artificial Sequence
<220> FEATURE:
<223> OTHER INFORMATION: Synthetic Construct

<400> SEQUENCE: 83

Ser Thr Ser Asn Leu Gln Ser
1               5

<210> SEQ ID NO 84
<211> LENGTH: 7
<212> TYPE: PRT
<213> ORGANISM: Artificial Sequence
<220> FEATURE:
<223> OTHER INFORMATION: Synthetic Construct

<400> SEQUENCE: 84

Thr Thr Ser Asn Leu Gln Ser
1               5

<210> SEQ ID NO 85
<211> LENGTH: 7
<212> TYPE: PRT
<213> ORGANISM: Artificial Sequence
<220> FEATURE:
<223> OTHER INFORMATION: Synthetic Construct

<400> SEQUENCE: 85

```
Thr Thr Ser Ser Leu Gln Ser
  1               5
```

<210> SEQ ID NO 86
<211> LENGTH: 32
<212> TYPE: PRT
<213> ORGANISM: Artificial Sequence
<220> FEATURE:
<223> OTHER INFORMATION: Synthetic Construct

<400> SEQUENCE: 86

```
Gly Ile Pro Ala Arg Phe Ser Ala Ser Gly Ser Gly Thr Asp Phe Thr
  1               5                  10                  15

Leu Asn Ile His Pro Val Glu Glu Glu Asp Thr Ala Thr Tyr Tyr Cys
             20                  25                  30
```

<210> SEQ ID NO 87
<211> LENGTH: 32
<212> TYPE: PRT
<213> ORGANISM: Artificial Sequence
<220> FEATURE:
<223> OTHER INFORMATION: Synthetic Construct

<400> SEQUENCE: 87

```
Gly Val Pro Asp Arg Phe Ser Gly Ser Gly Ser Gly Thr Asp Phe Thr
  1               5                  10                  15

Leu Thr Ile Ser Ser Leu Gln Ala Glu Asp Val Ala Val Tyr Tyr Cys
             20                  25                  30
```

<210> SEQ ID NO 88
<211> LENGTH: 9
<212> TYPE: PRT
<213> ORGANISM: Artificial Sequence
<220> FEATURE:
<223> OTHER INFORMATION: Synthetic Construct

<400> SEQUENCE: 88

```
Gln Gln Ser Asn Glu Asp Pro Tyr Thr
  1               5
```

<210> SEQ ID NO 89
<211> LENGTH: 9
<212> TYPE: PRT
<213> ORGANISM: Artificial Sequence
<220> FEATURE:
<223> OTHER INFORMATION: Synthetic Construct

<400> SEQUENCE: 89

```
Gln Gln Ser Tyr Ser Thr Pro Tyr Thr
  1               5
```

<210> SEQ ID NO 90
<211> LENGTH: 9
<212> TYPE: PRT
<213> ORGANISM: Artificial Sequence
<220> FEATURE:
<223> OTHER INFORMATION: Synthetic Construct

<400> SEQUENCE: 90

```
Gln Gln Ser Tyr Glu Asp Pro Tyr Thr
  1               5
```

<210> SEQ ID NO 91
<211> LENGTH: 9
<212> TYPE: PRT
<213> ORGANISM: Artificial Sequence

```
<220> FEATURE:
<223> OTHER INFORMATION: Synthetic Construct

<400> SEQUENCE: 91

Gln Gln Ser Asn Ser Asp Pro Tyr Thr
 1               5

<210> SEQ ID NO 92
<211> LENGTH: 9
<212> TYPE: PRT
<213> ORGANISM: Artificial Sequence
<220> FEATURE:
<223> OTHER INFORMATION: Synthetic Construct

<400> SEQUENCE: 92

Gln Gln Ser Asn Glu Thr Pro Tyr Thr
 1               5

<210> SEQ ID NO 93
<211> LENGTH: 10
<212> TYPE: PRT
<213> ORGANISM: Artificial Sequence
<220> FEATURE:
<223> OTHER INFORMATION: Synthetic Construct

<400> SEQUENCE: 93

Phe Gly Gly Gly Thr Lys Leu Glu Ile Lys
 1               5                  10

<210> SEQ ID NO 94
<211> LENGTH: 10
<212> TYPE: PRT
<213> ORGANISM: Artificial Sequence
<220> FEATURE:
<223> OTHER INFORMATION: Synthetic Construct

<400> SEQUENCE: 94

Phe Gly Gln Gly Thr Lys Leu Glu Ile Lys
 1               5                  10

<210> SEQ ID NO 95
<211> LENGTH: 528
<212> TYPE: DNA
<213> ORGANISM: Artificial Sequence
<220> FEATURE:
<223> OTHER INFORMATION: Synthetic Construct

<400> SEQUENCE: 95
cgagctagct gagatcacag ttctctctac agttactgag cacacaggac ctcaccatgg      60
gatggagctg tatcatcctc ttcttggtag caacagctac aggtaagggg ctcacagtag     120
caggcttgag gtctggacat atatatgggt gacaatgaca tccactttgc ctttctctcc     180
acaggtgtcc actccgacat cgtgatgacc caatctccag actctttggc tgtgtctcta     240
ggggagaggg ccaccatcaa ctgcaaggcc agccaaagtg ttgattttga tggtgatagt     300
tttatgaact ggtaccaaca gaaaccagga cagccaccca aactcctcat ctatactaca     360
tccaatctag aatctggggt cccagacagg tttagtggca gtgggtctgg gacagacttc     420
accctcacca tcagcagcct gcaggctgag gatgtggcag tttattactg tcagcaaagt     480
aatgaggatc cgtacacgtt cggacagggg accaagcttg agatcaaa                  528

<210> SEQ ID NO 96
<211> LENGTH: 111
<212> TYPE: PRT
```

<213> ORGANISM: Artificial Sequence
<220> FEATURE:
<223> OTHER INFORMATION: Synthetic Construct

<400> SEQUENCE: 96

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Asp Phe Asp
            20                  25                  30

Gly Asp Ser Phe Met Asn Trp Tyr Gln Gln Lys Pro Gly Gln Pro Pro
        35                  40                  45

Lys Leu Leu Ile Tyr Thr Thr Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

Glu Asp Pro Tyr Thr Phe Gly Gln Gly Thr Lys Leu Glu Ile Lys
            100                 105                 110

<210> SEQ ID NO 97
<211> LENGTH: 897
<212> TYPE: DNA
<213> ORGANISM: Artificial Sequence
<220> FEATURE:
<223> OTHER INFORMATION: Synthetic Construct

<400> SEQUENCE: 97
cgagctagct gagatcacag ttctctctac agttactgag cacacaggac ctcaccatgg      60
gatggagctg tatcatcctc ttcttggtag caacagctac aggtaagggg ctcacagtag     120
caggcttgag gtctggacat atatatgggt gacaatgaca tccactttgc ctttctctcc     180
acaggtgtcc actccgacat cgtgatgacc caatctccag actctttggc tgtgtctcta     240
ggggagaggg ccaccatcaa ctgcaaggcc agccaaagtg ttgattttga tggtgatagt     300
tttatgaact ggtaccaaca gaaaccagga cagccaccca aactcctcat ctatactaca     360
tccaatctag aatctggggt cccagacagg tttagtggca gtgggtctgg acagacttc     420
accctcacca tcagcagcct gcaggctgag gatgtggcag tttattactg tcagcaaagt     480
aatgaggatc cgtacacgtt cggacagggg accaagcttg agatcaaacg aactgtggct     540
gcaccatcgg tcttcatctt cccgccatct gatgagcagt tgaaatctgg aactgcctct     600
gttgtgtgcc tgctgaataa cttctatccc agagaggcca agtacagtg gaaggtggat     660
aacgccctcc aatcgggtaa ctcccaggag agtgtcacag agcaggacag caaggacagc     720
acctacagcc tcagcagcac cctgacgctg agcaaagcag actacgagaa acacaaagtc     780
tacgctgcga agtcacccat cagggcctga gctcgcccgt cacaaagagc ttcaacaggg     840
gagagtgtta gttctagagt cgactctaga ggatccccgg gtaccgagct cgaattc       897

<210> SEQ ID NO 98
<211> LENGTH: 218
<212> TYPE: PRT
<213> ORGANISM: Artificial Sequence
<220> FEATURE:
<223> OTHER INFORMATION: Synthetic Construct

<400> SEQUENCE: 98

Asp Ile Val Met Thr Gln Ser Pro Asp Ser Leu Ala Val Ser Leu Gly
1               5                   10                  15

-continued

```
Glu Arg Ala Thr Ile Asn Cys Lys Ala Ser Gln Ser Val Asp Phe Asp
             20                  25                  30

Gly Asp Ser Phe Met Asn Trp Tyr Gln Gln Lys Pro Gly Gln Pro Pro
         35                  40                  45

Lys Leu Leu Ile Tyr Thr Thr Ser Asn Leu Glu Ser Gly Val Pro Asp
     50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln Ser Asn
                 85                  90                  95

Glu Asp Pro Tyr Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 99
<211> LENGTH: 528
<212> TYPE: DNA
<213> ORGANISM: Artificial Sequence
<220> FEATURE:
<223> OTHER INFORMATION: Synthetic Construct

<400> SEQUENCE: 99

```
cgagctagct gagatcacag ttctctctac agttactgag cacacaggac ctcaccatgg    60
gatggagctg tatcatcctc ttcttggtag caacagctac aggtaagggg ctcacagtag   120
caggcttgag gtctggacat atatatgggt gacaatgaca tccactttgc ctttctctcc   180
acaggtgtcc actccgacat cgtgatgacc caatctccag actctttggc tgtgtctcta   240
ggggagaggg ccaccatcaa ctgcaagtcc agccaaagtg ttgattttga tggtgatagt   300
tttatgaact ggtaccaaca gaaaccagga cagcccaccc aactcctcat ctatactaca   360
tccagtctag aatctggggt cccagacagg tttagtggca gtgggtctgg acagacttc   420
accctcacca tcagcagcct gcaggctgag gatgtgcag tttattactg tcagcaaagt   480
aattcggatc cgtacacgtt cggacagggg accaagcttg agatcaaa              528
```

<210> SEQ ID NO 100
<211> LENGTH: 111
<212> TYPE: PRT
<213> ORGANISM: Artificial Sequence
<220> FEATURE:
<223> OTHER INFORMATION: Synthetic Construct

<400> SEQUENCE: 100

Asp Ile Val Met Thr Gln Ser Pro Asp Ser Leu Ala Val Ser Leu Gly

```
                1               5              10              15
Glu Arg Ala Thr Ile Asn Cys Lys Ser Ser Gln Ser Val Asp Phe Asp
                20                  25                  30

Gly Asp Ser Phe Met Asn Trp Tyr Gln Gln Lys Pro Gly Gln Pro Pro
            35                  40                  45

Lys Leu Leu Ile Tyr Thr Thr Ser Ser Leu Glu Ser Gly Val Pro Asp
        50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

Ser Asp Pro Tyr Thr Phe Gly Gln Gly Thr Lys Leu Glu Ile Lys
                100                 105                 110
```

<210> SEQ ID NO 101
<211> LENGTH: 898
<212> TYPE: DNA
<213> ORGANISM: Artificial Sequence
<220> FEATURE:
<223> OTHER INFORMATION: Synthetic Construct

<400> SEQUENCE: 101

| | | |
|---|---|---|
| cgagctagct gagatcacag ttctctctac agttactgag cacacaggac ctcaccatgg | 60 |
| gatggagctg tatcatcctc ttcttggtag caacagctac aggtaagggg ctcacagtag | 120 |
| caggcttgag gtctggacat atatatgggt gacaatgaca tccactttgc ctttctctcc | 180 |
| acaggtgtcc actccgacat cgtgatgacc caatctccag actctttggc tgtgtctcta | 240 |
| ggggagaggg ccaccatcaa ctgcaagtcc agccaaagtg ttgattttga tggtgatagt | 300 |
| tttatgaact ggtaccaaca gaaaccagga cagccaccca aactcctcat ctatactaca | 360 |
| tccagtctag aatctggggt cccagacagg tttagtggca gtgggtctgg gacagacttc | 420 |
| accctcacca tcagcagcct gcaggctgag gatgtggcag tttattactg tcagcaaagt | 480 |
| aattcggatc cgtacacgtt cggacagggg accaagcttg agatcaaacg aactgtggct | 540 |
| gcaccatcgg tcttcatctt cccgccatct gatgagcagt tgaaatctgg aactgcctct | 600 |
| gttgtgtgcc tgctgaataa cttctatccc agagaggcca agtacagtg aaggtggat | 660 |
| aacgccctcc aatcgggtaa ctcccaggag agtgtcacag agcaggacag caaggacagc | 720 |
| acctacagcc tcagcagcac cctgacgctg agcaaagcag actacgagaa acacaaagtc | 780 |
| tacgcctgcg aagtcaccca tcagggcctg agctcgcccg tcacaaagag cttcaacagg | 840 |
| ggagagtgtt agttctagag tcgactctag aggatccccg ggtaccgagc tcgaattc | 898 |

<210> SEQ ID NO 102
<211> LENGTH: 218
<212> TYPE: PRT
<213> ORGANISM: Artificial Sequence
<220> FEATURE:
<223> OTHER INFORMATION: Synthetic Construct

<400> SEQUENCE: 102

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Asp Phe Asp
                20                  25                  30

Gly Asp Ser Phe Met Asn Trp Tyr Gln Gln Lys Pro Gly Gln Pro Pro
            35                  40                  45
```

-continued

Lys Leu Leu Ile Tyr Thr Thr Ser Ser Leu Glu Ser Gly Val Pro Asp
 50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln Ser Asn
                 85                  90                  95

Ser Asp Pro Tyr Thr Phe Gly Gln Gly Thr Lys Leu Glu Ile Lys Arg
             100                 105                 110

Thr Val Ala Ala Pro Ser Val Phe Ile Phe Pro Pro Ser Asp Glu Gln
         115                 120                 125

Leu Lys Ser Gly Thr Ala Ser Val Val Cys Leu Leu Asn Asn Phe Tyr
 130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 103
<211> LENGTH: 571
<212> TYPE: DNA
<213> ORGANISM: Artificial Sequence
<220> FEATURE:
<223> OTHER INFORMATION: Synthetic Construct

<400> SEQUENCE: 103
gctagcgttt aaacttaagc ttgttgacta gtgagatcac agttctctct acagttactg      60
agcacacagg acctcaccat gggatggagc tgtatcatcc tcttcttggt agcaacagct     120
acaggtaagg ggctcacagt agcaggcttg aggtctggac atatatatgg gtgacaatga     180
catccacttt gcctttctct ccacaggtgt ccactcccag gttaccctga gagagtctgg     240
ccctgcgctg gtgaagccca cagaccct cacactgact gtaccttct ctgggttttc       300 actgagcact tctggtatgg gtgtaggctg gattcgtcag cctcccggga aggctctaga     360
gtggctggca cattttggt gggatgatga caagcgctat aatccagccc tgaagagccg      420
actgacaatc tccaaggata cctccaaaaa ccaggtagtc ctcacaatga ccaacatgga     480
ccctgtggat actgccacat actactgtgc tcggataaac cccgcctggt ttgcttactg     540
gggccaaggg actctggtca ctgtgagctc a                                    571

<210> SEQ ID NO 104
<211> LENGTH: 118
<212> TYPE: PRT
<213> ORGANISM: Artificial Sequence
<220> FEATURE:
<223> OTHER INFORMATION: Synthetic Construct

<400> SEQUENCE: 104

Gln Val Thr Leu Arg Glu Ser Gly Pro Ala Leu Val Lys Pro Thr Gln
  1               5                  10                  15

Thr Leu Thr Leu Thr Cys Thr Phe Ser Gly Phe Ser Leu Ser Thr Ser
             20                  25                  30

```
Gly Met Gly Val Gly Trp Ile Arg Gln Pro Pro Gly Lys Ala Leu Glu
            35                  40                  45

Trp Leu Ala His Ile Trp Trp Asp Asp Asp Lys Arg Tyr Asn Pro Ala
        50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ile Asn Pro Ala Trp Phe Ala Tyr Trp Gly Gln Gly Thr
            100                 105                 110

Leu Val Thr Val Ser Ser
        115

<210> SEQ ID NO 105
<211> LENGTH: 1580
<212> TYPE: DNA
<213> ORGANISM: Artificial Sequence
<220> FEATURE:
<223> OTHER INFORMATION: Synthetic Construct

<400> SEQUENCE: 105
gctagcgttt aaacttaagc ttgttgacta gtgagatcac agttctctct acagttactg      60
agcacacagg acctcaccat gggatggagc tgtatcatcc tcttcttggt agcaacagct     120
acaggtaagg ggctcacagt agcaggcttg aggtctggac atatatatgg gtgacaatga     180
catccacttt gcctttctct ccacaggtgt ccactcccag gttaccctga gagagtctgg     240
ccctgcgctg gtgaagccca cagaccct cacactgact tgtaccttct ctgggttttc       300
actgagcact tctggtatgg gtgtaggctg gattcgtcag cctcccggga aggctctaga     360
gtggctggca cacatttggt gggatgatga caagcgctat aatccagccc tgaagagccg     420
actgacaatc tccaaggata cctccaaaaa ccaggtagtc ctcacaatga ccaacatgga     480
ccctgtggat actgccacat actactgtgc tcggataaac cccgcctggt ttgcttactg     540
gggccaaggg actctggtca ctgtgagctc agcctccacc aagggcccat cggtcttccc     600
cctggcaccc tcctccaaga gcacctctgg gggcacagcg gccctgggct gcctggtcaa     660
ggactacttc cccgaaccgg tgacggtgtc gtggaactca ggcgccctga ccagcggcgt     720
gcacaccttc ccggctgtcc tacagtcctc aggactctac tccctcagca gcgtggtgac     780
cgtgccctcc agcagcttgg gcacccagac ctacatctgc aacgtgaatc acaagcccag     840
caacaccaag gtggacaaga gagttgagcc caaatcttgt gacaaaactc acacatgccc     900
accgtgccca gcacctgaac tcctgggggg accgtcagtc ttcctcttcc ccccaaaacc     960
caaggacacc ctcatgatct cccggacccc tgaggtcaca tgcgtggtgg tggacgtgag    1020
ccacgaagac cctgaggtca agttcaactg gtacgtggac ggcgtggagg tgcataatgc    1080
caagacaaag ccgcgggagg agcagtacaa cagcacgtac cgtgtggtca gcgtcctcac    1140
cgtcctgcac caggactggc tgaatggcaa ggagtacaag tgcaaggtct ccaacaaagc    1200
cctcccagcc cccatcgaga aaaccatctc caaagccaaa gggcagcccc gagaaccaca    1260
ggtgtacacc ctgcccccat cccgggatga gctgaccaag aaccaggtca gcctgacctg    1320
cctggtcaaa ggcttctatc ccagcgacat cgccgtggag tgggagagca atgggcagcc    1380
ggagaacaac tacaagacca cgcctcccgt gctggactcc gacggctcct tcttcctcta    1440
cagcaagctc accgtggaca agagcaggtg gcagcagggg aacgtcttct catgctccgt    1500
gatgcatgag gctctgcaca accactacac gcagaagagc ctctccctgt ctccgggtaa    1560
```
atgagtgcgg ccgcgaattc                                                        1580

<210> SEQ ID NO 106
<211> LENGTH: 528
<212> TYPE: DNA
<213> ORGANISM: Artificial Sequence
<220> FEATURE:
<223> OTHER INFORMATION: Synthetic Construct

<400> SEQUENCE: 106
cgagctagct gagatcacag ttctctctac agttactgag cacacaggac ctcaccatgg    60
gatggagctg tatcatcctc ttcttggtag caacagctac aggtaagggg ctcacagtag   120
caggcttgag gtctggacat atatatgggt gacaatgaca tccactttgc ctttctctcc   180
acaggtgtcc actccgacat cgtgatgacc caatctccag actctttggc tgtgtctcta   240
ggggagaggg ccaccatcaa ctgcaagtcc agccaaagtg ttgattttga tggtgatagt   300
tttatgaact ggtaccaaca gaaaccagga cagccaccca aactcctcat ctatactaca   360
tccaatctag aaactggggt cccagacagg tttagtggca gtgggtctgg gacagacttc   420
accctcacca tcagcagcct gcaggctgag gatgtggcag tttattactg tcagcaaagt   480
aattcggatc cgtacacgtt cggacagggg accaagcttg agatcaaa                528

<210> SEQ ID NO 107
<211> LENGTH: 448
<212> TYPE: PRT
<213> ORGANISM: Artificial Sequence
<220> FEATURE:
<223> OTHER INFORMATION: Synthetic Construct

<400> SEQUENCE: 107

Gln Val Thr Leu Arg Glu Ser Gly Pro Ala Leu Val Lys Pro Thr Gln
 1               5                  10                  15

Thr Leu Thr Leu Thr Cys Thr Phe Ser Gly Phe Ser Leu Ser Thr Ser
            20                  25                  30

Gly Met Gly Val Gly Trp Ile Arg Gln Pro Pro Gly Lys Ala Leu Glu
        35                  40                  45

Trp Leu Ala His Ile Trp Trp Asp Asp Lys Arg Tyr Asn Pro Ala
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ile Asn Pro Ala Trp Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

```
Asn Thr Lys Val Asp Lys Arg Val Glu Pro Lys Ser Cys Asp Lys Thr
    210                 215                 220
His Thr Cys Pro Pro Cys Pro Ala Pro Glu Leu Leu Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser His Glu Asp Pro
            260                 265                 270
Glu Val Lys Phe Asn Trp Tyr Val Asp Gly Val Glu Val His Asn Ala
        275                 280                 285
Lys Thr Lys Pro Arg Glu Glu Gln Tyr Asn Ser Thr Tyr Arg Val Val
    290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
            340                 345                 350
Pro Pro Ser Arg Asp Glu Leu Thr Lys Asn Gln Val Ser Leu Thr Cys
        355                 360                 365
Leu Val Lys Gly Phe Tyr Pro Ser Asp Ile Ala Val Glu Trp Glu Ser
    370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
            420                 425                 430
Leu His Asn His Tyr Thr Gln Lys Ser Leu Ser Leu Ser Pro Gly Lys
        435                 440                 445
```

<210> SEQ ID NO 108
<211> LENGTH: 571
<212> TYPE: DNA
<213> ORGANISM: Artificial Sequence
<220> FEATURE:
<223> OTHER INFORMATION: Synthetic Construct

<400> SEQUENCE: 108

```
gctagcgttt aaacttaagc ttgttgacta gtgagatcac agttctctct acagttactg    60
agcacacagg acctcaccat gggatggagc tgtatcatcc tcttcttggt agcaacagct   120
acaggtaagg ggctcacagt agcaggcttg aggtctggac atatatatgg gtgacaatga   180
catccacttt gcctttctct ccacaggtgt ccactcccag gttaccctga gagagtctgg   240
ccctgcgctg gtgaagccca cagaccctca cactgactgt gtaccttct ctgggttttc    300
actgagcact tctggtatgg gtgtaggctg gattcgtcag cctcccggga aggctctaga   360
gtggctggca cacatttggt gggatgatga caagcgctat aatccagccc tgaagagccg   420
actgacaatc tccaaggata cctccaaaaa ccaggtagtc ctcacaatga ccaacatgga   480
ccctgtggat actgccacat actactgtgc tcaaataaac cccgcctggt ttgcttactg   540
gggccaaggg actctggtca ctgtgagctc a                                  571
```

<210> SEQ ID NO 109
<211> LENGTH: 118

<212> TYPE: PRT
<213> ORGANISM: Artificial Sequence
<220> FEATURE:
<223> OTHER INFORMATION: Synthetic Construct

<400> SEQUENCE: 109

Gln Val Thr Leu Arg Glu Ser Gly Pro Ala Leu Val Lys Pro Thr Gln
 1               5                  10                  15

Thr Leu Thr Leu Thr Cys Thr Phe Ser Gly Phe Ser Leu Ser Thr Ser
            20                  25                  30

Gly Met Gly Val Gly Trp Ile Arg Gln Pro Pro Gly Lys Ala Leu Glu
        35                  40                  45

Trp Leu Ala His Ile Trp Trp Asp Asp Lys Arg Tyr Asn Pro Ala
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Gln Ile Asn Pro Ala Trp Phe Ala Tyr Trp Gly Gln Gly Thr
            100                 105                 110

Leu Val Thr Val Ser Ser
        115

<210> SEQ ID NO 110
<211> LENGTH: 1580
<212> TYPE: DNA
<213> ORGANISM: Artificial Sequence
<220> FEATURE:
<223> OTHER INFORMATION: Synthetic Construct

<400> SEQUENCE: 110

```
gctagcgttt aaacttaagc ttgttgacta gtgagatcac agttctctct acagttactg      60
agcacacagg acctcaccat gggatggagc tgtatcatcc tcttcttggt agcaacagct     120
acaggtaagg ggctcacagt agcaggcttg aggtctggac atatatatgg gtgacaatga     180
catccacttt gcctttctct ccacaggtgt ccactcccag gttaccctga gagagtctgg     240
ccctgcgctg gtgaagccca cagaccct cacactgact tgtaccttct ctgggttttc       300
actgagcact tctggtatgg gtgtaggctg gattcgtcag cctcccggga aggctctaga     360
gtggctggca cacatttggt gggatgatga caagcgctat aatccagccc tgaagagccg     420
actgacaatc tccaaggata cctccaaaaa ccaggtagtc ctcacaatga ccaacatgga     480
ccctgtggat actgccacat actactgtgc tcaaataaac cccgcctggt ttgcttactg     540
gggccaaggg actctggtca ctgtgagctc agcctccacc aagggcccat cggtcttccc     600
cctggcaccc tcctccaaga gcacctctgg gggcacagcg gccctgggct gcctggtcaa     660
ggactacttc cccgaaccgg tgacggtgtc gtggaactca ggcgccctga ccagcggcgt     720
gcacaccttc ccggctgtcc tacagtcctc aggactctac tccctcagca gcgtggtgac     780
cgtgccctcc agcagcttgg gcacccagac ctacatctgc aacgtgaatc acaagcccag     840
caacaccaag gtggacaaga gagttgagcc caaatcttgt gacaaaactc acacatgccc     900
accgtgccca gcacctgaac tcctgggggg accgtcagtc ttcctcttcc ccccaaaacc     960
caaggacacc ctcatgatct cccggacccc tgaggtcaca tgcgtggtgg tggacgtgag    1020
ccacgaagac cctgaggtca agttcaactg gtacgtggac ggcgtggagg tgcataatgc    1080
caagacaaag ccgcgggagg agcagtacca gagcacgtac cgtgtggtca gcgtcctcac    1140
```

```
cgtcctgcac caggactggc tgaatggcaa ggagtacaag tgcaaggtct ccaacaaagc    1200
cctcccagcc cccatcgaga aaccatctc caaagccaaa gggcagcccc gagaaccaca    1260
ggtgtacacc ctgcccccat cccgggatga gctgaccaag aaccaggtca gcctgacctg    1320
cctggtcaaa ggcttctatc ccagcgacat cgccgtggag tgggagagca atgggcagcc    1380
ggagaacaac tacaagacca cgcctcccgt gctggactcc gacggctcct tcttcctcta    1440
cagcaagctc accgtggaca agagcaggtg gcagcagggg aacgtcttct catgctccgt    1500
gatgcatgag gctctgcaca accactacac gcagaagagc ctctccctgt ctccgggtaa    1560
atgagtgcgg ccgcgaattc                                                1580
```

```
<210> SEQ ID NO 111
<211> LENGTH: 448
<212> TYPE: PRT
<213> ORGANISM: Artificial Sequence
<220> FEATURE:
<223> OTHER INFORMATION: Synthetic Construct

<400> SEQUENCE: 111

Gln Val Thr Leu Arg Glu Ser Gly Pro Ala Leu Val Lys Pro Thr Gln
 1               5                   10                  15

Thr Leu Thr Leu Thr Cys Thr Phe Ser Gly Phe Ser Leu Ser Thr Ser
             20                  25                  30

Gly Met Gly Val Gly Trp Ile Arg Gln Pro Pro Gly Lys Ala Leu Glu
         35                  40                  45

Trp Leu Ala His Ile Trp Trp Asp Asp Lys Arg Tyr Asn Pro Ala
     50                  55                  60

Leu Lys Ser Arg Leu Thr Ile Ser Lys Asp Thr Ser Lys Asn Gln Val
 65                  70                  75                  80

Val Leu Thr Met Thr Asn Met Asp Pro Val Asp Thr Ala Thr Tyr Tyr
                 85                  90                  95

Cys Ala Gln Ile Asn Pro Ala Trp Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285
```

Lys Thr Lys Pro Arg Glu Glu Gln Tyr Gln Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 112
<211> LENGTH: 571
<212> TYPE: DNA
<213> ORGANISM: Artificial Sequence
<220> FEATURE:
<223> OTHER INFORMATION: Synthetic Construct

<400> SEQUENCE: 112
gctagcgttt aaacttaagc ttgttgacta gtgagatcac agttctctct acagttactg      60
agcacacagg acctcaccat gggatggagc tgtatcatcc tcttcttggt agcaacagct     120
acaggtaagg ggctcacagt agcaggcttg aggtctggac atatatatgg gtgacaatga     180
catccacttt gcctttctct ccacaggtgt ccactcccag gttaccctga gagagtctgg     240
ccctgcgctg gtgaagccca cagaccct cacactgact tgtaccttct ctgggttttc     300
actgagcact tctggtgtgg gtgtaggctg gattcgtcag cctcccggga aggctctaga     360
gtggctggca cacatttggt gggatgatga caagcgctat tctccatccc tgaagagccg     420
actgacaatc tccaaggata cctccaaaaa ccaggtagtc ctcacaatga ccaacatgga     480
ccctgtggat actgccacat actactgtgc tcggataaac cccgcctact tgcttactg     540 gggccaaggg actctggtca ctgtgagctc a     571

<210> SEQ ID NO 113
<211> LENGTH: 117
<212> TYPE: PRT
<213> ORGANISM: Artificial Sequence
<220> FEATURE:
<223> OTHER INFORMATION: Synthetic Construct

<400> SEQUENCE: 113

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
        35                  40                  45

-continued

```
Trp Leu Ala His Ile Trp Trp Asp Asp Lys Arg Tyr Ser Pro Ser
 50                  55                  60
Leu Lys Ser Arg Leu Thr Ile Ser Lys Asp Thr Ser Lys Asn Gln Val
 65                  70                  75                  80
Val Leu Thr Met Thr Asn Met Asp Pro Val Asp Thr Ala Thr Tyr Tyr
                 85                  90                  95
Cys Ala Arg Ile Asn Pro Ala Tyr Phe Ala Tyr Trp Gly Gln Gly Thr
             100                 105                 110
Leu Val Thr Val Ser
            115

<210> SEQ ID NO 114
<211> LENGTH: 1580
<212> TYPE: DNA
<213> ORGANISM: Artificial Sequence
<220> FEATURE:
<223> OTHER INFORMATION: Synthetic Construct

<400> SEQUENCE: 114
gctagcgttt aaacttaagc ttgttgacta gtgagatcac agttctctct acagttactg      60
agcacacagg acctcaccat gggatggagc tgtatcatcc tcttcttggt agcaacagct     120
acaggtaagg ggctcacagt agcaggcttg aggtctggac atatatatgg gtgacaatga     180
catccacttt gcctttctct ccacaggtgt ccactcccag gttaccctga gagagtctgg     240
ccctgcgctg gtgaagccca cagaccct cacactgact tgtaccttct ctgggttttc       300
actgagcact tctggtgtgg gtgtaggctg gattcgtcag cctcccggga aggctctaga     360
gtggctggca cacatttggt gggatgatga caagcgctat tctccatccc tgaagagccg     420
actgacaatc tccaaggata cctccaaaaa ccaggtagtc ctcacaatga ccaacatgga     480
ccctgtggat actgccacat actactgtgc tcggataaac cccgcctact ttgcttactg     540
gggccaaggg actctggtca ctgtgagctc agcctccacc aagggcccat cggtcttccc     600
cctggcaccc tcctccaaga gcacctctgg gggcacagcg gccctgggct gcctggtcaa     660
ggactacttc cccgaaccgg tgacggtgtc gtggaactca ggcgccctga ccagcggcgt     720
gcacaccttc ccggctgtcc tacagtcctc aggactctac tccctcagca gcgtggtgac     780
cgtgccctcc agcagcttgg gcacccagac ctacatctgc aacgtgaatc acaagcccag     840
caacaccaag gtggacaaga gagttgagcc caaatcttgt gacaaaactc acacatgccc     900
accgtgccca gcacctgaac tcctgggggg accgtcagtc ttcctcttcc ccccaaaacc     960
caaggacacc ctcatgatct cccggacccc tgaggtcaca tgcgtggtgg tggacgtgag    1020
ccacgaagac cctgaggtca agttcaactg gtacgtggac ggcgtggagg tgcataatgc    1080
caagacaaag ccgcgggagg agcagtacca gagcacgtac cgtgtggtca gcgtcctcac    1140
cgtcctgcac caggactggc tgaatggcaa ggagtacaag tgcaaggtct ccaacaaagc    1200
cctcccagcc cccatcgaga aaaccatctc caaagccaaa gggcagcccc gagaaccaca    1260
ggtgtacacc ctgcccccat cccgggatga gctgaccaag aaccaggtca gcctgacctg    1320
cctggtcaaa ggcttctatc ccagcgacat cgccgtggag tgggagagca atgggcagcc    1380
ggagaacaac tacaagacca cgcctcccgt gctggactcc gacggctcct tcttcctcta    1440
cagcaagctc accgtggaca agagcaggtg gcagcagggg aacgtcttct catgctccgt    1500
gatgcatgag gctctgcaca accactacac gcagaagagc ctctccctgt ctccgggtaa    1560
atgagtgcgg ccgcgaattc                                                1580
```

```
<210> SEQ ID NO 115
<211> LENGTH: 448
<212> TYPE: PRT
<213> ORGANISM: Artificial Sequence
<220> FEATURE:
<223> OTHER INFORMATION: Synthetic Construct

<400> SEQUENCE: 115

Gln Val Thr Leu Arg Glu Ser Gly Pro Ala Leu Val Lys Pro Thr Gln
  1               5                  10                  15

Thr Leu Thr Leu Thr Cys Thr Phe Ser Gly Phe Ser Leu Ser Thr Ser
             20                  25                  30

Gly Val Gly Val Gly Trp Ile Arg Gln Pro Pro Gly Lys Ala Leu Glu
         35                  40                  45

Trp Leu Ala His Ile Trp Trp Asp Asp Lys Arg Tyr Ser Pro Ser
     50                  55                  60

Leu Lys Ser Arg Leu Thr Ile Ser Lys Asp Thr Ser Lys Asn Gln Val
 65                  70                  75                  80

Val Leu Thr Met Thr Asn Met Asp Pro Val Asp Thr Ala Thr Tyr Tyr
                 85                  90                  95

Cys Ala Arg Ile Asn Pro Ala Tyr Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Gln Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365
```

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
                435                 440                 445

<210> SEQ ID NO 116
<211> LENGTH: 254
<212> TYPE: PRT
<213> ORGANISM: Homo Sapien

<400> SEQUENCE: 116

Met Trp Gln Leu Leu Leu Pro Thr Ala Leu Leu Leu Leu Val Ser Ala
  1               5                  10                  15

Gly Met Arg Thr Glu Asp Leu Pro Lys Ala Val Val Phe Leu Glu Pro
             20                  25                  30

Gln Trp Tyr Arg Val Leu Glu Lys Asp Ser Val Thr Leu Lys Cys Gln
         35                  40                  45

Gly Ala Tyr Ser Pro Glu Asp Asn Ser Thr Gln Trp Phe His Asn Glu
     50                  55                  60

Ser Leu Ile Ser Ser Gln Ala Ser Ser Tyr Phe Ile Asp Ala Ala Thr
 65                  70                  75                  80

Val Asp Asp Ser Gly Glu Tyr Arg Cys Gln Thr Asn Leu Ser Thr Leu
                 85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
        115                 120                 125

His Ser Trp Lys Asn Thr Ala Leu His Lys Val Thr Tyr Leu Gln Asn
    130                 135                 140

Gly Lys Gly Arg Lys Tyr Phe His His Asn Ser Asp Phe Tyr Ile Pro
145                 150                 155                 160

Lys Ala Thr Leu Lys Asp Ser Gly Ser Tyr Phe Cys Arg Gly Leu Phe
                165                 170                 175

Gly Ser Lys Asn Val Ser Ser Glu Thr Val Asn Ile Thr Ile Thr Gln
            180                 185                 190

Gly Leu Ala Val Ser Thr Ile Ser Ser Phe Phe Pro Pro Gly Tyr Gln
        195                 200                 205

Val Ser Phe Cys Leu Val Met Val Leu Leu Phe Ala Val Asp Thr Gly
    210                 215                 220

Leu Tyr Phe Ser Val Lys Thr Asn Ile Arg Ser Ser Thr Arg Asp Trp
225                 230                 235                 240

Lys Asp His Lys Phe Lys Trp Arg Lys Asp Pro Gln Asp Lys
                245                 250

<210> SEQ ID NO 117
<211> LENGTH: 254
<212> TYPE: PRT
<213> ORGANISM: Homo Sapien

<400> SEQUENCE: 117

```
Met Trp Gln Leu Leu Leu Pro Thr Ala Leu Leu Leu Val Ser Ala
1               5                   10                  15

Gly Met Arg Thr Glu Asp Leu Pro Lys Ala Val Val Phe Leu Glu Pro
            20                  25                  30

Gln Trp Tyr Arg Val Leu Glu Lys Asp Ser Val Thr Leu Lys Cys Gln
            35                  40                  45

Gly Ala Tyr Ser Pro Glu Asp Asn Ser Thr Gln Trp Phe His Asn Glu
        50                  55                  60

Ser Leu Ile Ser Ser Gln Ala Ser Ser Tyr Phe Ile Asp Ala Ala Thr
65                  70                  75                  80

Val Asp Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
        115                 120                 125

His Ser Trp Lys Asn Thr Ala Leu His Lys Val Thr Tyr Leu Gln Asn
    130                 135                 140

Gly Lys Gly Arg Lys Tyr Phe His His Asn Ser Asp Phe Tyr Ile Pro
145                 150                 155                 160

Lys Ala Thr Leu Lys Asp Ser Gly Ser Tyr Phe Cys Arg Gly Leu Val
                165                 170                 175

Gly Ser Lys Asn Val Ser Ser Glu Thr Val Asn Ile Thr Ile Thr Gln
            180                 185                 190

Gly Leu Ala Val Ser Thr Ile Ser Ser Phe Phe Pro Pro Gly Tyr Gln
        195                 200                 205

Val Ser Phe Cys Leu Val Met Val Leu Leu Phe Ala Val Asp Thr Gly
    210                 215                 220

Leu Tyr Phe Ser Val Lys Thr Asn Ile Arg Ser Ser Thr Arg Asp Trp
225                 230                 235                 240

Lys Asp His Lys Phe Lys Trp Arg Lys Asp Pro Gln Asp Lys
                245                 250

<210> SEQ ID NO 118
<211> LENGTH: 111
<212> TYPE: PRT
<213> ORGANISM: Artificial Sequence
<220> FEATURE:
<223> OTHER INFORMATION: Synthetic Construct

<400> SEQUENCE: 118

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Asp Phe Asp
            20                  25                  30

Gly Asp Ser Phe Met Asn Trp Tyr Gln Gln Lys Pro Gly Gln Pro Pro
        35                  40                  45

Lys Leu Leu Ile Tyr Thr Thr Ser Asn Leu Glu Thr Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

Ser Asp Pro Tyr Thr Phe Gly Gln Gly Thr Lys Leu Glu Ile Lys
            100                 105                 110
```

```
<210> SEQ ID NO 119
<211> LENGTH: 218
<212> TYPE: PRT
<213> ORGANISM: Artificial Sequence
<220> FEATURE:
<223> OTHER INFORMATION: Synthetic Construct

<400> SEQUENCE: 119

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Val Asp Phe Asp
            20                  25                  30

Gly Asp Ser Phe Met Asn Trp Tyr Gln Gln Lys Pro Gly Gln Pro Pro
        35                  40                  45

Lys Leu Leu Ile Tyr Thr Thr Ser Asn Leu Glu Thr Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

Ser Asp Pro Tyr Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```